United States Patent
Ellison

(10) Patent No.: US 9,005,907 B2
(45) Date of Patent: Apr. 14, 2015

(54) METHODS AND COMPOSITIONS FOR TYPING MOLECULAR SUBGROUPS OF MEDULLOBLASTOMA

(75) Inventor: David Ellison, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 13/818,213

(22) PCT Filed: Sep. 30, 2011

(86) PCT No.: PCT/US2011/054197
§ 371 (c)(1),
(2), (4) Date: Mar. 4, 2013

(87) PCT Pub. No.: WO2012/044921
PCT Pub. Date: Apr. 5, 2012

(65) Prior Publication Data
US 2014/0155400 A1 Jun. 5, 2014

Related U.S. Application Data

(60) Provisional application No. 61/388,874, filed on Oct. 1, 2010.

(51) Int. Cl.
*G01N 33/53* (2006.01)
*G01N 33/567* (2006.01)
*G01N 33/574* (2006.01)

(52) U.S. Cl.
CPC ...... *G01N 33/57407* (2013.01); *G01N 2800/52* (2013.01)

(58) Field of Classification Search
None
See application file for complete search history.

(56) References Cited

PUBLICATIONS

Thompson et al., J Clin Oncol. Apr. 20, 2006;24(12)1924-1931.*

David Ellison, et al., "beta-Catenin status predicts a favorable outcome in childhood medulloblastoma: the United Kingdom Children's Cancer Study Group Brain Tumour Committee," *Journal of Clinical Oncology*, Nov. 1, 2005, 7951-7957: vol. 23(31), American Society of Clinical Oncology, U.S.

David Ellison, "Childhood medulloblastoma: novel approaches to the classification of a heterogeneous disease," *Acta Neuropathologica*, Jul. 23, 2010, 305-316, vol. 120(3), Springer, Berlin, Germany.

David Ellison, et al., "Medulloblastoma: clinicopathological correlates to SHH, WNT, and non-SHH/WNT molecular subgroups," *Acta Neuropathologica*, Jan. 26, 2011, 381-396, vol. 121(3), Springer, Berlin, Germany.

Sarah Fattet, et al., "Beta-catenin status in paediatric medulloblastomas: correlation with mutational status, genetic profiles, and clinical characteristics," *Journal of Pathology*, May 1, 2009, 86-94, vol. 218(1), John Wiley & Sons, Ltd., Great Britain.

Africa Fernandez-L, et al., "YAP1 is amplified and up-regulated in hedgehog-associated medulloblastomas and mediates Sonic hedgehog-driven neural precursor proliferation," *Genes and Development*, Dec. 1, 2009, 2729-2741, vol. 23(23), Cold Spring Harbor Laboratory Press, Plainview, NY, US.

International Search Report of PTC/US2011/054197, date of mailing Jan. 9, 2012.

* cited by examiner

*Primary Examiner* — Daniel C Gamett
(74) *Attorney, Agent, or Firm* — Alston & Bird LLP

(57) ABSTRACT

Immunohistochemical methods and compositions for the typing of molecular subgroups of medulloblastomas are provided. The methods comprise determining a protein expression profile for a sample obtained from a medulloblastoma by detecting expression of GAB1, filamin A, or at least two biomarker proteins selected from the group consisting of β-catenin, YAP1, GAB1, and filamin A, and typing the medulloblastoma as a WNT pathway tumor, a SHH pathway tumor, or a non-WNT/non-SHH tumor based on this protein expression profile. Kits for typing a medulloblastoma according to these three molecular subgroups are provided. The kits comprise at least two antibodies, wherein each of said antibodies specifically binds to a distinct biomarker protein selected from the group consisting of β-catenin, YAP1, GAB1, and filamin A, and can optionally comprise one or more of instructions for use, reagents for detecting antibody binding to one or more of said biomarker proteins, and one or more positive control samples.

25 Claims, 1 Drawing Sheet

| #U113 FILE | CTNNB1 mutation | PTCH1 mutation | Pathological variant | Molecular Subgroup | β-catenin IHC | Filamin A IHC | GAB1 IHC | YAP1 IHC |
|---|---|---|---|---|---|---|---|---|
| 103 | | | classic | A | C-intermediate | negative | negative | negative |
| 118 | | | anaplastic | A | C-intermediate | negative | negative | negative |
| 121 | | | anaplastic | A | C-strong | negative | negative | negative |
| 80 | | | anaplastic | A | C-intermediate/focal | negative | negative | negative |
| 98 | | | classic | A | C-strong | negative | negative | negative |
| 131 | | | anaplastic | A | C-strong focal | negative | negative | negative |
| 140 | | | classic-GNB | A | C-strong | negative | negative | negative |
| 125 | X | | classic | B | N-strong | C-weak/focal | negative | N & C-strong |
| 139 | X | | classic | B | N-strong | C-intermediate/focal | negative | N & C-strong |
| 84 | | | classic | B | N-strong | C-intermediate/focal | negative | N & C-strong |
| 143 | X | | classic | B | N-strong | C-intermediate/focal | negative | N & C-strong |
| 92 | | | classic | C | C-strong | negative | negative | negative |
| 79 | | | classic | C | C-intermediate/focal | negative | negative | negative |
| 129 | | | classic | C | C-intermediate | negative | negative | negative |
| 130 | | | classic | C | C-intermediate | negative | negative | negative |
| 81 | | | classic | C | C-strong | negative | negative | negative |
| 96 | | | classic | C | C-intermediate | negative | negative | negative |
| 89 | | | classic | C | C-intermediate | negative | negative | negative |
| 90 | | X | anaplastic | C' | C-intermediate | C-intermediate | C-strong | N & C-strong |
| 102 | | | anaplastic | D | C-intermediate | C-intermediate | C-intermediate | N & C-strong |
| 126 | | X | D/N | D | C-intermediate (nodules) | C-intermediate (nodules) | C-intermediate (nodules) | N & C-strong (nodules) |
| 127 | | X | D/N | D | C-strong (nodules) | C-strong (nodules) | C-intermediate (nodules) | N & C-strong (nodules) |
| 109 | | | D/N | D | C-strong (nodules) | C-strong (nodules) | C-intermediate (nodules) | N & C-strong (nodules) |
| 114 | | | classic | E | C-strong | negative | negative | negative |
| 153 | | | anaplastic | E | C-intermediate | negative | negative | negative |

SEQUENCE LISTING

```
<160> NUMBER OF SEQ ID NOS: 14

<210> SEQ ID NO 1
<211> LENGTH: 2346
<212> TYPE: DNA
<213> ORGANISM: Homo sapiens
<220> FEATURE:
<221> NAME/KEY: CDS
<222> LOCATION: (1)...(2346)
<223> OTHER INFORMATION: Coding sequence for human beta-catenin

<400> SEQUENCE: 1 atg gct act caa gct gat ttg atg gag ttg gac atg gcc atg gaa cca        48
Met Ala Thr Gln Ala Asp Leu Met Glu Leu Asp Met Ala Met Glu Pro
 1               5                  10                  15 gac aga aaa gcg gct gtt agt cac tgg cag caa cag tct tac ctg gac        96
Asp Arg Lys Ala Ala Val Ser His Trp Gln Gln Gln Ser Tyr Leu Asp
                20                  25                  30 tct gga atc cat tct ggt gcc act acc aca gct cct tct ctg agt ggt       144
Ser Gly Ile His Ser Gly Ala Thr Thr Thr Ala Pro Ser Leu Ser Gly
            35                  40                  45 aaa ggc aat cct gag gaa gag gat gtg gat acc tcc caa gtc ctg tat       192
Lys Gly Asn Pro Glu Glu Glu Asp Val Asp Thr Ser Gln Val Leu Tyr
        50                  55                  60 gag tgg gaa cag gga ttt tct cag tcc ttc act caa gaa caa gta gct       240
Glu Trp Glu Gln Gly Phe Ser Gln Ser Phe Thr Gln Glu Gln Val Ala
 65                  70                  75                  80 gat att gat gga cag tat gca atg act cga gct cag agg gta cga gct       288
Asp Ile Asp Gly Gln Tyr Ala Met Thr Arg Ala Gln Arg Val Arg Ala
                85                  90                  95 gct atg ttc cct gag aca tta gat gag ggc atg cag atc cca tct aca       336
Ala Met Phe Pro Glu Thr Leu Asp Glu Gly Met Gln Ile Pro Ser Thr
               100                 105                 110 cag ttt gat gct gct cat ccc act aat gtc cag cgt ttg gct gaa cca       384
Gln Phe Asp Ala Ala His Pro Thr Asn Val Gln Arg Leu Ala Glu Pro
           115                 120                 125 tca cag atg ctg aaa cat gca gtt gta aac ttg att aac tat caa gat       432
Ser Gln Met Leu Lys His Ala Val Val Asn Leu Ile Asn Tyr Gln Asp
       130                 135                 140 gat gca gaa ctt gcc aca cgt gca atc cct gaa ctg aca aaa ctg cta       480
Asp Ala Glu Leu Ala Thr Arg Ala Ile Pro Glu Leu Thr Lys Leu Leu
```

```
                         -continued 145                 150                 155                 160 aat gac gag gac cag gtg gtg gtt aat aag gct gca gtt atg gtc cat      528
Asn Asp Glu Asp Gln Val Val Val Asn Lys Ala Ala Val Met Val His
                    165                 170                 175 cag ctt tct aaa aag gaa gct tcc aga cac gct atc atg cgt tct cct      576
Gln Leu Ser Lys Lys Glu Ala Ser Arg His Ala Ile Met Arg Ser Pro
            180                 185                 190 cag atg gtg tct gct att gta cgt acc atg cag aat aca aat gat gta      624
Gln Met Val Ser Ala Ile Val Arg Thr Met Gln Asn Thr Asn Asp Val
                195                 200                 205 gaa aca gct cgt tgt acc gct ggg acc ttg cat aac ctt tcc cat cat      672
Glu Thr Ala Arg Cys Thr Ala Gly Thr Leu His Asn Leu Ser His His
210                 215                 220 cgt gag ggc tta ctg gcc atc ttt aag tct gga ggc att cct gcc ctg      720
Arg Glu Gly Leu Leu Ala Ile Phe Lys Ser Gly Gly Ile Pro Ala Leu
225                 230                 235                 240 gtg aaa atg ctt ggt tca cca gtg gat tct gtg ttg ttt tat gcc att      768
Val Lys Met Leu Gly Ser Pro Val Asp Ser Val Leu Phe Tyr Ala Ile
                    245                 250                 255 aca act ctc cac aac ctt tta tta cat caa gaa gga gct aaa atg gca      816
Thr Thr Leu His Asn Leu Leu Leu His Gln Glu Gly Ala Lys Met Ala
                260                 265                 270 gtg cgt tta gct ggt ggg ctg cag aaa atg gtt gcc ttg ctc aac aaa      864
Val Arg Leu Ala Gly Gly Leu Gln Lys Met Val Ala Leu Leu Asn Lys
            275                 280                 285 aca aat gtt aaa ttc ttg gct att acg aca gac tgc ctt caa att tta      912
Thr Asn Val Lys Phe Leu Ala Ile Thr Thr Asp Cys Leu Gln Ile Leu
        290                 295                 300 gct tat ggc aac caa gaa agc aag ctc atc ata ctg gct agt ggt gga      960
Ala Tyr Gly Asn Gln Glu Ser Lys Leu Ile Ile Leu Ala Ser Gly Gly
305                 310                 315                 320 ccc caa gct tta gta aat ata atg agg acc tat act tac gaa aaa cta     1008
Pro Gln Ala Leu Val Asn Ile Met Arg Thr Tyr Thr Tyr Glu Lys Leu
                    325                 330                 335 ctg tgg acc aca agc aga gtg ctg aag gtg cta tct gtc tgc tct agt     1056
Leu Trp Thr Thr Ser Arg Val Leu Lys Val Leu Ser Val Cys Ser Ser
                340                 345                 350 aat aag ccg gct att gta gaa gct ggt gga atg caa gct tta gga ctt     1104
Asn Lys Pro Ala Ile Val Glu Ala Gly Gly Met Gln Ala Leu Gly Leu
            355                 360                 365 cac ctg aca gat cca agt caa cgt ctt gtt cag aac tgt ctt tgg act     1152
His Leu Thr Asp Pro Ser Gln Arg Leu Val Gln Asn Cys Leu Trp Thr
        370                 375                 380 ctc agg aat ctt tca gat gct gca act aaa cag gaa ggg atg gaa ggt     1200
Leu Arg Asn Leu Ser Asp Ala Ala Thr Lys Gln Glu Gly Met Glu Gly
385                 390                 395                 400 ctc ctt ggg act ctt gtt cag ctt ctg ggt tca gat gat ata aat gtg     1248
Leu Leu Gly Thr Leu Val Gln Leu Leu Gly Ser Asp Asp Ile Asn Val
                    405                 410                 415 gtc acc tgt gca gct gga att ctt tct aac ctc act tgc aat aat tat     1296
Val Thr Cys Ala Ala Gly Ile Leu Ser Asn Leu Thr Cys Asn Asn Tyr
                420                 425                 430 aag aac aag atg atg gtc tgc caa gtg ggt ggt ata gag gct ctt gtg     1344
Lys Asn Lys Met Met Val Cys Gln Val Gly Gly Ile Glu Ala Leu Val
            435                 440                 445 cgt act gtc ctt cgg gct ggt gac agg gaa gac atc act gag cct gcc     1392
Arg Thr Val Leu Arg Ala Gly Asp Arg Glu Asp Ile Thr Glu Pro Ala
        450                 455                 460 atc tgt gct ctt cgt cat ctg acc agc cga cac caa gaa gca gag atg     1440
```

```
                                                                                  -continued Ile Cys Ala Leu Arg His Leu Thr Ser Arg His Gln Glu Ala Glu Met
465                 470                 475                 480 gcc cag aat gca gtt cgc ctt cac tat gga cta cca gtt gtg gtt aag    1488
Ala Gln Asn Ala Val Arg Leu His Tyr Gly Leu Pro Val Val Val Lys
                    485                 490                 495 ctc tta cac cca cca tcc cac tgg cct ctg ata aag gct act gtt gga    1536
Leu Leu His Pro Pro Ser His Trp Pro Leu Ile Lys Ala Thr Val Gly
                500                 505                 510 ttg att cga aat ctt gcc ctt tgt ccc gca aat cat gca cct ttg cgt    1584
Leu Ile Arg Asn Leu Ala Leu Cys Pro Ala Asn His Ala Pro Leu Arg
            515                 520                 525 gag cag ggt gcc att cca cga cta gtt cag ttg ctt gtt cgt gca cat    1632
Glu Gln Gly Ala Ile Pro Arg Leu Val Gln Leu Leu Val Arg Ala His
        530                 535                 540 cag gat acc cag cgc cgt acg tcc atg ggt ggg aca cag cag caa ttt    1680
Gln Asp Thr Gln Arg Arg Thr Ser Met Gly Gly Thr Gln Gln Gln Phe
545                 550                 555                 560 gtg gag ggg gtc cgc atg gaa gaa ata gtt gaa ggt tgt acc gga gcc    1728
Val Glu Gly Val Arg Met Glu Glu Ile Val Glu Gly Cys Thr Gly Ala
                565                 570                 575 ctt cac atc cta gct cgg gat gtt cac aac cga att gtt atc aga gga    1776
Leu His Ile Leu Ala Arg Asp Val His Asn Arg Ile Val Ile Arg Gly
                580                 585                 590 cta aat acc att cca ttg ttt gtg cag ctg ctt tat tct ccc att gaa    1824
Leu Asn Thr Ile Pro Leu Phe Val Gln Leu Leu Tyr Ser Pro Ile Glu
            595                 600                 605 aac atc caa aga gta gct gca ggg gtc ctc tgt gaa ctt gct cag gac    1872
Asn Ile Gln Arg Val Ala Ala Gly Val Leu Cys Glu Leu Ala Gln Asp
        610                 615                 620 aag gaa gct gca gaa gct att gaa gct gag gga gcc aca gct cct ctg    1920
Lys Glu Ala Ala Glu Ala Ile Glu Ala Glu Gly Ala Thr Ala Pro Leu
625                 630                 635                 640 aca gag tta ctt cac tct agg aat gaa ggt gtg gcg aca tat gca gct    1968
Thr Glu Leu Leu His Ser Arg Asn Glu Gly Val Ala Thr Tyr Ala Ala
                645                 650                 655 gct gtt ttg ttc cga atg tct gag gac aag cca caa gat tac aag aaa    2016
Ala Val Leu Phe Arg Met Ser Glu Asp Lys Pro Gln Asp Tyr Lys Lys
                660                 665                 670 cgg ctt tca gtt gag ctg acc agc tct ctc ttc aga aca gag cca atg    2064
Arg Leu Ser Val Glu Leu Thr Ser Ser Leu Phe Arg Thr Glu Pro Met
            675                 680                 685 gct tgg aat gag act gct gat ctt gga ctt gat att ggt gcc cag gga    2112
Ala Trp Asn Glu Thr Ala Asp Leu Gly Leu Asp Ile Gly Ala Gln Gly
        690                 695                 700 gaa ccc ctt gga tat cgc cag gat gat cct agc tat cgt tct ttt cac    2160
Glu Pro Leu Gly Tyr Arg Gln Asp Asp Pro Ser Tyr Arg Ser Phe His
705                 710                 715                 720 tct ggt gga tat ggc cag gat gcc ttg ggt atg gac ccc atg atg gaa    2208
Ser Gly Gly Tyr Gly Gln Asp Ala Leu Gly Met Asp Pro Met Met Glu
                725                 730                 735 cat gag atg ggt ggc cac cac cct ggt gct gac tat cca gtt gat ggg    2256
His Glu Met Gly Gly His His Pro Gly Ala Asp Tyr Pro Val Asp Gly
                740                 745                 750 ctg cca gat ctg ggg cat gcc cag gac ctc atg gat ggg ctg cct cca    2304
Leu Pro Asp Leu Gly His Ala Gln Asp Leu Met Asp Gly Leu Pro Pro
            755                 760                 765 ggt gac agc aat cag ctg gcc tgg ttt gat act gac ctg taa             2346
Gly Asp Ser Asn Gln Leu Ala Trp Phe Asp Thr Asp Leu
770                 775                 780
```

```
<210> SEQ ID NO 2
<211> LENGTH: 781
<212> TYPE: PRT
<213> ORGANISM: Homo sapiens
<220> FEATURE:
<223> OTHER INFORMATION: Human beta-catenin

<400> SEQUENCE: 2
```

| | | | | | | | | | | | | | | |
|---|---|---|---|---|---|---|---|---|---|---|---|---|---|---|
| Met | Ala | Thr | Gln | Ala | Asp | Leu | Met | Glu | Leu | Asp | Met | Ala | Met | Glu | Pro |
| 1 | | | | 5 | | | | | 10 | | | | | 15 | |
| Asp | Arg | Lys | Ala | Ala | Val | Ser | His | Trp | Gln | Gln | Gln | Ser | Tyr | Leu | Asp |
| | | | 20 | | | | | 25 | | | | | 30 | | |
| Ser | Gly | Ile | His | Ser | Gly | Ala | Thr | Thr | Thr | Ala | Pro | Ser | Leu | Ser | Gly |
| | | 35 | | | | | 40 | | | | | 45 | | | |
| Lys | Gly | Asn | Pro | Glu | Glu | Asp | Val | Asp | Thr | Ser | Gln | Val | Leu | Tyr |
| | 50 | | | | | 55 | | | | | 60 | | | | |
| Glu | Trp | Glu | Gln | Gly | Phe | Ser | Gln | Ser | Phe | Thr | Gln | Glu | Gln | Val | Ala |
| 65 | | | | | 70 | | | | | 75 | | | | | 80 |
| Asp | Ile | Asp | Gly | Gln | Tyr | Ala | Met | Thr | Arg | Ala | Gln | Arg | Val | Arg | Ala |
| | | | | 85 | | | | | 90 | | | | | 95 | |
| Ala | Met | Phe | Pro | Glu | Thr | Leu | Asp | Glu | Gly | Met | Gln | Ile | Pro | Ser | Thr |
| | | | 100 | | | | | 105 | | | | | 110 | | |
| Gln | Phe | Asp | Ala | Ala | His | Pro | Thr | Asn | Val | Gln | Arg | Leu | Ala | Glu | Pro |
| | | | 115 | | | | | 120 | | | | | 125 | | |
| Ser | Gln | Met | Leu | Lys | His | Ala | Val | Val | Asn | Leu | Ile | Asn | Tyr | Gln | Asp |
| | 130 | | | | | 135 | | | | | 140 | | | | |
| Asp | Ala | Glu | Leu | Ala | Thr | Arg | Ala | Ile | Pro | Glu | Leu | Thr | Lys | Leu | Leu |
| 145 | | | | | 150 | | | | | 155 | | | | | 160 |
| Asn | Asp | Glu | Asp | Gln | Val | Val | Val | Asn | Lys | Ala | Ala | Val | Met | Val | His |
| | | | | 165 | | | | | 170 | | | | | 175 | |
| Gln | Leu | Ser | Lys | Lys | Glu | Ala | Ser | Arg | His | Ala | Ile | Met | Arg | Ser | Pro |
| | | | 180 | | | | | 185 | | | | | 190 | | |
| Gln | Met | Val | Ser | Ala | Ile | Val | Arg | Thr | Met | Gln | Asn | Thr | Asn | Asp | Val |
| | | | 195 | | | | | 200 | | | | | 205 | | |
| Glu | Thr | Ala | Arg | Cys | Thr | Ala | Gly | Thr | Leu | His | Asn | Leu | Ser | His | His |
| | 210 | | | | | 215 | | | | | 220 | | | | |
| Arg | Glu | Gly | Leu | Leu | Ala | Ile | Phe | Lys | Ser | Gly | Gly | Ile | Pro | Ala | Leu |
| 225 | | | | | 230 | | | | | 235 | | | | | 240 |
| Val | Lys | Met | Leu | Gly | Ser | Pro | Val | Asp | Ser | Val | Leu | Phe | Tyr | Ala | Ile |
| | | | | 245 | | | | | 250 | | | | | 255 | |
| Thr | Thr | Leu | His | Asn | Leu | Leu | Leu | His | Gln | Glu | Gly | Ala | Lys | Met | Ala |
| | | | 260 | | | | | 265 | | | | | 270 | | |
| Val | Arg | Leu | Ala | Gly | Gly | Leu | Gln | Lys | Met | Val | Ala | Leu | Leu | Asn | Lys |
| | | | 275 | | | | | 280 | | | | | 285 | | |
| Thr | Asn | Val | Lys | Phe | Leu | Ala | Ile | Thr | Thr | Asp | Cys | Leu | Gln | Ile | Leu |
| | 290 | | | | | 295 | | | | | 300 | | | | |
| Ala | Tyr | Gly | Asn | Gln | Glu | Ser | Lys | Leu | Ile | Ile | Leu | Ala | Ser | Gly | Gly |
| 305 | | | | | 310 | | | | | 315 | | | | | 320 |
| Pro | Gln | Ala | Leu | Val | Asn | Ile | Met | Arg | Thr | Tyr | Thr | Tyr | Glu | Lys | Leu |
| | | | | 325 | | | | | 330 | | | | | 335 | |
| Leu | Trp | Thr | Thr | Ser | Arg | Val | Leu | Lys | Val | Leu | Ser | Val | Cys | Ser | Ser |
| | | | 340 | | | | | 345 | | | | | 350 | | |
| Asn | Lys | Pro | Ala | Ile | Val | Glu | Ala | Gly | Gly | Met | Gln | Ala | Leu | Gly | Leu |
| | | | 355 | | | | | 360 | | | | | 365 | | |

```
His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
                435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
                500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
    610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
                660                 665                 670

Arg Leu Ser Val Glu Leu Thr Ser Ser Leu Phe Arg Thr Glu Pro Met
            675                 680                 685

Ala Trp Asn Glu Thr Ala Asp Leu Gly Leu Asp Ile Gly Ala Gln Gly
    690                 695                 700

Glu Pro Leu Gly Tyr Arg Gln Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
                740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
770                 775                 780
```

<210> SEQ ID NO 3
<211> LENGTH: 1515
<212> TYPE: DNA
<213> ORGANISM: Homo sapiens
<220> FEATURE:
<221> NAME/KEY: CDS
<222> LOCATION: (1)...(1515)
<223> OTHER INFORMATION: Coding sequence for human YAP1 isoform 1

<400> SEQUENCE: 3

```
atg gat ccc ggg cag cag ccg ccg cct caa ccg gcc ccc cag ggc caa      48
Met Asp Pro Gly Gln Gln Pro Pro Gln Pro Ala Pro Gln Gly Gln
  1               5                  10                  15 ggg cag ccg cct tcg cag ccc ccg cag ggg cag ggc ccg ccg tcc gga      96
Gly Gln Pro Pro Ser Gln Pro Pro Gln Gly Gln Gly Pro Pro Ser Gly
             20                  25                  30 ccc ggg caa ccg gca ccc gcg gcg acc cag gcg gcg ccg cag gca ccc     144
Pro Gly Gln Pro Ala Pro Ala Ala Thr Gln Ala Ala Pro Gln Ala Pro
         35                  40                  45 ccc gcc ggg cat cag atc gtg cac gtc cgc ggg gac tcg gag acc gac     192
Pro Ala Gly His Gln Ile Val His Val Arg Gly Asp Ser Glu Thr Asp
 50                  55                  60 ctg gag gcg ctc ttc aac gcc gtc atg aac ccc aag acg gcc aac gtg     240
Leu Glu Ala Leu Phe Asn Ala Val Met Asn Pro Lys Thr Ala Asn Val
 65                  70                  75                  80 ccc cag acc gtg ccc atg agg ctc cgg aag ctg ccc gac tcc ttc ttc     288
Pro Gln Thr Val Pro Met Arg Leu Arg Lys Leu Pro Asp Ser Phe Phe
                 85                  90                  95 aag ccg ccg gag ccc aaa tcc cac tcc cga cag gcc agt act gat gca     336
Lys Pro Pro Glu Pro Lys Ser His Ser Arg Gln Ala Ser Thr Asp Ala
            100                 105                 110 ggc act gca gga gcc ctg act cca cag cat gtt cga gct cat tcc tct     384
Gly Thr Ala Gly Ala Leu Thr Pro Gln His Val Arg Ala His Ser Ser
        115                 120                 125 cca gct tct ctg cag ttg gga gct gtt tct cct ggg aca ctg acc ccc     432
Pro Ala Ser Leu Gln Leu Gly Ala Val Ser Pro Gly Thr Leu Thr Pro
    130                 135                 140 act gga gta gtc tct ggc cca gca gct aca ccc aca gct cag cat ctt     480
Thr Gly Val Val Ser Gly Pro Ala Ala Thr Pro Thr Ala Gln His Leu
145                 150                 155                 160 cga cag tct tct ttt gag ata cct gat gat gta cct ctg cca gca ggt     528
Arg Gln Ser Ser Phe Glu Ile Pro Asp Asp Val Pro Leu Pro Ala Gly
                165                 170                 175 tgg gag atg gca aag aca tct tct ggt cag aga tac ttc tta aat cac     576
Trp Glu Met Ala Lys Thr Ser Ser Gly Gln Arg Tyr Phe Leu Asn His
            180                 185                 190 atc gat cag aca aca aca tgg cag gac ccc agg aag gcc atg ctg tcc     624
Ile Asp Gln Thr Thr Thr Trp Gln Asp Pro Arg Lys Ala Met Leu Ser
        195                 200                 205 cag atg aac gtc aca gcc ccc acc agt cca cca gtg cag cag aat atg     672
Gln Met Asn Val Thr Ala Pro Thr Ser Pro Pro Val Gln Gln Asn Met
    210                 215                 220 atg aac tcg gct tca ggt cct ctt cct gat gga tgg gaa caa gcc atg     720
Met Asn Ser Ala Ser Gly Pro Leu Pro Asp Gly Trp Glu Gln Ala Met
225                 230                 235                 240 act cag gat gga gaa att tac tat ata aac cat aag aac aag acc acc     768
Thr Gln Asp Gly Glu Ile Tyr Tyr Ile Asn His Lys Asn Lys Thr Thr
                245                 250                 255 tct tgg cta gac cca agg ctt gac cct cgt ttt gcc atg aac cag aga     816
Ser Trp Leu Asp Pro Arg Leu Asp Pro Arg Phe Ala Met Asn Gln Arg
            260                 265                 270
```

-continued

| | |
|---|---|
| atc agt cag agt gct cca gtg aaa cag cca cca ccc ctg gct ccc cag<br>Ile Ser Gln Ser Ala Pro Val Lys Gln Pro Pro Pro Leu Ala Pro Gln<br>    275                              280                        285 | 864 |
| agc cca cag gga ggc gtc atg ggt ggc agc aac tcc aac cag cag caa<br>Ser Pro Gln Gly Gly Val Met Gly Gly Ser Asn Ser Asn Gln Gln Gln<br>    290                              295                        300 | 912 |
| cag atg cga ctg cag caa ctg cag atg gag aag gag agg ctg cgg ctg<br>Gln Met Arg Leu Gln Gln Leu Gln Met Glu Lys Glu Arg Leu Arg Leu<br>305                            310                        315                        320 | 960 |
| aaa cag caa gaa ctg ctt cgg cag gca atg cgg aat atc aat ccc agc<br>Lys Gln Gln Glu Leu Leu Arg Gln Ala Met Arg Asn Ile Asn Pro Ser<br>                        325                        330                        335 | 1008 |
| aca gca aat tct cca aaa tgt cag gag tta gcc ctg cgt agc cag tta<br>Thr Ala Asn Ser Pro Lys Cys Gln Glu Leu Ala Leu Arg Ser Gln Leu<br>                        340                        345                        350 | 1056 |
| cca aca ctg gag cag gat ggt ggg act caa aat cca gtg tct tct ccc<br>Pro Thr Leu Glu Gln Asp Gly Gly Thr Gln Asn Pro Val Ser Ser Pro<br>                355                        360                        365 | 1104 |
| ggg atg tct cag gaa ttg aga aca atg acg acc aat agc tca gat cct<br>Gly Met Ser Gln Glu Leu Arg Thr Met Thr Thr Asn Ser Ser Asp Pro<br>370                            375                                      380 | 1152 |
| ttc ctt aac agt ggc acc tat cac tct cga gat gag agt aca gac agt<br>Phe Leu Asn Ser Gly Thr Tyr His Ser Arg Asp Glu Ser Thr Asp Ser<br>385                            390                        395                        400 | 1200 |
| gga cta agc atg agc agc tac agt gtc cct cga acc cca gat gac ttc<br>Gly Leu Ser Met Ser Ser Tyr Ser Val Pro Arg Thr Pro Asp Asp Phe<br>                        405                        410                        415 | 1248 |
| ctg aac agt gtg gat gag atg gat aca ggt gat act atc aac caa agc<br>Leu Asn Ser Val Asp Glu Met Asp Thr Gly Asp Thr Ile Asn Gln Ser<br>                        420                        425                        430 | 1296 |
| acc ctg ccc tca cag cag aac cgt ttc cca gac tac ctt gaa gcc att<br>Thr Leu Pro Ser Gln Gln Asn Arg Phe Pro Asp Tyr Leu Glu Ala Ile<br>                        435                        440                        445 | 1344 |
| cct ggg aca aat gtg gac ctt gga aca ctg gaa gga gat gga atg aac<br>Pro Gly Thr Asn Val Asp Leu Gly Thr Leu Glu Gly Asp Gly Met Asn<br>    450                              455                        460 | 1392 |
| ata gaa gga gag gag ctg atg cca agt ctg cag gaa gct ttg agt tct<br>Ile Glu Gly Glu Glu Leu Met Pro Ser Leu Gln Glu Ala Leu Ser Ser<br>465                            470                        475                        480 | 1440 |
| gac atc ctt aat gac atg gag tct gtt ttg gct gcc acc aag cta gat<br>Asp Ile Leu Asn Asp Met Glu Ser Val Leu Ala Ala Thr Lys Leu Asp<br>                        485                        490                        495 | 1488 |
| aaa gaa agc ttt ctt aca tgg tta tag<br>Lys Glu Ser Phe Leu Thr Trp Leu<br>            500 | 1515 |

<210> SEQ ID NO 4
<211> LENGTH: 504
<212> TYPE: PRT
<213> ORGANISM: Homo sapiens
<220> FEATURE:
<223> OTHER INFORMATION: Human YAP1 isoform 1

<400> SEQUENCE: 4

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
            35                  40                  45

```
Pro Ala Gly His Gln Ile Val His Val Arg Gly Asp Ser Glu Thr Asp
     50                  55                  60

Leu Glu Ala Leu Phe Asn Ala Val Met Asn Pro Lys Thr Ala Asn Val
 65                  70                  75                  80

Pro Gln Thr Val Pro Met Arg Leu Arg Lys Leu Pro Asp Ser Phe Phe
                 85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Val Gln Gln Asn Met
210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
            260                 265                 270

Ile Ser Gln Ser Ala Pro Val Lys Gln Pro Pro Leu Ala Pro Gln
        275                 280                 285

Ser Pro Gln Gly Gly Val Met Gly Gly Ser Asn Ser Asn Gln Gln Gln
290                 295                 300

Gln Met Arg Leu Gln Gln Leu Gln Met Glu Lys Glu Arg Leu Arg Leu
305                 310                 315                 320

Lys Gln Gln Glu Leu Leu Arg Gln Ala Met Arg Asn Ile Asn Pro Ser
                325                 330                 335

Thr Ala Asn Ser Pro Lys Cys Gln Glu Leu Ala Leu Arg Ser Gln Leu
            340                 345                 350

Pro Thr Leu Glu Gln Asp Gly Gly Thr Gln Asn Pro Val Ser Ser Pro
        355                 360                 365

Gly Met Ser Gln Glu Leu Arg Thr Met Thr Thr Asn Ser Ser Asp Pro
370                 375                 380

Phe Leu Asn Ser Gly Thr Tyr His Ser Arg Asp Glu Ser Thr Asp Ser
385                 390                 395                 400

Gly Leu Ser Met Ser Ser Tyr Ser Val Pro Arg Thr Pro Asp Asp Phe
                405                 410                 415

Leu Asn Ser Val Asp Glu Met Asp Thr Gly Asp Thr Ile Asn Gln Ser
            420                 425                 430

Thr Leu Pro Ser Gln Gln Asn Arg Phe Pro Asp Tyr Leu Glu Ala Ile
        435                 440                 445

Pro Gly Thr Asn Val Asp Leu Gly Thr Leu Glu Gly Asp Gly Met Asn
450                 455                 460

Ile Glu Gly Glu Glu Leu Met Pro Ser Leu Gln Glu Ala Leu Ser Ser
```

```
                465                 470                 475                 480
Asp Ile Leu Asn Asp Met Glu Ser Val Leu Ala Ala Thr Lys Leu Asp
                    485                 490                 495

Lys Glu Ser Phe Leu Thr Trp Leu
                500

<210> SEQ ID NO 5
<211> LENGTH: 1353
<212> TYPE: DNA
<213> ORGANISM: Homo sapiens
<220> FEATURE:
<221> NAME/KEY: CDS
<222> LOCATION: (1)...(1353)
<223> OTHER INFORMATION: Coding sequence for human YAP1 isoform 2

<400> SEQUENCE: 5 atg gat ccc ggg cag cag ccg ccg cct caa ccg gcc ccc cag ggc caa         48
Met Asp Pro Gly Gln Gln Pro Pro Pro Gln Pro Ala Pro Gln Gly Gln
  1               5                  10                  15 ggg cag ccg cct tcg cag ccc ccg cag ggg cag ggc ccg ccg tcc gga         96
Gly Gln Pro Pro Ser Gln Pro Pro Gln Gly Gln Gly Pro Pro Ser Gly
             20                  25                  30 ccc ggg caa ccg gca ccc gcg gcg acc cag gcg gcg ccg cag gca ccc        144
Pro Gly Gln Pro Ala Pro Ala Ala Thr Gln Ala Ala Pro Gln Ala Pro
         35                  40                  45 ccc gcc ggg cat cag atc gtg cac gtc cgc ggg gac tcg gag acc gac        192
Pro Ala Gly His Gln Ile Val His Val Arg Gly Asp Ser Glu Thr Asp
     50                  55                  60 ctg gag gcg ctc ttc aac gcc gtc atg aac ccc aag acg gcc aac gtg        240
Leu Glu Ala Leu Phe Asn Ala Val Met Asn Pro Lys Thr Ala Asn Val
 65                  70                  75                  80 ccc cag acc gtg ccc atg agg ctc cgg aag ctg ccc gac tcc ttc ttc        288
Pro Gln Thr Val Pro Met Arg Leu Arg Lys Leu Pro Asp Ser Phe Phe
                 85                  90                  95 aag ccg ccg gag ccc aaa tcc cac tcc cga cag gcc agt act gat gca        336
Lys Pro Pro Glu Pro Lys Ser His Ser Arg Gln Ala Ser Thr Asp Ala
            100                 105                 110 ggc act gca gga gcc ctg act cca cag cat gtt cga gct cat tcc tct        384
Gly Thr Ala Gly Ala Leu Thr Pro Gln His Val Arg Ala His Ser Ser
        115                 120                 125 cca gct tct ctg cag ttg gga gct gtt tct cct ggg aca ctg acc ccc        432
Pro Ala Ser Leu Gln Leu Gly Ala Val Ser Pro Gly Thr Leu Thr Pro
    130                 135                 140 act gga gta gtc tct ggc cca gca gct aca ccc aca gct cag cat ctt        480
Thr Gly Val Val Ser Gly Pro Ala Ala Thr Pro Thr Ala Gln His Leu
145                 150                 155                 160 cga cag tct tct ttt gag ata cct gat gat gta cct ctg cca gca ggt        528
Arg Gln Ser Ser Phe Glu Ile Pro Asp Asp Val Pro Leu Pro Ala Gly
                165                 170                 175 tgg gag atg gca aag aca tct tct ggt cag aga tac ttc tta aat cac        576
Trp Glu Met Ala Lys Thr Ser Ser Gly Gln Arg Tyr Phe Leu Asn His
            180                 185                 190 atc gat cag aca aca aca tgg cag gac ccc agg aag gcc atg ctg tcc        624
Ile Asp Gln Thr Thr Thr Trp Gln Asp Pro Arg Lys Ala Met Leu Ser
        195                 200                 205 cag atg aac gtc aca gcc ccc acc agt cca cca gtg cag cag aat atg        672
Gln Met Asn Val Thr Ala Pro Thr Ser Pro Pro Val Gln Gln Asn Met
    210                 215                 220 atg aac tcg gct tca gcc atg aac cag aga atc agt cag agt gct cca        720
Met Asn Ser Ala Ser Ala Met Asn Gln Arg Ile Ser Gln Ser Ala Pro
225                 230                 235                 240
```

-continued

| | | |
|---|---|---|
| gtg aaa cag cca cca ccc ctg gct ccc cag agc cca cag gga ggc gtc<br>Val Lys Gln Pro Pro Pro Leu Ala Pro Gln Ser Pro Gln Gly Gly Val<br>245 250 255 | | 768 |
| atg ggt ggc agc aac tcc aac cag cag caa cag atg cga ctg cag caa<br>Met Gly Gly Ser Asn Ser Asn Gln Gln Gln Gln Met Arg Leu Gln Gln<br>260 265 270 | | 816 |
| ctg cag atg gag aag gag agg ctg cgg ctg aaa cag caa gaa ctg ctt<br>Leu Gln Met Glu Lys Glu Arg Leu Arg Leu Lys Gln Gln Glu Leu Leu<br>275 280 285 | | 864 |
| cgg cag gag tta gcc ctg cgt agc cag tta cca aca ctg gag cag gat<br>Arg Gln Glu Leu Ala Leu Arg Ser Gln Leu Pro Thr Leu Glu Gln Asp<br>290 295 300 | | 912 |
| ggt ggg act caa aat cca gtg tct tct ccc ggg atg tct cag gaa ttg<br>Gly Gly Thr Gln Asn Pro Val Ser Ser Pro Gly Met Ser Gln Glu Leu<br>305 310 315 320 | | 960 |
| aga aca atg acg acc aat agc tca gat cct ttc ctt aac agt ggc acc<br>Arg Thr Met Thr Thr Asn Ser Ser Asp Pro Phe Leu Asn Ser Gly Thr<br>325 330 335 | | 1008 |
| tat cac tct cga gat gag agt aca gac agt gga cta agc atg agc agc<br>Tyr His Ser Arg Asp Glu Ser Thr Asp Ser Gly Leu Ser Met Ser Ser<br>340 345 350 | | 1056 |
| tac agt gtc cct cga acc cca gat gac ttc ctg aac agt gtg gat gag<br>Tyr Ser Val Pro Arg Thr Pro Asp Asp Phe Leu Asn Ser Val Asp Glu<br>355 360 365 | | 1104 |
| atg gat aca ggt gat act atc aac caa agc acc ctg ccc tca cag cag<br>Met Asp Thr Gly Asp Thr Ile Asn Gln Ser Thr Leu Pro Ser Gln Gln<br>370 375 380 | | 1152 |
| aac cgt ttc cca gac tac ctt gaa gcc att cct ggg aca aat gtg gac<br>Asn Arg Phe Pro Asp Tyr Leu Glu Ala Ile Pro Gly Thr Asn Val Asp<br>385 390 395 400 | | 1200 |
| ctt gga aca ctg gaa gga gat gga atg aac ata gaa gga gag gag ctg<br>Leu Gly Thr Leu Glu Gly Asp Gly Met Asn Ile Glu Gly Glu Glu Leu<br>405 410 415 | | 1248 |
| atg cca agt ctg cag gaa gct ttg agt tct gac atc ctt aat gac atg<br>Met Pro Ser Leu Gln Glu Ala Leu Ser Ser Asp Ile Leu Asn Asp Met<br>420 425 430 | | 1296 |
| gag tct gtt ttg gct gcc acc aag cta gat aaa gaa agc ttt ctt aca<br>Glu Ser Val Leu Ala Ala Thr Lys Leu Asp Lys Glu Ser Phe Leu Thr<br>435 440 445 | | 1344 |
| tgg tta tag<br>Trp Leu<br>450 | | 1353 |

<210> SEQ ID NO 6
<211> LENGTH: 450
<212> TYPE: PRT
<213> ORGANISM: Homo sapiens
<220> FEATURE:
<223> OTHER INFORMATION: Human YAP1 isoform 2

<400> SEQUENCE: 6

Met Asp Pro Gly Gln Gln Pro Pro Pro Gln Pro Ala Pro Gln Gly Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp Ser Glu Thr Asp
    50                  55                  60

```
Leu Glu Ala Leu Phe Asn Ala Val Met Asn Pro Lys Thr Ala Asn Val
 65                  70                  75                  80

Pro Gln Thr Val Pro Met Arg Leu Arg Lys Leu Pro Asp Ser Phe Phe
                 85                  90                  95

Lys Pro Pro Glu Pro Lys Ser His Ser Arg Gln Ala Ser Thr Asp Ala
            100                 105                 110

Gly Thr Ala Gly Ala Leu Thr Pro Gln His Val Arg Ala His Ser Ser
        115                 120                 125

Pro Ala Ser Leu Gln Leu Gly Ala Val Ser Pro Gly Thr Leu Thr Pro
    130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Glu Leu Ala Leu Arg Ser Gln Leu Pro Thr Leu Glu Gln Asp
    290                 295                 300

Gly Gly Thr Gln Asn Pro Val Ser Ser Pro Gly Met Ser Gln Glu Leu
305                 310                 315                 320

Arg Thr Met Thr Thr Asn Ser Ser Asp Pro Phe Leu Asn Ser Gly Thr
                325                 330                 335

Tyr His Ser Arg Asp Glu Ser Thr Asp Ser Gly Leu Ser Met Ser Ser
            340                 345                 350

Tyr Ser Val Pro Arg Thr Pro Asp Asp Phe Leu Asn Ser Val Asp Glu
        355                 360                 365

Met Asp Thr Gly Asp Thr Ile Asn Gln Ser Thr Leu Pro Ser Gln Gln
    370                 375                 380

Asn Arg Phe Pro Asp Tyr Leu Glu Ala Ile Pro Gly Thr Asn Val Asp
385                 390                 395                 400

Leu Gly Thr Leu Glu Gly Asp Gly Met Asn Ile Glu Gly Glu Glu Leu
                405                 410                 415

Met Pro Ser Leu Gln Glu Ala Leu Ser Ser Asp Ile Leu Asn Asp Met
            420                 425                 430

Glu Ser Val Leu Ala Ala Thr Lys Leu Asp Lys Glu Ser Phe Leu Thr
        435                 440                 445

Trp Leu
    450

<210> SEQ ID NO 7
<211> LENGTH: 2175
<212> TYPE: DNA
```

```
<213> ORGANISM: Homo sapiens
<220> FEATURE:
<221> NAME/KEY: CDS
<222> LOCATION: (1)...(2175)
<223> OTHER INFORMATION: Coding sequence for human GAB1 isoform a

<400> SEQUENCE: 7 atg agc ggt ggt gaa gtg gtc tgc tcc gga tgg ctc cgc aag tcc ccc      48
Met Ser Gly Gly Glu Val Val Cys Ser Gly Trp Leu Arg Lys Ser Pro
1               5                   10                  15 ccg gag aaa aag ttg aag cgt tat gca tgg aag agg aga tgg ttc gtg      96
Pro Glu Lys Lys Leu Lys Arg Tyr Ala Trp Lys Arg Arg Trp Phe Val
                20                  25                  30 tta cgc agt ggc cgt tta act gga gat cca gat gtt ttg gaa tat tac     144
Leu Arg Ser Gly Arg Leu Thr Gly Asp Pro Asp Val Leu Glu Tyr Tyr
            35                  40                  45 aaa aat gat cat gcc aag aag cct att cgt att att gat tta aat tta     192
Lys Asn Asp His Ala Lys Lys Pro Ile Arg Ile Ile Asp Leu Asn Leu
        50                  55                  60 tgt caa caa gta gat gct gga ttg aca ttt aac aaa aaa gag ttt gaa     240
Cys Gln Gln Val Asp Ala Gly Leu Thr Phe Asn Lys Lys Glu Phe Glu
65                  70                  75                  80 aac agc tac att ttt gat atc aac act att gac cgg att ttc tac ttg     288
Asn Ser Tyr Ile Phe Asp Ile Asn Thr Ile Asp Arg Ile Phe Tyr Leu
                85                  90                  95 gta gca gac agc gag gag gag atg aat aag tgg gtt cgt tgt att tgt     336
Val Ala Asp Ser Glu Glu Glu Met Asn Lys Trp Val Arg Cys Ile Cys
                100                 105                 110 gac atc tgt ggg ttt aat cca aca gaa gaa gat cct gtg aag cca cct     384
Asp Ile Cys Gly Phe Asn Pro Thr Glu Glu Asp Pro Val Lys Pro Pro
            115                 120                 125 ggc agc tct tta caa gca cca gct gat tta cct tta gct ata aat aca     432
Gly Ser Ser Leu Gln Ala Pro Ala Asp Leu Pro Leu Ala Ile Asn Thr
        130                 135                 140 gca cca cca tcc acc cag gca gat tca tcc tct gct act cta cct cct     480
Ala Pro Pro Ser Thr Gln Ala Asp Ser Ser Ser Ala Thr Leu Pro Pro
145                 150                 155                 160 cca tat cag cta atc aat gtt cca cca cac ctg gaa act ctt ggc att     528
Pro Tyr Gln Leu Ile Asn Val Pro Pro His Leu Glu Thr Leu Gly Ile
                165                 170                 175 cag gag gat cct caa gac tac ctg ttg ctc atc aac tgt caa agc aag     576
Gln Glu Asp Pro Gln Asp Tyr Leu Leu Leu Ile Asn Cys Gln Ser Lys
                180                 185                 190 aag ccc gaa ccc acc aga acg cat gct gat tct gca aaa tcc acc tct     624
Lys Pro Glu Pro Thr Arg Thr His Ala Asp Ser Ala Lys Ser Thr Ser
            195                 200                 205 tct gaa aca gac tgc aat gat aac gtc cct tct cat aaa aat cct gct     672
Ser Glu Thr Asp Cys Asn Asp Asn Val Pro Ser His Lys Asn Pro Ala
        210                 215                 220 tcc tcc cag agc aaa cat gga atg aat ggc ttt ttt cag cag caa atg     720
Ser Ser Gln Ser Lys His Gly Met Asn Gly Phe Phe Gln Gln Gln Met
225                 230                 235                 240 ata tac gac tct cca cct tca cgt gcc cca tct gct tca gtt gac tcc     768
Ile Tyr Asp Ser Pro Pro Ser Arg Ala Pro Ser Ala Ser Val Asp Ser
                245                 250                 255 agc ctt tat aac ctg ccc agg agt tat tcc cat gat gtt tta cca aag     816
Ser Leu Tyr Asn Leu Pro Arg Ser Tyr Ser His Asp Val Leu Pro Lys
                260                 265                 270 gtg tct cca tca agt act gaa gca gat gga gaa ctc tat gtt ttt aat     864
Val Ser Pro Ser Ser Thr Glu Ala Asp Gly Glu Leu Tyr Val Phe Asn
            275                 280                 285
```

-continued

```
acc cca tct ggg aca tcg agt gta gag act caa atg agg cat gta tct    912
Thr Pro Ser Gly Thr Ser Ser Val Glu Thr Gln Met Arg His Val Ser
    290             295                 300 att agt tat gac att cct cca aca cct ggt aat act tat cag att cca    960
Ile Ser Tyr Asp Ile Pro Pro Thr Pro Gly Asn Thr Tyr Gln Ile Pro
305             310                 315                 320 cga aca ttt cca gaa gga acc ttg gga cag aca tca aag cta gac act   1008
Arg Thr Phe Pro Glu Gly Thr Leu Gly Gln Thr Ser Lys Leu Asp Thr
                325                 330                 335 att cca gat att cct cca cct cgg cca ccg aaa cca cat cca gct cat   1056
Ile Pro Asp Ile Pro Pro Pro Arg Pro Pro Lys Pro His Pro Ala His
            340                 345                 350 gac cga tct cct gtg gaa acg tgt agt atc cca cgc acc gcc tca gac   1104
Asp Arg Ser Pro Val Glu Thr Cys Ser Ile Pro Arg Thr Ala Ser Asp
        355                 360                 365 act gac agt agt tac tgt atc cct aca gca ggg atg tcg cct tca cgt   1152
Thr Asp Ser Ser Tyr Cys Ile Pro Thr Ala Gly Met Ser Pro Ser Arg
    370                 375                 380 agt aat acc att tcc act gtg gat tta aac aaa ttg cga aaa gat gct   1200
Ser Asn Thr Ile Ser Thr Val Asp Leu Asn Lys Leu Arg Lys Asp Ala
385             390                 395                 400 agt tct caa gac tgc tat gat att cca cga gca ttt cca agt gat aga   1248
Ser Ser Gln Asp Cys Tyr Asp Ile Pro Arg Ala Phe Pro Ser Asp Arg
                405                 410                 415 tct agt tca ctt gaa ggc ttc cat aac cac ttt aaa gtc aaa aat gtg   1296
Ser Ser Ser Leu Glu Gly Phe His Asn His Phe Lys Val Lys Asn Val
            420                 425                 430 ttg aca gtg gga agt gtt tca agt gaa gaa ctg gat gaa aat tac gtc   1344
Leu Thr Val Gly Ser Val Ser Ser Glu Glu Leu Asp Glu Asn Tyr Val
        435                 440                 445 cca atg aat ccc aat tca cca cga caa cat tcc agc agt ttt aca       1392
Pro Met Asn Pro Asn Ser Pro Pro Arg Gln His Ser Ser Ser Phe Thr
    450                 455                 460 gaa cca att cag gaa gca aat tat gtg cca atg act cca gga aca ttt   1440
Glu Pro Ile Gln Glu Ala Asn Tyr Val Pro Met Thr Pro Gly Thr Phe
465             470                 475                 480 gat ttt tcc tca ttt gga atg caa gtt cct cct cct gct cat atg ggc   1488
Asp Phe Ser Ser Phe Gly Met Gln Val Pro Pro Pro Ala His Met Gly
                485                 490                 495 ttc agg tcc agc cca aaa acc cct ccc aga agg cca gtt cct gtt gca   1536
Phe Arg Ser Ser Pro Lys Thr Pro Pro Arg Arg Pro Val Pro Val Ala
            500                 505                 510 gac tgt gaa cca ccc ccc gtg gat agg aac ctc aag cca gac aga aaa   1584
Asp Cys Glu Pro Pro Pro Val Asp Arg Asn Leu Lys Pro Asp Arg Lys
        515                 520                 525 ggt caa agt cct aaa att tta aga ctc aaa ccc cat ggt tta gag cga   1632
Gly Gln Ser Pro Lys Ile Leu Arg Leu Lys Pro His Gly Leu Glu Arg
    530                 535                 540 act gat tca caa acc ata ggt gac ttt gct aca aga aga aag gtc aag   1680
Thr Asp Ser Gln Thr Ile Gly Asp Phe Ala Thr Arg Arg Lys Val Lys
545             550                 555                 560 cca gcg cct tta gaa ata aaa cct ttg cca gaa tgg gaa gaa tta caa   1728
Pro Ala Pro Leu Glu Ile Lys Pro Leu Pro Glu Trp Glu Glu Leu Gln
                565                 570                 575 gcc cca gtt aga tct ccc atc act agg agt ttt gct cga gac tct tcc   1776
Ala Pro Val Arg Ser Pro Ile Thr Arg Ser Phe Ala Arg Asp Ser Ser
            580                 585                 590 agg ttt ccc atg tcc ccc cga cca gat tca gtg cat agc aca act tca   1824
Arg Phe Pro Met Ser Pro Arg Pro Asp Ser Val His Ser Thr Thr Ser
```

-continued

```
                  595                 600                 605
agc agt gac tca cac gac agt gaa gag aat tat gtt ccc atg aac cca    1872
Ser Ser Asp Ser His Asp Ser Glu Glu Asn Tyr Val Pro Met Asn Pro
    610                 615                 620 aac ctg tcc agt gaa gac cca aat ctc ttt ggc agt aac agt ctt gat    1920
Asn Leu Ser Ser Glu Asp Pro Asn Leu Phe Gly Ser Asn Ser Leu Asp
625                 630                 635                 640 gga gga agc agc cct atg atc aag ccc aaa gga gac aaa cag gtg gaa    1968
Gly Gly Ser Ser Pro Met Ile Lys Pro Lys Gly Asp Lys Gln Val Glu
            645                 650                 655 tac tta gat ctc gac tta gat tct ggg aaa tcc aca cca cca cgt aag    2016
Tyr Leu Asp Leu Asp Leu Asp Ser Gly Lys Ser Thr Pro Pro Arg Lys
        660                 665                 670 caa aag agc agt ggc tca ggc agc agt gta gca gat gag aga gtg gat    2064
Gln Lys Ser Ser Gly Ser Gly Ser Ser Val Ala Asp Glu Arg Val Asp
    675                 680                 685 tat gtt gtt gtt gac caa cag aag acc ttg gct cta aag agt acc cgg    2112
Tyr Val Val Val Asp Gln Gln Lys Thr Leu Ala Leu Lys Ser Thr Arg
690                 695                 700 gaa gcc tgg aca gat ggg aga cag tcc aca gaa tca gaa acg cca gcg    2160
Glu Ala Trp Thr Asp Gly Arg Gln Ser Thr Glu Ser Glu Thr Pro Ala
705                 710                 715                 720 aag agt gtg aaa tga                                                2175
Lys Ser Val Lys <210> SEQ ID NO 8
<211> LENGTH: 724
<212> TYPE: PRT
<213> ORGANISM: Homo sapiens
<220> FEATURE:
<223> OTHER INFORMATION: Human GAB1 isoform a

<400> SEQUENCE: 8

Met Ser Gly Gly Glu Val Val Cys Ser Gly Trp Leu Arg Lys Ser Pro
1               5                   10                  15

Pro Glu Lys Lys Leu Lys Arg Tyr Ala Trp Lys Arg Arg Trp Phe Val
            20                  25                  30

Leu Arg Ser Gly Arg Leu Thr Gly Asp Pro Asp Val Leu Glu Tyr Tyr
        35                  40                  45

Lys Asn Asp His Ala Lys Lys Pro Ile Arg Ile Ile Asp Leu Asn Leu
    50                  55                  60

Cys Gln Gln Val Asp Ala Gly Leu Thr Phe Asn Lys Lys Glu Phe Glu
65                  70                  75                  80

Asn Ser Tyr Ile Phe Asp Ile Asn Thr Ile Asp Arg Ile Phe Tyr Leu
                85                  90                  95

Val Ala Asp Ser Glu Glu Glu Met Asn Lys Trp Val Arg Cys Ile Cys
            100                 105                 110

Asp Ile Cys Gly Phe Asn Pro Thr Glu Glu Asp Pro Val Lys Pro Pro
        115                 120                 125

Gly Ser Ser Leu Gln Ala Pro Ala Asp Leu Pro Leu Ala Ile Asn Thr
    130                 135                 140

Ala Pro Pro Ser Thr Gln Ala Asp Ser Ser Ala Thr Leu Pro Pro
145                 150                 155                 160

Pro Tyr Gln Leu Ile Asn Val Pro Pro His Leu Glu Thr Leu Gly Ile
                165                 170                 175

Gln Glu Asp Pro Gln Asp Tyr Leu Leu Leu Ile Asn Cys Gln Ser Lys
            180                 185                 190
```

```
Lys Pro Glu Pro Thr Arg Thr His Ala Asp Ser Ala Lys Ser Thr Ser
            195                 200                 205

Ser Glu Thr Asp Cys Asn Asp Asn Val Pro Ser His Lys Asn Pro Ala
210                 215                 220

Ser Ser Gln Ser Lys His Gly Met Asn Gly Phe Phe Gln Gln Gln Met
225                 230                 235                 240

Ile Tyr Asp Ser Pro Pro Ser Arg Ala Pro Ser Ala Ser Val Asp Ser
                245                 250                 255

Ser Leu Tyr Asn Leu Pro Arg Ser Tyr Ser His Asp Val Leu Pro Lys
            260                 265                 270

Val Ser Pro Ser Ser Thr Glu Ala Asp Gly Glu Leu Tyr Val Phe Asn
        275                 280                 285

Thr Pro Ser Gly Thr Ser Ser Val Glu Thr Gln Met Arg His Val Ser
    290                 295                 300

Ile Ser Tyr Asp Ile Pro Pro Thr Pro Gly Asn Thr Tyr Gln Ile Pro
305                 310                 315                 320

Arg Thr Phe Pro Glu Gly Thr Leu Gly Gln Thr Ser Lys Leu Asp Thr
                325                 330                 335

Ile Pro Asp Ile Pro Pro Arg Pro Pro Lys Pro His Pro Ala His
            340                 345                 350

Asp Arg Ser Pro Val Glu Thr Cys Ser Ile Pro Arg Thr Ala Ser Asp
        355                 360                 365

Thr Asp Ser Ser Tyr Cys Ile Pro Thr Ala Gly Met Ser Pro Ser Arg
    370                 375                 380

Ser Asn Thr Ile Ser Thr Val Asp Leu Asn Lys Leu Arg Lys Asp Ala
385                 390                 395                 400

Ser Ser Gln Asp Cys Tyr Asp Ile Pro Arg Ala Phe Pro Ser Asp Arg
                405                 410                 415

Ser Ser Ser Leu Glu Gly Phe His Asn His Phe Lys Val Lys Asn Val
            420                 425                 430

Leu Thr Val Gly Ser Val Ser Ser Glu Glu Leu Asp Glu Asn Tyr Val
        435                 440                 445

Pro Met Asn Pro Asn Ser Pro Pro Arg Gln His Ser Ser Ser Phe Thr
    450                 455                 460

Glu Pro Ile Gln Glu Ala Asn Tyr Val Pro Met Thr Pro Gly Thr Phe
465                 470                 475                 480

Asp Phe Ser Ser Phe Gly Met Gln Val Pro Pro Ala His Met Gly
                485                 490                 495

Phe Arg Ser Ser Pro Lys Thr Pro Pro Arg Arg Pro Val Pro Val Ala
            500                 505                 510

Asp Cys Glu Pro Pro Pro Val Asp Arg Asn Leu Lys Pro Asp Arg Lys
        515                 520                 525

Gly Gln Ser Pro Lys Ile Leu Arg Leu Lys Pro His Gly Leu Glu Arg
    530                 535                 540

Thr Asp Ser Gln Thr Ile Gly Asp Phe Ala Thr Arg Arg Lys Val Lys
545                 550                 555                 560

Pro Ala Pro Leu Glu Ile Lys Pro Leu Pro Glu Trp Glu Glu Leu Gln
                565                 570                 575

Ala Pro Val Arg Ser Pro Ile Thr Arg Ser Phe Ala Arg Asp Ser Ser
            580                 585                 590

Arg Phe Pro Met Ser Pro Arg Pro Asp Ser Val His Ser Thr Thr Ser
        595                 600                 605

Ser Ser Asp Ser His Asp Ser Glu Glu Asn Tyr Val Pro Met Asn Pro
```

|  |  |  | 610 |  |  |  | 615 |  |  |  | 620 |  |
|--|--|--|--|--|--|--|--|--|--|--|--|--|

Asn Leu Ser Ser Glu Asp Pro Asn Leu Phe Gly Ser Asn Ser Leu Asp
625                 630                 635                 640

Gly Gly Ser Ser Pro Met Ile Lys Pro Lys Gly Asp Lys Gln Val Glu
            645                 650                 655

Tyr Leu Asp Leu Asp Leu Asp Ser Gly Lys Ser Thr Pro Pro Arg Lys
            660                 665                 670

Gln Lys Ser Ser Gly Ser Gly Ser Ser Val Ala Asp Glu Arg Val Asp
            675                 680                 685

Tyr Val Val Val Asp Gln Gln Lys Thr Leu Ala Leu Lys Ser Thr Arg
            690                 695                 700

Glu Ala Trp Thr Asp Gly Arg Gln Ser Thr Glu Ser Glu Thr Pro Ala
705                 710                 715                 720

Lys Ser Val Lys

<210> SEQ ID NO 9
<211> LENGTH: 2085
<212> TYPE: DNA
<213> ORGANISM: Homo sapiens
<220> FEATURE:
<221> NAME/KEY: CDS
<222> LOCATION: (1)...(2085)
<223> OTHER INFORMATION: Coding sequence for human GAB1 isoform b

<400> SEQUENCE: 9

| atg agc ggt ggt gaa gtg gtc tgc tcc gga tgg ctc cgc aag tcc ccc | 48 |
|---|---|
| Met Ser Gly Gly Glu Val Val Cys Ser Gly Trp Leu Arg Lys Ser Pro | |
| 1               5                   10                  15 | |

| ccg gag aaa aag ttg aag cgt tat gca tgg aag agg aga tgg ttc gtg | 96 |
|---|---|
| Pro Glu Lys Lys Leu Lys Arg Tyr Ala Trp Lys Arg Arg Trp Phe Val | |
|             20                  25                  30 | |

| tta cgc agt ggc cgt tta act gga gat cca gat gtt ttg gaa tat tac | 144 |
|---|---|
| Leu Arg Ser Gly Arg Leu Thr Gly Asp Pro Asp Val Leu Glu Tyr Tyr | |
|         35                  40                  45 | |

| aaa aat gat cat gcc aag aag cct att cgt att att gat tta aat tta | 192 |
|---|---|
| Lys Asn Asp His Ala Lys Lys Pro Ile Arg Ile Ile Asp Leu Asn Leu | |
| 50                  55                  60 | |

| tgt caa caa gta gat gct gga ttg aca ttt aac aaa aaa gag ttt gaa | 240 |
|---|---|
| Cys Gln Gln Val Asp Ala Gly Leu Thr Phe Asn Lys Lys Glu Phe Glu | |
| 65                  70                  75                  80 | |

| aac agc tac att ttt gat atc aac act att gac cgg att ttc tac ttg | 288 |
|---|---|
| Asn Ser Tyr Ile Phe Asp Ile Asn Thr Ile Asp Arg Ile Phe Tyr Leu | |
|             85                  90                  95 | |

| gta gca gac agc gag gag gag atg aat aag tgg gtt cgt tgt att tgt | 336 |
|---|---|
| Val Ala Asp Ser Glu Glu Glu Met Asn Lys Trp Val Arg Cys Ile Cys | |
|             100                 105                 110 | |

| gac atc tgt ggg ttt aat cca aca gaa gaa gat cct gtg aag cca cct | 384 |
|---|---|
| Asp Ile Cys Gly Phe Asn Pro Thr Glu Glu Asp Pro Val Lys Pro Pro | |
|         115                 120                 125 | |

| ggc agc tct tta caa gca cca gct gat tta cct tta gct ata aat aca | 432 |
|---|---|
| Gly Ser Ser Leu Gln Ala Pro Ala Asp Leu Pro Leu Ala Ile Asn Thr | |
| 130                 135                 140 | |

| gca cca cca tcc acc cag gca gat tca tcc tct gct act cta cct cct | 480 |
|---|---|
| Ala Pro Pro Ser Thr Gln Ala Asp Ser Ser Ser Ala Thr Leu Pro Pro | |
| 145                 150                 155                 160 | |

| cca tat cag cta atc aat gtt cca cca cac ctg gaa act ctt ggc att | 528 |
|---|---|
| Pro Tyr Gln Leu Ile Asn Val Pro Pro His Leu Glu Thr Leu Gly Ile | |
|             165                 170                 175 | |

| cag gag gat cct caa gac tac ctg ttg ctc atc aac tgt caa agc aag | 576 |
|---|---|

```
        Gln Glu Asp Pro Gln Asp Tyr Leu Leu Leu Ile Asn Cys Gln Ser Lys
                    180                 185                 190 aag ccc gaa ccc acc aga acg cat gct gat tct gca aaa tcc acc tct       624
Lys Pro Glu Pro Thr Arg Thr His Ala Asp Ser Ala Lys Ser Thr Ser
            195                 200                 205 tct gaa aca gac tgc aat gat aac gtc cct tct cat aaa aat cct gct       672
Ser Glu Thr Asp Cys Asn Asp Asn Val Pro Ser His Lys Asn Pro Ala
210                 215                 220 tcc tcc cag agc aaa cat gga atg aat ggc ttt ttt cag cag caa atg       720
Ser Ser Gln Ser Lys His Gly Met Asn Gly Phe Phe Gln Gln Gln Met
225                 230                 235                 240 ata tac gac tct cca cct tca cgt gcc cca tct gct tca gtt gac tcc       768
Ile Tyr Asp Ser Pro Pro Ser Arg Ala Pro Ser Ala Ser Val Asp Ser
                245                 250                 255 agc ctt tat aac ctg ccc agg agt tat tcc cat gat gtt tta cca aag       816
Ser Leu Tyr Asn Leu Pro Arg Ser Tyr Ser His Asp Val Leu Pro Lys
            260                 265                 270 gtg tct cca tca agt act gaa gca gat gga gaa ctc tat gtt ttt aat       864
Val Ser Pro Ser Ser Thr Glu Ala Asp Gly Glu Leu Tyr Val Phe Asn
        275                 280                 285 acc cca tct ggg aca tcg agt gta gag act caa atg agg cat gta tct       912
Thr Pro Ser Gly Thr Ser Ser Val Glu Thr Gln Met Arg His Val Ser
    290                 295                 300 att agt tat gac att cct cca aca cct ggt aat act tat cag att cca       960
Ile Ser Tyr Asp Ile Pro Pro Thr Pro Gly Asn Thr Tyr Gln Ile Pro
305                 310                 315                 320 cga aca ttt cca gaa gga acc ttg gga cag aca tca aag cta gac act      1008
Arg Thr Phe Pro Glu Gly Thr Leu Gly Gln Thr Ser Lys Leu Asp Thr
                325                 330                 335 att cca gat att cct cca cct cgg cca ccg aaa cca cat cca gct cat      1056
Ile Pro Asp Ile Pro Pro Pro Arg Pro Pro Lys Pro His Pro Ala His
            340                 345                 350 gac cga tct cct gtg gaa acg tgt agt atc cca cgc acc gcc tca gac      1104
Asp Arg Ser Pro Val Glu Thr Cys Ser Ile Pro Arg Thr Ala Ser Asp
        355                 360                 365 act gac agt agt tac tgt atc cct aca gca ggg atg tcg cct tca cgt      1152
Thr Asp Ser Ser Tyr Cys Ile Pro Thr Ala Gly Met Ser Pro Ser Arg
    370                 375                 380 agt aat acc att tcc act gtg gat tta aac aaa ttg cga aaa gat gct      1200
Ser Asn Thr Ile Ser Thr Val Asp Leu Asn Lys Leu Arg Lys Asp Ala
385                 390                 395                 400 agt tct caa gac tgc tat gat att cca cga gca ttt cca agt gat aga      1248
Ser Ser Gln Asp Cys Tyr Asp Ile Pro Arg Ala Phe Pro Ser Asp Arg
                405                 410                 415 tct agt tca ctt gaa ggc ttc cat aac cac ttt aaa gtc aaa aat gtg      1296
Ser Ser Ser Leu Glu Gly Phe His Asn His Phe Lys Val Lys Asn Val
            420                 425                 430 ttg aca gtg gga agt gtt tca gtt gaa gaa ctg gat gaa aat tac gtc      1344
Leu Thr Val Gly Ser Val Ser Val Glu Glu Leu Asp Glu Asn Tyr Val
        435                 440                 445 cca atg aat ccc aat tca cca cca cga caa cat tcc agc agt ttt aca      1392
Pro Met Asn Pro Asn Ser Pro Pro Arg Gln His Ser Ser Ser Phe Thr
    450                 455                 460 gaa cca att cag gaa gca aat tat gtg cca atg act cca gga aca ttt      1440
Glu Pro Ile Gln Glu Ala Asn Tyr Val Pro Met Thr Pro Gly Thr Phe
465                 470                 475                 480 gat ttt tcc tca ttt gga atg caa gtt cct cct cct gct cat atg ggc      1488
Asp Phe Ser Ser Phe Gly Met Gln Val Pro Pro Pro Ala His Met Gly
                485                 490                 495
```

| | | | | | | | | | | | | | | |
|---|---|---|---|---|---|---|---|---|---|---|---|---|---|---|
| ttc | agg | tcc | agc | cca | aaa | acc | cct | ccc | aga | agg | cca | gtt | cct | gtt gca | 1536
| Phe | Arg | Ser | Ser | Pro | Lys | Thr | Pro | Pro | Arg | Arg | Pro | Val | Pro | Val Ala
| | | | 500 | | | | 505 | | | | | 510 | | |

```
ttc agg tcc agc cca aaa acc cct ccc aga agg cca gtt cct gtt gca      1536
Phe Arg Ser Ser Pro Lys Thr Pro Pro Arg Arg Pro Val Pro Val Ala
            500                 505                 510 gac tgt gaa cca ccc ccc gtg gat agg aac ctc aag cca gac aga aaa      1584
Asp Cys Glu Pro Pro Pro Val Asp Arg Asn Leu Lys Pro Asp Arg Lys
            515                 520                 525 gtc aag cca gcg cct tta gaa ata aaa cct ttg cca gaa tgg gaa gaa      1632
Val Lys Pro Ala Pro Leu Glu Ile Lys Pro Leu Pro Glu Trp Glu Glu
            530                 535                 540 tta caa gcc cca gtt aga tct ccc atc act agg agt ttt gct cga gac      1680
Leu Gln Ala Pro Val Arg Ser Pro Ile Thr Arg Ser Phe Ala Arg Asp
545                 550                 555                 560 tct tcc agg ttt ccc atg tcc ccc cga cca gat tca gtg cat agc aca      1728
Ser Ser Arg Phe Pro Met Ser Pro Arg Pro Asp Ser Val His Ser Thr
            565                 570                 575 act tca agc agt gac tca cac gac agt gaa gag aat tat gtt ccc atg      1776
Thr Ser Ser Ser Asp Ser His Asp Ser Glu Glu Asn Tyr Val Pro Met
            580                 585                 590 aac cca aac ctg tcc agt gaa gac cca aat ctc ttt ggc agt aac agt      1824
Asn Pro Asn Leu Ser Ser Glu Asp Pro Asn Leu Phe Gly Ser Asn Ser
            595                 600                 605 ctt gat gga gga agc agc cct atg atc aag ccc aaa gga gac aaa cag      1872
Leu Asp Gly Gly Ser Ser Pro Met Ile Lys Pro Lys Gly Asp Lys Gln
            610                 615                 620 gtg gaa tac tta gat ctc gac tta gat tct ggg aaa tcc aca cca cca      1920
Val Glu Tyr Leu Asp Leu Asp Leu Asp Ser Gly Lys Ser Thr Pro Pro
625                 630                 635                 640 cgt aag caa aag agc agt ggc tca ggc agc agt gta gca gat gag aga      1968
Arg Lys Gln Lys Ser Ser Gly Ser Gly Ser Ser Val Ala Asp Glu Arg
            645                 650                 655 gtg gat tat gtt gtt gtt gac caa cag aag acc ttg gct cta aag agt      2016
Val Asp Tyr Val Val Val Asp Gln Gln Lys Thr Leu Ala Leu Lys Ser
            660                 665                 670 acc cgg gaa gcc tgg aca gat ggg aga cag tcc aca gaa tca gaa acg      2064
Thr Arg Glu Ala Trp Thr Asp Gly Arg Gln Ser Thr Glu Ser Glu Thr
            675                 680                 685 cca gcg aag agt gtg aaa tga                                          2085
Pro Ala Lys Ser Val Lys
            690
```

<210> SEQ ID NO 10
<211> LENGTH: 694
<212> TYPE: PRT
<213> ORGANISM: Homo sapiens
<220> FEATURE:
<223> OTHER INFORMATION: Human GAB1 isoform b

<400> SEQUENCE: 10

```
Met Ser Gly Gly Glu Val Val Cys Ser Gly Trp Leu Arg Lys Ser Pro
1               5                   10                  15

Pro Glu Lys Lys Leu Lys Arg Tyr Ala Trp Lys Arg Arg Trp Phe Val
            20                  25                  30

Leu Arg Ser Gly Arg Leu Thr Gly Asp Pro Asp Val Leu Glu Tyr Tyr
        35                  40                  45

Lys Asn Asp His Ala Lys Lys Pro Ile Arg Ile Ile Asp Leu Asn Leu
    50                  55                  60

Cys Gln Gln Val Asp Ala Gly Leu Thr Phe Asn Lys Lys Glu Phe Glu
65                  70                  75                  80

Asn Ser Tyr Ile Phe Asp Ile Asn Thr Ile Asp Arg Ile Phe Tyr Leu
            85                  90                  95
```

```
Val Ala Asp Ser Glu Glu Met Asn Lys Trp Val Arg Cys Ile Cys
            100                 105                 110

Asp Ile Cys Gly Phe Asn Pro Thr Glu Glu Asp Pro Val Lys Pro Pro
            115                 120                 125

Gly Ser Ser Leu Gln Ala Pro Ala Asp Leu Pro Leu Ala Ile Asn Thr
130                 135                 140

Ala Pro Pro Ser Thr Gln Ala Asp Ser Ser Ala Thr Leu Pro Pro
145                 150                 155                 160

Pro Tyr Gln Leu Ile Asn Val Pro Pro His Leu Glu Thr Leu Gly Ile
                165                 170                 175

Gln Glu Asp Pro Gln Asp Tyr Leu Leu Leu Ile Asn Cys Gln Ser Lys
            180                 185                 190

Lys Pro Glu Pro Thr Arg Thr His Ala Asp Ser Ala Lys Ser Thr Ser
            195                 200                 205

Ser Glu Thr Asp Cys Asn Asp Asn Val Pro Ser His Lys Asn Pro Ala
    210                 215                 220

Ser Ser Gln Ser Lys His Gly Met Asn Gly Phe Gln Gln Gln Met
225                 230                 235                 240

Ile Tyr Asp Ser Pro Ser Arg Ala Pro Ser Ala Ser Val Asp Ser
                245                 250                 255

Ser Leu Tyr Asn Leu Pro Arg Ser Tyr Ser His Asp Val Leu Pro Lys
            260                 265                 270

Val Ser Pro Ser Ser Thr Glu Ala Asp Gly Glu Leu Tyr Val Phe Asn
    275                 280                 285

Thr Pro Ser Gly Thr Ser Ser Val Glu Thr Gln Met Arg His Val Ser
    290                 295                 300

Ile Ser Tyr Asp Ile Pro Pro Thr Pro Gly Asn Thr Tyr Gln Ile Pro
305                 310                 315                 320

Arg Thr Phe Pro Glu Gly Thr Leu Gly Gln Thr Ser Lys Leu Asp Thr
                325                 330                 335

Ile Pro Asp Ile Pro Pro Arg Pro Pro Lys Pro His Pro Ala His
            340                 345                 350

Asp Arg Ser Pro Val Glu Thr Cys Ser Ile Pro Arg Thr Ala Ser Asp
            355                 360                 365

Thr Asp Ser Ser Tyr Cys Ile Pro Thr Ala Gly Met Ser Pro Ser Arg
370                 375                 380

Ser Asn Thr Ile Ser Thr Val Asp Leu Asn Lys Leu Arg Lys Asp Ala
385                 390                 395                 400

Ser Ser Gln Asp Cys Tyr Asp Ile Pro Arg Ala Phe Pro Ser Asp Arg
            405                 410                 415

Ser Ser Ser Leu Glu Gly Phe His Asn His Phe Lys Val Lys Asn Val
            420                 425                 430

Leu Thr Val Gly Ser Val Ser Ser Glu Glu Leu Asp Glu Asn Tyr Val
            435                 440                 445

Pro Met Asn Pro Asn Ser Pro Pro Arg Gln His Ser Ser Ser Phe Thr
450                 455                 460

Glu Pro Ile Gln Glu Ala Asn Tyr Val Pro Met Thr Pro Gly Thr Phe
465                 470                 475                 480

Asp Phe Ser Ser Phe Gly Met Gln Val Pro Pro Ala His Met Gly
                485                 490                 495

Phe Arg Ser Ser Pro Lys Thr Pro Pro Arg Arg Pro Val Pro Val Ala
            500                 505                 510
```

-continued

```
Asp Cys Glu Pro Pro Val Asp Arg Asn Leu Lys Pro Asp Arg Lys
        515                 520                 525

Val Lys Pro Ala Pro Leu Glu Ile Lys Pro Leu Pro Glu Trp Glu Glu
530                 535                 540

Leu Gln Ala Pro Val Arg Ser Pro Ile Thr Arg Ser Phe Ala Arg Asp
545                 550                 555                 560

Ser Ser Arg Phe Pro Met Ser Pro Arg Pro Asp Ser Val His Ser Thr
                565                 570                 575

Thr Ser Ser Ser Asp Ser His Asp Ser Glu Glu Asn Tyr Val Pro Met
            580                 585                 590

Asn Pro Asn Leu Ser Ser Glu Asp Pro Asn Leu Phe Gly Ser Asn Ser
        595                 600                 605

Leu Asp Gly Gly Ser Ser Pro Met Ile Lys Pro Lys Gly Asp Lys Gln
    610                 615                 620

Val Glu Tyr Leu Asp Leu Asp Leu Asp Ser Gly Lys Ser Thr Pro Pro
625                 630                 635                 640

Arg Lys Gln Lys Ser Ser Gly Ser Gly Ser Ser Val Ala Asp Glu Arg
                645                 650                 655

Val Asp Tyr Val Val Val Asp Gln Gln Lys Thr Leu Ala Leu Lys Ser
            660                 665                 670

Thr Arg Glu Ala Trp Thr Asp Gly Arg Gln Ser Thr Glu Ser Glu Thr
        675                 680                 685

Pro Ala Lys Ser Val Lys
        690

<210> SEQ ID NO 11
<211> LENGTH: 7920
<212> TYPE: DNA
<213> ORGANISM: Homo sapiens
<220> FEATURE:
<221> NAME/KEY: CDS
<222> LOCATION: (1)...(7920)
<223> OTHER INFORMATION: Coding sequence for human filamin A isoform 1

<400> SEQUENCE: 11 atg agt agc tcc cac tct cgg gcg ggc cag agc gca gca ggc gcg gct      48
Met Ser Ser Ser His Ser Arg Ala Gly Gln Ser Ala Ala Gly Ala Ala
1               5                   10                  15 ccg ggc ggc ggc gtc gac acg cgg gac gcc gag atg ccg gcc acc gag      96
Pro Gly Gly Gly Val Asp Thr Arg Asp Ala Glu Met Pro Ala Thr Glu
                20                  25                  30 aag gac ctg gcg gag gac gcg ccg tgg aag aag atc cag cag aac act     144
Lys Asp Leu Ala Glu Asp Ala Pro Trp Lys Lys Ile Gln Gln Asn Thr
            35                  40                  45 ttc acg cgc tgg tgc aac gag cac ctg aag tgc gtg agc aag cgc atc     192
Phe Thr Arg Trp Cys Asn Glu His Leu Lys Cys Val Ser Lys Arg Ile
        50                  55                  60 gcc aac ctg cag acg gac ctg agc gac ggg ctg cgg ctt atc gcg ctg     240
Ala Asn Leu Gln Thr Asp Leu Ser Asp Gly Leu Arg Leu Ile Ala Leu
65                  70                  75                  80 ttg gag gtg ctc agc cag aag aag atg cac cgc aag cac aac cag cgg     288
Leu Glu Val Leu Ser Gln Lys Lys Met His Arg Lys His Asn Gln Arg
                85                  90                  95 ccc act ttc cgc caa atg cag ctt gag aac gtg tcg gtg gcg ctc gag     336
Pro Thr Phe Arg Gln Met Gln Leu Glu Asn Val Ser Val Ala Leu Glu
                100                 105                 110 ttc ctg gac cgc gag agc atc aaa ctg gtg tcc atc gac agc aag gcc     384
Phe Leu Asp Arg Glu Ser Ile Lys Leu Val Ser Ile Asp Ser Lys Ala
            115                 120                 125
```

| | | |
|---|---|---|
| atc gtg gac ggg aac ctg aag ctg atc ctg ggc ctc atc tgg acc ctg<br>Ile Val Asp Gly Asn Leu Lys Leu Ile Leu Gly Leu Ile Trp Thr Leu<br>130                        135                        140 | | 432 |
| atc ctg cac tac tcc atc tcc atg ccc atg tgg gac gag gag gag gat<br>Ile Leu His Tyr Ser Ile Ser Met Pro Met Trp Asp Glu Glu Glu Asp<br>145                    150                    155                    160 | | 480 |
| gag gag gcc aag aag cag acc ccc aag cag agg ctc ctg ggc tgg atc<br>Glu Glu Ala Lys Lys Gln Thr Pro Lys Gln Arg Leu Leu Gly Trp Ile<br>                    165                    170                    175 | | 528 |
| cag aac aag ctg ccg cag ctg ccc atc acc aac ttc agc cgg gac tgg<br>Gln Asn Lys Leu Pro Gln Leu Pro Ile Thr Asn Phe Ser Arg Asp Trp<br>                180                    185                    190 | | 576 |
| cag agc ggc cgg gcc ctg ggc gcc ctg gtg gac agc tgt gcc ccg ggc<br>Gln Ser Gly Arg Ala Leu Gly Ala Leu Val Asp Ser Cys Ala Pro Gly<br>            195                    200                    205 | | 624 |
| ctg tgt cct gac tgg gac tct tgg gac gcc agc aag ccc gtt acc aat<br>Leu Cys Pro Asp Trp Asp Ser Trp Asp Ala Ser Lys Pro Val Thr Asn<br>210                        215                    220 | | 672 |
| gcg cga gag gcc atg cag cag gcg gat gac tgg ctg ggc atc ccc cag<br>Ala Arg Glu Ala Met Gln Gln Ala Asp Asp Trp Leu Gly Ile Pro Gln<br>225                        230                    235                    240 | | 720 |
| gtg atc acc ccc gag gag att gtg gac ccc aac gtg gac gag cac tct<br>Val Ile Thr Pro Glu Glu Ile Val Asp Pro Asn Val Asp Glu His Ser<br>                        245                    250                    255 | | 768 |
| gtc atg acc tac ctg tcc cag ttc ccc aag gcc aag ctg aag cca ggg<br>Val Met Thr Tyr Leu Ser Gln Phe Pro Lys Ala Lys Leu Lys Pro Gly<br>        260                    265                    270 | | 816 |
| gct ccc ttg cgg ccc aaa ctg aac ccg aag aaa gcc cgt gcc tac ggg<br>Ala Pro Leu Arg Pro Lys Leu Asn Pro Lys Lys Ala Arg Ala Tyr Gly<br>275                        280                    285 | | 864 |
| cca ggc atc gag ccc aca ggc aac atg gtg aag aag cgg gca gag ttc<br>Pro Gly Ile Glu Pro Thr Gly Asn Met Val Lys Lys Arg Ala Glu Phe<br>        290                    295                    300 | | 912 |
| act gtg gag acc aga agt gct ggc cag gga gag gtg ctg gtg tac gtg<br>Thr Val Glu Thr Arg Ser Ala Gly Gln Gly Glu Val Leu Val Tyr Val<br>305                        310                    315                    320 | | 960 |
| gag gac ccg gcc gga cac cag gag gag gca aaa gtg acc gcc aat aac<br>Glu Asp Pro Ala Gly His Gln Glu Glu Ala Lys Val Thr Ala Asn Asn<br>                        325                    330                    335 | | 1008 |
| gac aag aac cgc acc ttc tcc gtc tgg tac gtc ccc gag gtg acg ggg<br>Asp Lys Asn Arg Thr Phe Ser Val Trp Tyr Val Pro Glu Val Thr Gly<br>                340                    345                    350 | | 1056 |
| act cat aag gtt act gtg ctc ttt gct ggc cag cac atc gcc aag agc<br>Thr His Lys Val Thr Val Leu Phe Ala Gly Gln His Ile Ala Lys Ser<br>        355                    360                    365 | | 1104 |
| ccc ttc gag gtg tac gtg gat aag tca cag ggt gac gcc agc aaa gtg<br>Pro Phe Glu Val Tyr Val Asp Lys Ser Gln Gly Asp Ala Ser Lys Val<br>370                        375                    380 | | 1152 |
| aca gcc caa ggt ccc ggc ctg gag ccc agt ggc aac atc gcc aac aag<br>Thr Ala Gln Gly Pro Gly Leu Glu Pro Ser Gly Asn Ile Ala Asn Lys<br>385                        390                    395                    400 | | 1200 |
| acc acc tac ttt gag atc ttt acg gca gga gct ggc acg ggc gag gtc<br>Thr Thr Tyr Phe Glu Ile Phe Thr Ala Gly Ala Gly Thr Gly Glu Val<br>                        405                    410                    415 | | 1248 |
| gag gtt gtg atc cag gac ccc atg gga cag aag ggc acg gta gag cct<br>Glu Val Val Ile Gln Asp Pro Met Gly Gln Lys Gly Thr Val Glu Pro<br>                420                    425                    430 | | 1296 |
| cag ctg gag gcc cgg ggc gac agc aca tac cgc tgc agc tac cag ccc<br>Gln Leu Glu Ala Arg Gly Asp Ser Thr Tyr Arg Cys Ser Tyr Gln Pro | | 1344 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     | 435 |     |     |     |     | 440 |     |     |     |     | 445 |     |     |
| acc | atg | gag | ggc | gtc | cac | acc | gtg | cac | gtc | acg | ttt | gcc | ggc | gtg | ccc | 1392 |
| Thr | Met | Glu | Gly | Val | His | Thr | Val | His | Val | Thr | Phe | Ala | Gly | Val | Pro |     |
|     | 450 |     |     |     |     | 455 |     |     |     |     | 460 |     |     |     |     |     |
| atc | cct | cgc | agc | ccc | tac | act | gtc | act | gtt | ggc | caa | gcc | tgt | aac | ccg | 1440 |
| Ile | Pro | Arg | Ser | Pro | Tyr | Thr | Val | Thr | Val | Gly | Gln | Ala | Cys | Asn | Pro |     |
| 465 |     |     |     |     | 470 |     |     |     |     | 475 |     |     |     |     | 480 |     |
| agt | gcc | tgc | cgg | gcg | gtt | ggc | cgg | ggc | ctc | cag | ccc | aag | ggt | gtg | cgg | 1488 |
| Ser | Ala | Cys | Arg | Ala | Val | Gly | Arg | Gly | Leu | Gln | Pro | Lys | Gly | Val | Arg |     |
|     |     |     |     | 485 |     |     |     |     | 490 |     |     |     |     | 495 |     |     |
| gtg | aag | gag | aca | gct | gac | ttc | aag | gtg | tac | aca | aag | ggc | gct | ggc | agt | 1536 |
| Val | Lys | Glu | Thr | Ala | Asp | Phe | Lys | Val | Tyr | Thr | Lys | Gly | Ala | Gly | Ser |     |
|     |     |     | 500 |     |     |     |     | 505 |     |     |     |     | 510 |     |     |     |
| ggg | gag | ctg | aag | gtc | acc | gtg | aag | ggc | ccc | aag | gga | gag | gag | cgc | gtg | 1584 |
| Gly | Glu | Leu | Lys | Val | Thr | Val | Lys | Gly | Pro | Lys | Gly | Glu | Glu | Arg | Val |     |
|     |     | 515 |     |     |     |     | 520 |     |     |     |     | 525 |     |     |     |     |
| aag | cag | aag | gac | ctg | ggg | gat | ggc | gtg | tat | ggc | ttc | gag | tat | tac | ccc | 1632 |
| Lys | Gln | Lys | Asp | Leu | Gly | Asp | Gly | Val | Tyr | Gly | Phe | Glu | Tyr | Tyr | Pro |     |
|     | 530 |     |     |     |     | 535 |     |     |     |     | 540 |     |     |     |     |     |
| atg | gtc | cct | gga | acc | tat | atc | gtc | acc | atc | acg | tgg | ggt | ggt | cag | aac | 1680 |
| Met | Val | Pro | Gly | Thr | Tyr | Ile | Val | Thr | Ile | Thr | Trp | Gly | Gly | Gln | Asn |     |
| 545 |     |     |     |     | 550 |     |     |     |     | 555 |     |     |     |     | 560 |     |
| atc | ggg | cgc | agt | ccc | ttc | gaa | gtg | aag | gtg | ggc | acc | gag | tgt | ggc | aat | 1728 |
| Ile | Gly | Arg | Ser | Pro | Phe | Glu | Val | Lys | Val | Gly | Thr | Glu | Cys | Gly | Asn |     |
|     |     |     |     | 565 |     |     |     |     | 570 |     |     |     |     | 575 |     |     |
| cag | aag | gta | cgg | gcc | tgg | ggc | cct | ggg | ctg | gag | ggc | ggc | gtc | gtt | ggc | 1776 |
| Gln | Lys | Val | Arg | Ala | Trp | Gly | Pro | Gly | Leu | Glu | Gly | Gly | Val | Val | Gly |     |
|     |     |     | 580 |     |     |     |     | 585 |     |     |     |     | 590 |     |     |     |
| aag | tca | gca | gac | ttt | gtg | gtg | gag | gct | atc | ggg | gac | gac | gtg | ggc | acg | 1824 |
| Lys | Ser | Ala | Asp | Phe | Val | Val | Glu | Ala | Ile | Gly | Asp | Asp | Val | Gly | Thr |     |
|     |     | 595 |     |     |     |     | 600 |     |     |     |     | 605 |     |     |     |     |
| ctg | ggc | ttc | tcg | gtg | gaa | ggg | cca | tcg | cag | gct | aag | atc | gaa | tgt | gac | 1872 |
| Leu | Gly | Phe | Ser | Val | Glu | Gly | Pro | Ser | Gln | Ala | Lys | Ile | Glu | Cys | Asp |     |
|     | 610 |     |     |     |     | 615 |     |     |     |     | 620 |     |     |     |     |     |
| gac | aag | ggc | gac | ggc | tcc | tgt | gat | gtg | cgc | tac | tgg | ccg | cag | gag | gct | 1920 |
| Asp | Lys | Gly | Asp | Gly | Ser | Cys | Asp | Val | Arg | Tyr | Trp | Pro | Gln | Glu | Ala |     |
| 625 |     |     |     |     | 630 |     |     |     |     | 635 |     |     |     |     | 640 |     |
| ggc | gag | tat | gcc | gtt | cac | gtg | ctg | tgc | aac | agc | gaa | gac | atc | cgc | ctc | 1968 |
| Gly | Glu | Tyr | Ala | Val | His | Val | Leu | Cys | Asn | Ser | Glu | Asp | Ile | Arg | Leu |     |
|     |     |     |     | 645 |     |     |     |     | 650 |     |     |     |     | 655 |     |     |
| agc | ccc | ttc | atg | gct | gac | atc | cgt | gac | gcg | ccc | cag | gac | ttc | cac | cca | 2016 |
| Ser | Pro | Phe | Met | Ala | Asp | Ile | Arg | Asp | Ala | Pro | Gln | Asp | Phe | His | Pro |     |
|     |     |     | 660 |     |     |     |     | 665 |     |     |     |     | 670 |     |     |     |
| gac | agg | gtg | aag | gca | cgt | ggg | cct | gga | ttg | gag | aag | aca | ggt | gtg | gcc | 2064 |
| Asp | Arg | Val | Lys | Ala | Arg | Gly | Pro | Gly | Leu | Glu | Lys | Thr | Gly | Val | Ala |     |
|     |     | 675 |     |     |     |     | 680 |     |     |     |     | 685 |     |     |     |     |
| gtc | aac | aag | cca | gca | gag | ttc | aca | gtg | gat | gcc | aag | cac | ggt | ggc | aag | 2112 |
| Val | Asn | Lys | Pro | Ala | Glu | Phe | Thr | Val | Asp | Ala | Lys | His | Gly | Gly | Lys |     |
|     | 690 |     |     |     |     | 695 |     |     |     |     | 700 |     |     |     |     |     |
| gcc | cca | ctt | cgg | gtc | caa | gtc | cag | gac | aat | gaa | ggc | tgc | cct | gtg | gag | 2160 |
| Ala | Pro | Leu | Arg | Val | Gln | Val | Gln | Asp | Asn | Glu | Gly | Cys | Pro | Val | Glu |     |
| 705 |     |     |     |     | 710 |     |     |     |     | 715 |     |     |     |     | 720 |     |
| gcg | ttg | gtc | aag | gac | aac | ggc | aat | ggc | act | tac | agc | tgc | tcc | tac | gtg | 2208 |
| Ala | Leu | Val | Lys | Asp | Asn | Gly | Asn | Gly | Thr | Tyr | Ser | Cys | Ser | Tyr | Val |     |
|     |     |     |     | 725 |     |     |     |     | 730 |     |     |     |     | 735 |     |     |
| ccc | agg | aag | ccg | gtg | aag | cac | aca | gcc | atg | gtg | tcc | tgg | gga | ggc | gtc | 2256 |
| Pro | Arg | Lys | Pro | Val | Lys | His | Thr | Ala | Met | Val | Ser | Trp | Gly | Gly | Val |     |
|     |     |     | 740 |     |     |     |     | 745 |     |     |     |     | 750 |     |     |     |
| agc | atc | ccc | aac | agc | ccc | ttc | agg | gtg | aat | gtg | gga | gct | ggc | agc | cac | 2304 |

```
Ser Ile Pro Asn Ser Pro Phe Arg Val Asn Val Gly Ala Gly Ser His
        755                 760                 765 ccc aac aag gtc aaa gta tac ggc ccc gga gta gcc aag aca ggg ctc    2352
Pro Asn Lys Val Lys Val Tyr Gly Pro Gly Val Ala Lys Thr Gly Leu
770                 775                 780 aag gcc cac gag ccc acc tac ttc act gtg gac tgc gcc gag gct ggc    2400
Lys Ala His Glu Pro Thr Tyr Phe Thr Val Asp Cys Ala Glu Ala Gly
785                 790                 795                 800 cag ggg gac gtc agc atc ggc atc aag tgt gcc cct gga gtg gta ggc    2448
Gln Gly Asp Val Ser Ile Gly Ile Lys Cys Ala Pro Gly Val Val Gly
                805                 810                 815 ccc gcc gaa gct gac atc gac ttc gac atc atc cgc aat gac aat gac    2496
Pro Ala Glu Ala Asp Ile Asp Phe Asp Ile Ile Arg Asn Asp Asn Asp
            820                 825                 830 acc ttc acg gtc aag tac acg ccc cgg ggg gct ggc agc tac acc att    2544
Thr Phe Thr Val Lys Tyr Thr Pro Arg Gly Ala Gly Ser Tyr Thr Ile
        835                 840                 845 atg gtc ctc ttt gct gac cag gcc acg ccc acc agc ccc atc cga gtc    2592
Met Val Leu Phe Ala Asp Gln Ala Thr Pro Thr Ser Pro Ile Arg Val
850                 855                 860 aag gtg gag ccc tct cat gac gcc agt aag gtg aag gcc gag ggc cct    2640
Lys Val Glu Pro Ser His Asp Ala Ser Lys Val Lys Ala Glu Gly Pro
865                 870                 875                 880 ggc ctc agt cgc act ggt gtc gag ctt ggc aag ccc acc cac ttc aca    2688
Gly Leu Ser Arg Thr Gly Val Glu Leu Gly Lys Pro Thr His Phe Thr
                885                 890                 895 gta aat gcc aaa gct gct ggc aaa ggc aag ctg gac gtc cag ttc tca    2736
Val Asn Ala Lys Ala Ala Gly Lys Gly Lys Leu Asp Val Gln Phe Ser
            900                 905                 910 gga ctc acc aag ggg gat gca gtg cga gat gtg gac atc atc gac cac    2784
Gly Leu Thr Lys Gly Asp Ala Val Arg Asp Val Asp Ile Ile Asp His
        915                 920                 925 cat gac aac acc tac aca gtc aag tac acg cct gtc cag cag ggt cca    2832
His Asp Asn Thr Tyr Thr Val Lys Tyr Thr Pro Val Gln Gln Gly Pro
930                 935                 940 gta ggc gtc aat gtc act tat gga ggg gat ccc atc cct aag agc cct    2880
Val Gly Val Asn Val Thr Tyr Gly Gly Asp Pro Ile Pro Lys Ser Pro
945                 950                 955                 960 ttc tca gtg gca gta tct cca agc ctg gac ctc agc aag atc aag gtg    2928
Phe Ser Val Ala Val Ser Pro Ser Leu Asp Leu Ser Lys Ile Lys Val
                965                 970                 975 tct ggc ctg gga gag aag gtg gac gtt ggc aaa gac cag gag ttc aca    2976
Ser Gly Leu Gly Glu Lys Val Asp Val Gly Lys Asp Gln Glu Phe Thr
            980                 985                 990 gtc aaa tca aag ggt gct ggt ggt caa ggc aaa gtg gca tcc aag att    3024
Val Lys Ser Lys Gly Ala Gly Gly Gln Gly Lys Val Ala Ser Lys Ile
        995                 1000                1005 gtg ggc ccc tcg ggt gca gcg gtg ccc tgc aag gtg gag cca ggc ctg    3072
Val Gly Pro Ser Gly Ala Ala Val Pro Cys Lys Val Glu Pro Gly Leu
1010                1015                1020 ggg gct gac aac agt gtg gtg cgc ttc ctg ccc cgt gag gaa ggg ccc    3120
Gly Ala Asp Asn Ser Val Val Arg Phe Leu Pro Arg Glu Glu Gly Pro
1025                1030                1035                1040 tat gag gtg gag gtg acc tat gac ggc gtg ccc gtg cct ggc agc ccc    3168
Tyr Glu Val Glu Val Thr Tyr Asp Gly Val Pro Val Pro Gly Ser Pro
                1045                1050                1055 ttt cct ctg gaa gct gtg gcc ccc acc aag cct agc aag gtg aag gcg    3216
Phe Pro Leu Glu Ala Val Ala Pro Thr Lys Pro Ser Lys Val Lys Ala
            1060                1065                1070
```

-continued

| | |
|---|---|
| ttt ggg ccg ggg ctg cag gga ggc agt gcg ggc tcc ccc gcc cgc ttc<br>Phe Gly Pro Gly Leu Gln Gly Gly Ser Ala Gly Ser Pro Ala Arg Phe<br>             1075                     1080                   1085 | 3264 |
| acc atc gac acc aag ggc gcc ggc aca ggt ggc ctg ggc ctg acg gtg<br>Thr Ile Asp Thr Lys Gly Ala Gly Thr Gly Gly Leu Gly Leu Thr Val<br>1090                     1095                     1100 | 3312 |
| gag ggc ccc tgt gag gcg cag ctc gag tgc ttg gac aat ggg gat ggc<br>Glu Gly Pro Cys Glu Ala Gln Leu Glu Cys Leu Asp Asn Gly Asp Gly<br>1105                     1110                     1115                   1120 | 3360 |
| aca tgt tcc gtg tcc tac gtg ccc acc gag ccc ggg gac tac aac atc<br>Thr Cys Ser Val Ser Tyr Val Pro Thr Glu Pro Gly Asp Tyr Asn Ile<br>             1125                     1130                     1135 | 3408 |
| aac atc ctc ttc gct gac acc cac atc cct ggc tcc cca ttc aag gcc<br>Asn Ile Leu Phe Ala Asp Thr His Ile Pro Gly Ser Pro Phe Lys Ala<br>1140                     1145                     1150 | 3456 |
| cac gtg gtt ccc tgc ttt gac gca tcc aaa gtc aag tgc tca ggc ccc<br>His Val Val Pro Cys Phe Asp Ala Ser Lys Val Lys Cys Ser Gly Pro<br>1155                     1160                     1165 | 3504 |
| ggg ctg gag cgg gcc acc gct ggg gag gtg ggc caa ttc caa gtg gac<br>Gly Leu Glu Arg Ala Thr Ala Gly Glu Val Gly Gln Phe Gln Val Asp<br>             1170                     1175                     1180 | 3552 |
| tgc tcg agc gcg ggc agc gcg gag ctg acc att gag atc tgc tcg gag<br>Cys Ser Ser Ala Gly Ser Ala Glu Leu Thr Ile Glu Ile Cys Ser Glu<br>1185                     1190                     1195                     1200 | 3600 |
| gcg ggg ctt ccg gcc gag gtg tac atc cag gac cac ggt gat ggc acg<br>Ala Gly Leu Pro Ala Glu Val Tyr Ile Gln Asp His Gly Asp Gly Thr<br>             1205                     1210                     1215 | 3648 |
| cac acc att acc tac att ccc ctc tgc ccc ggg gcc tac acc gtc acc<br>His Thr Ile Thr Tyr Ile Pro Leu Cys Pro Gly Ala Tyr Thr Val Thr<br>1220                     1225                     1230 | 3696 |
| atc aag tac ggc ggc cag ccc gtg ccc aac ttc ccc agc aag ctg cag<br>Ile Lys Tyr Gly Gly Gln Pro Val Pro Asn Phe Pro Ser Lys Leu Gln<br>             1235                     1240                     1245 | 3744 |
| gtg gaa cct gcg gtg gac act tcc ggt gtc cag tgc tat ggg cct ggt<br>Val Glu Pro Ala Val Asp Thr Ser Gly Val Gln Cys Tyr Gly Pro Gly<br>1250                     1255                     1260 | 3792 |
| att gag ggc cag ggt gtc ttc cgt gag gcc acc act gag ttc agt gtg<br>Ile Glu Gly Gln Gly Val Phe Arg Glu Ala Thr Thr Glu Phe Ser Val<br>1265                     1270                     1275                     1280 | 3840 |
| gac gcc cgg gct ctg aca cag acc gga ggg ccg cac gtc aag gcc cgt<br>Asp Ala Arg Ala Leu Thr Gln Thr Gly Gly Pro His Val Lys Ala Arg<br>             1285                     1290                     1295 | 3888 |
| gtg gcc aac ccc tca ggc aac ctg acg gag acc tac gtt cag gac cgt<br>Val Ala Asn Pro Ser Gly Asn Leu Thr Glu Thr Tyr Val Gln Asp Arg<br>1300                     1305                     1310 | 3936 |
| ggc gat ggc atg tac aaa gtg gag tac acg cct tac gag gag gga ctg<br>Gly Asp Gly Met Tyr Lys Val Glu Tyr Thr Pro Tyr Glu Glu Gly Leu<br>             1315                     1320                     1325 | 3984 |
| cac tcc gtg gac gtg acc tat gac ggc agt ccc gtg ccc agc agc ccc<br>His Ser Val Asp Val Thr Tyr Asp Gly Ser Pro Val Pro Ser Ser Pro<br>1330                     1335                     1340 | 4032 |
| ttc cag gtg ccc gtg acc gag ggc tgc gac ccc tcc cgg gtg cgt gtc<br>Phe Gln Val Pro Val Thr Glu Gly Cys Asp Pro Ser Arg Val Arg Val<br>1345                     1350                     1355                     1360 | 4080 |
| cac ggg cca ggc atc caa agt ggc acc acc aac aag ccc aac aag ttc<br>His Gly Pro Gly Ile Gln Ser Gly Thr Thr Asn Lys Pro Asn Lys Phe<br>             1365                     1370                     1375 | 4128 |
| act gtg gag acc agg gga gct ggc acg ggc ggc ctg ggc ctg gct gta<br>Thr Val Glu Thr Arg Gly Ala Gly Thr Gly Gly Leu Gly Leu Ala Val<br>1380                     1385                     1390 | 4176 |

```
gag ggc ccc tcc gag gcc aag atg tcc tgc atg gat aac aag gac ggc    4224
Glu Gly Pro Ser Glu Ala Lys Met Ser Cys Met Asp Asn Lys Asp Gly
        1395                1400                1405 agc tgc tcg gtc gag tac atc cct tat gag gct ggc acc tac agc ctc    4272
Ser Cys Ser Val Glu Tyr Ile Pro Tyr Glu Ala Gly Thr Tyr Ser Leu
    1410                1415                1420 aac gtc acc tat ggt ggc cat caa gtg cca ggc agt cct ttc aag gtc    4320
Asn Val Thr Tyr Gly Gly His Gln Val Pro Gly Ser Pro Phe Lys Val
1425                1430                1435                1440 cct gtg cat gat gtg aca gat gcg tcc aag gtc aag tgc tct ggg ccc    4368
Pro Val His Asp Val Thr Asp Ala Ser Lys Val Lys Cys Ser Gly Pro
                1445                1450                1455 ggc ctg agc cca ggc atg gtt cgt gcc aac ctc cct cag tcc ttc cag    4416
Gly Leu Ser Pro Gly Met Val Arg Ala Asn Leu Pro Gln Ser Phe Gln
            1460                1465                1470 gtg gac aca agc aag gct ggt gtg gcc cca ttg cag gtc aaa gtg caa    4464
Val Asp Thr Ser Lys Ala Gly Val Ala Pro Leu Gln Val Lys Val Gln
        1475                1480                1485 ggg ccc aaa ggc ctg gtg gag cca gtg gac gtg gta gac aac gct gat    4512
Gly Pro Lys Gly Leu Val Glu Pro Val Asp Val Val Asp Asn Ala Asp
    1490                1495                1500 ggc acc cag acc gtc aat tat gtg ccc agc cga gaa ggg ccc tac agc    4560
Gly Thr Gln Thr Val Asn Tyr Val Pro Ser Arg Glu Gly Pro Tyr Ser
1505                1510                1515                1520 atc tca gta ctg tat gga gat gaa gag gta ccc cgg agc ccc ttc aag    4608
Ile Ser Val Leu Tyr Gly Asp Glu Glu Val Pro Arg Ser Pro Phe Lys
                1525                1530                1535 gtc aag gtg ctg cct act cat gat gcc agc aag gtg aag gcc agt ggc    4656
Val Lys Val Leu Pro Thr His Asp Ala Ser Lys Val Lys Ala Ser Gly
            1540                1545                1550 ccc ggg ctc aac acc act ggc gtg cct gcc agc ctg ccc gtg gag ttc    4704
Pro Gly Leu Asn Thr Thr Gly Val Pro Ala Ser Leu Pro Val Glu Phe
        1555                1560                1565 acc atc gat gca aag gac gcc ggg gag ggc ctg ctg gct gtc cag atc    4752
Thr Ile Asp Ala Lys Asp Ala Gly Glu Gly Leu Leu Ala Val Gln Ile
    1570                1575                1580 acg gat ccc gaa ggc aag ccg aag aag aca cac atc caa gac aac cat    4800
Thr Asp Pro Glu Gly Lys Pro Lys Lys Thr His Ile Gln Asp Asn His
1585                1590                1595                1600 gac ggc acg tat aca gtg gcc tac gtg cca gac gtg aca ggt cgc tac    4848
Asp Gly Thr Tyr Thr Val Ala Tyr Val Pro Asp Val Thr Gly Arg Tyr
                1605                1610                1615 acc atc ctc atc aag tac ggt ggt gac gag atc ccc ttc tcc ccg tac    4896
Thr Ile Leu Ile Lys Tyr Gly Gly Asp Glu Ile Pro Phe Ser Pro Tyr
            1620                1625                1630 cgc gtg cgt gcc gtg ccc acc ggg gac gcc agc aag tgc act gtc aca    4944
Arg Val Arg Ala Val Pro Thr Gly Asp Ala Ser Lys Cys Thr Val Thr
        1635                1640                1645 ggt gct ggc atc ggc ccc acc att cag att ggg gag gag acg gtg atc    4992
Gly Ala Gly Ile Gly Pro Thr Ile Gln Ile Gly Glu Glu Thr Val Ile
    1650                1655                1660 act gtg gac act aag gcg gca ggc aaa ggc aaa gtg acg tgc acc gtg    5040
Thr Val Asp Thr Lys Ala Ala Gly Lys Gly Lys Val Thr Cys Thr Val
1665                1670                1675                1680 tgc acg cct gat ggc tca gag gtg gat gtg gac gtg gtg gag aat gag    5088
Cys Thr Pro Asp Gly Ser Glu Val Asp Val Asp Val Val Glu Asn Glu
                1685                1690                1695 gac ggc act ttc gac atc ttc tac acg gcc ccc cag ccg ggc aaa tac    5136
Asp Gly Thr Phe Asp Ile Phe Tyr Thr Ala Pro Gln Pro Gly Lys Tyr
```

| | | | | | | | | | | | | | | | | |
|---|---|---|---|---|---|---|---|---|---|---|---|---|---|---|---|---|
| | | | | 1700 | | | | 1705 | | | | 1710 | | | | |
| gtc | atc | tgt | gtg | cgc | ttt | ggt | ggc | gag | cac | gtg | ccc | aac | agc | ccc | ttc | 5184 |
| Val | Ile | Cys | Val | Arg | Phe | Gly | Gly | Glu | His | Val | Pro | Asn | Ser | Pro | Phe | |
| | 1715 | | | | | 1720 | | | | | 1725 | | | | | |
| caa | gtg | acg | gct | ctg | gct | ggg | gac | cag | ccc | tcg | gtg | cag | ccc | cct | cta | 5232 |
| Gln | Val | Thr | Ala | Leu | Ala | Gly | Asp | Gln | Pro | Ser | Val | Gln | Pro | Pro | Leu | |
| 1730 | | | | | 1735 | | | | | 1740 | | | | | | |
| cgg | tct | cag | cag | ctg | gcc | cca | cag | tac | acc | tac | gcc | cag | ggc | ggc | cag | 5280 |
| Arg | Ser | Gln | Gln | Leu | Ala | Pro | Gln | Tyr | Thr | Tyr | Ala | Gln | Gly | Gly | Gln | |
| 1745 | | | | 1750 | | | | | 1755 | | | | | 1760 | | |
| cag | act | tgg | gcc | ccg | gag | agg | ccc | ctg | gtg | ggt | gtc | aat | ggg | ctg | gat | 5328 |
| Gln | Thr | Trp | Ala | Pro | Glu | Arg | Pro | Leu | Val | Gly | Val | Asn | Gly | Leu | Asp | |
| | | | 1765 | | | | | 1770 | | | | | 1775 | | | |
| gtg | acc | agc | ctg | agg | ccc | ttt | gac | ctt | gtc | atc | ccc | ttc | acc | atc | aag | 5376 |
| Val | Thr | Ser | Leu | Arg | Pro | Phe | Asp | Leu | Val | Ile | Pro | Phe | Thr | Ile | Lys | |
| | | 1780 | | | | | 1785 | | | | | 1790 | | | | |
| aag | ggc | gag | atc | aca | ggg | gag | gtt | cgg | atg | ccc | tca | ggc | aag | gtg | gcg | 5424 |
| Lys | Gly | Glu | Ile | Thr | Gly | Glu | Val | Arg | Met | Pro | Ser | Gly | Lys | Val | Ala | |
| | 1795 | | | | | 1800 | | | | | 1805 | | | | | |
| cag | ccc | acc | atc | act | gac | aac | aaa | gac | ggc | acc | gtg | acc | gtg | cgg | tat | 5472 |
| Gln | Pro | Thr | Ile | Thr | Asp | Asn | Lys | Asp | Gly | Thr | Val | Thr | Val | Arg | Tyr | |
| 1810 | | | | | 1815 | | | | | 1820 | | | | | | |
| gca | ccc | agc | gag | gct | ggc | ctg | cac | gag | atg | gac | atc | cgc | tat | gac | aac | 5520 |
| Ala | Pro | Ser | Glu | Ala | Gly | Leu | His | Glu | Met | Asp | Ile | Arg | Tyr | Asp | Asn | |
| 1825 | | | | 1830 | | | | | 1835 | | | | | 1840 | | |
| atg | cac | atc | cca | gga | agc | ccc | ttg | cag | ttc | tat | gtg | gat | tac | gtc | aac | 5568 |
| Met | His | Ile | Pro | Gly | Ser | Pro | Leu | Gln | Phe | Tyr | Val | Asp | Tyr | Val | Asn | |
| | | | | 1845 | | | | | 1850 | | | | | 1855 | | |
| tgt | ggc | cat | gtc | act | gcc | tat | ggg | cct | ggc | ctc | acc | cat | gga | gta | gtg | 5616 |
| Cys | Gly | His | Val | Thr | Ala | Tyr | Gly | Pro | Gly | Leu | Thr | His | Gly | Val | Val | |
| | | | 1860 | | | | | 1865 | | | | | 1870 | | | |
| aac | aag | cct | gcc | acc | ttc | acc | gtc | aac | acc | aag | gat | gca | gga | gag | ggg | 5664 |
| Asn | Lys | Pro | Ala | Thr | Phe | Thr | Val | Asn | Thr | Lys | Asp | Ala | Gly | Glu | Gly | |
| | 1875 | | | | | 1880 | | | | | 1885 | | | | | |
| ggc | ctg | tct | ctg | gcc | att | gag | ggc | ccg | tcc | aaa | gca | gaa | atc | agc | tgc | 5712 |
| Gly | Leu | Ser | Leu | Ala | Ile | Glu | Gly | Pro | Ser | Lys | Ala | Glu | Ile | Ser | Cys | |
| 1890 | | | | | 1895 | | | | | 1900 | | | | | | |
| act | gac | aac | cag | gat | ggg | aca | tgc | agc | gtg | tcc | tac | ctg | cct | gtg | ctg | 5760 |
| Thr | Asp | Asn | Gln | Asp | Gly | Thr | Cys | Ser | Val | Ser | Tyr | Leu | Pro | Val | Leu | |
| 1905 | | | | 1910 | | | | | 1915 | | | | | 1920 | | |
| ccg | ggg | gac | tac | agc | att | cta | gtc | aag | tac | aat | gaa | cag | cac | gtc | cca | 5808 |
| Pro | Gly | Asp | Tyr | Ser | Ile | Leu | Val | Lys | Tyr | Asn | Glu | Gln | His | Val | Pro | |
| | | | | 1925 | | | | | 1930 | | | | | 1935 | | |
| ggc | agc | ccc | ttc | act | gct | cgg | gtc | aca | ggt | gac | gac | tcc | atg | cgt | atg | 5856 |
| Gly | Ser | Pro | Phe | Thr | Ala | Arg | Val | Thr | Gly | Asp | Asp | Ser | Met | Arg | Met | |
| | | | 1940 | | | | | 1945 | | | | | 1950 | | | |
| tcc | cac | cta | aag | gtc | ggc | tct | gct | gcc | gac | atc | ccc | atc | aac | atc | tca | 5904 |
| Ser | His | Leu | Lys | Val | Gly | Ser | Ala | Ala | Asp | Ile | Pro | Ile | Asn | Ile | Ser | |
| | 1955 | | | | | 1960 | | | | | 1965 | | | | | |
| gag | acg | gat | ctc | agc | ctg | ctg | acg | gcc | act | gtg | gtc | ccg | ccc | tcg | ggc | 5952 |
| Glu | Thr | Asp | Leu | Ser | Leu | Leu | Thr | Ala | Thr | Val | Val | Pro | Pro | Ser | Gly | |
| 1970 | | | | | 1975 | | | | | 1980 | | | | | | |
| cgg | gag | gag | ccc | tgt | ttg | ctg | aag | cgg | ctg | cgt | aat | ggc | cac | gtg | ggg | 6000 |
| Arg | Glu | Glu | Pro | Cys | Leu | Leu | Lys | Arg | Leu | Arg | Asn | Gly | His | Val | Gly | |
| 1985 | | | | 1990 | | | | | 1995 | | | | | 2000 | | |
| att | tca | ttc | gtg | ccc | aag | gag | acg | ggg | gag | cac | ctg | gtg | cat | gtg | aag | 6048 |
| Ile | Ser | Phe | Val | Pro | Lys | Glu | Thr | Gly | Glu | His | Leu | Val | His | Val | Lys | |
| | | | | 2005 | | | | | 2010 | | | | | 2015 | | |
| aaa | aat | ggc | cag | cac | gtg | gcc | agc | agc | ccc | atc | ccg | gtg | gtg | atc | agc | 6096 |

-continued

```
                     Lys Asn Gly Gln His Val Ala Ser Ser Pro Ile Pro Val Val Ile Ser
                                     2020                2025                2030 cag tcg gaa att ggg gat gcc agt cgt gtt cgg gtc tct ggt cag ggc         6144
Gln Ser Glu Ile Gly Asp Ala Ser Arg Val Arg Val Ser Gly Gln Gly
            2035                2040                2045 ctt cac gaa ggc cac acc ttt gag cct gca gag ttt atc att gat acc         6192
Leu His Glu Gly His Thr Phe Glu Pro Ala Glu Phe Ile Ile Asp Thr
    2050                2055                2060 cgc gat gca ggc tat ggt ggg ctc agc ctg tcc att gag ggc ccc agc         6240
Arg Asp Ala Gly Tyr Gly Gly Leu Ser Leu Ser Ile Glu Gly Pro Ser
2065                2070                2075                2080 aag gtg gac atc aac aca gag gac ctg gag gac ggg acg tgc agg gtc         6288
Lys Val Asp Ile Asn Thr Glu Asp Leu Glu Asp Gly Thr Cys Arg Val
                2085                2090                2095 acc tac tgc ccc aca gag cca ggc aac tac atc atc aac atc aag ttt         6336
Thr Tyr Cys Pro Thr Glu Pro Gly Asn Tyr Ile Ile Asn Ile Lys Phe
            2100                2105                2110 gcc gac cag cac gtg cct ggc agc ccc ttc tct gtg aag gtg aca ggc         6384
Ala Asp Gln His Val Pro Gly Ser Pro Phe Ser Val Lys Val Thr Gly
    2115                2120                2125 gag ggc cgg gtg aaa gag agc atc acc cgc agg cgt cgg gct cct tca         6432
Glu Gly Arg Val Lys Glu Ser Ile Thr Arg Arg Arg Ala Pro Ser
 2130                2135                2140 gtg gcc aac gtt ggt agt cat tgt gac ctc agc ctg aaa atc cct gaa         6480
Val Ala Asn Val Gly Ser His Cys Asp Leu Ser Leu Lys Ile Pro Glu
2145                2150                2155                2160 att agc atc cag gat atg aca gcc cag gtg acc agc cca tcg ggc aag         6528
Ile Ser Ile Gln Asp Met Thr Ala Gln Val Thr Ser Pro Ser Gly Lys
                2165                2170                2175 acc cat gag gcc gag atc gtg gaa ggg gag aac cac acc tac tgc atc         6576
Thr His Glu Ala Glu Ile Val Glu Gly Glu Asn His Thr Tyr Cys Ile
            2180                2185                2190 cgc ttt gtt ccc gct gag atg ggc aca cac aca gtc agc gtg aag tac         6624
Arg Phe Val Pro Ala Glu Met Gly Thr His Thr Val Ser Val Lys Tyr
    2195                2200                2205 aag ggc cag cac gtg cct ggg agc ccc ttc cag ttc acc gtg ggg ccc         6672
Lys Gly Gln His Val Pro Gly Ser Pro Phe Gln Phe Thr Val Gly Pro
 2210                2215                2220 cta ggg gaa ggg gga gcc cac aag gtc cga gct ggg ggc cct ggc ctg         6720
Leu Gly Glu Gly Gly Ala His Lys Val Arg Ala Gly Gly Pro Gly Leu
2225                2230                2235                2240 gag aga gct gaa gct gga gtg cca gcc gaa ttc agt atc tgg acc cgg         6768
Glu Arg Ala Glu Ala Gly Val Pro Ala Glu Phe Ser Ile Trp Thr Arg
                2245                2250                2255 gaa gct ggt gct gga ggc ctg gcc att gct gtc gag ggc ccc agc aag         6816
Glu Ala Gly Ala Gly Gly Leu Ala Ile Ala Val Glu Gly Pro Ser Lys
            2260                2265                2270 gct gag atc tct ttt gag gac cgc aag gac ggc tcc tgt ggt gtg gct         6864
Ala Glu Ile Ser Phe Glu Asp Arg Lys Asp Gly Ser Cys Gly Val Ala
    2275                2280                2285 tat gtg gtc cag gag cca ggt gac tac gaa gtc tca gtc aag ttc aac         6912
Tyr Val Val Gln Glu Pro Gly Asp Tyr Glu Val Ser Val Lys Phe Asn
 2290                2295                2300 gag gaa cac att ccc gac agc ccc ttc gtg gtg cct gtg gct tct ccg         6960
Glu Glu His Ile Pro Asp Ser Pro Phe Val Val Pro Val Ala Ser Pro
2305                2310                2315                2320 tct ggc gac gcc cgc cgc ctc act gtt tct agc ctt cag gag tca ggg         7008
Ser Gly Asp Ala Arg Arg Leu Thr Val Ser Ser Leu Gln Glu Ser Gly
                2325                2330                2335
```

```
cta aag gtc aac cag cca gcc tct ttt gca gtc agc ctg aac ggg gcc    7056
Leu Lys Val Asn Gln Pro Ala Ser Phe Ala Val Ser Leu Asn Gly Ala
        2340                2345                2350 aag ggg gcg atc gat gcc aag gtg cac agc ccc tca gga gcc ctg gag    7104
Lys Gly Ala Ile Asp Ala Lys Val His Ser Pro Ser Gly Ala Leu Glu
2355                2360                2365 gag tgc tat gtc aca gaa att gac caa gat aag tat gct gtg cgc ttc    7152
Glu Cys Tyr Val Thr Glu Ile Asp Gln Asp Lys Tyr Ala Val Arg Phe
    2370                2375                2380 atc cct cgg gag aat ggc gtt tac ctg att gac gtc aag ttc aac ggc    7200
Ile Pro Arg Glu Asn Gly Val Tyr Leu Ile Asp Val Lys Phe Asn Gly
2385                2390                2395                2400 acc cac atc cct gga agc ccc ttc aag atc cga gtt ggg gag cct ggg    7248
Thr His Ile Pro Gly Ser Pro Phe Lys Ile Arg Val Gly Glu Pro Gly
            2405                2410                2415 cat gga ggg gac cca ggc ttg gtg tct gct tac gga gca ggt ctg gaa    7296
His Gly Gly Asp Pro Gly Leu Val Ser Ala Tyr Gly Ala Gly Leu Glu
        2420                2425                2430 ggc ggt gtc aca ggg aac cca gct gag ttc gtc gtg aac acg agc aat    7344
Gly Gly Val Thr Gly Asn Pro Ala Glu Phe Val Val Asn Thr Ser Asn
    2435                2440                2445 gcg gga gct ggt gcc ctg tcg gtg acc att gac ggc ccc tcc aag gtg    7392
Ala Gly Ala Gly Ala Leu Ser Val Thr Ile Asp Gly Pro Ser Lys Val
2450                2455                2460 aag atg gat tgc cag gag tgc cct gag ggc tac cgc gtc acc tat acc    7440
Lys Met Asp Cys Gln Glu Cys Pro Glu Gly Tyr Arg Val Thr Tyr Thr
2465                2470                2475                2480 ccc atg gca cct ggc agc tac ctc atc tcc atc aag tac ggc ggc ccc    7488
Pro Met Ala Pro Gly Ser Tyr Leu Ile Ser Ile Lys Tyr Gly Gly Pro
            2485                2490                2495 tac cac att ggg ggc agc ccc ttc aag gcc aaa gtc aca ggc ccc cgt    7536
Tyr His Ile Gly Gly Ser Pro Phe Lys Ala Lys Val Thr Gly Pro Arg
        2500                2505                2510 ctc gtc agc aac cac agc ctc cac gag aca tca tca gtg ttt gta gac    7584
Leu Val Ser Asn His Ser Leu His Glu Thr Ser Ser Val Phe Val Asp
    2515                2520                2525 tct ctg acc aag gcc acc tgt gcc ccc cag cat ggg gcc ccg ggt cct    7632
Ser Leu Thr Lys Ala Thr Cys Ala Pro Gln His Gly Ala Pro Gly Pro
2530                2535                2540 ggg cct gct gac gcc agc aag gtg gtg gcc aag ggc ctg ggg ctg agc    7680
Gly Pro Ala Asp Ala Ser Lys Val Val Ala Lys Gly Leu Gly Leu Ser
2545                2550                2555                2560 aag gcc tac gta ggc cag aag agc agc ttc aca gta gac tgc agc aaa    7728
Lys Ala Tyr Val Gly Gln Lys Ser Ser Phe Thr Val Asp Cys Ser Lys
            2565                2570                2575 gca ggc aac aac atg ctg ctg gtg ggg gtt cat ggc cca agg acc ccc    7776
Ala Gly Asn Asn Met Leu Leu Val Gly Val His Gly Pro Arg Thr Pro
        2580                2585                2590 tgc gag gag atc ctg gtg aag cac gtg ggc agc cgg ctc tac agc gtg    7824
Cys Glu Glu Ile Leu Val Lys His Val Gly Ser Arg Leu Tyr Ser Val
    2595                2600                2605 tcc tac ctg ctc aag gac aag ggg gag tac aca ctg gtg gtc aaa tgg    7872
Ser Tyr Leu Leu Lys Asp Lys Gly Glu Tyr Thr Leu Val Val Lys Trp
2610                2615                2620 ggg gac gag cac atc cca ggc agc ccc tac cgc gtt gtg gtg ccc tga    7920
Gly Asp Glu His Ile Pro Gly Ser Pro Tyr Arg Val Val Val Pro
2625                2630                2635

<210> SEQ ID NO 12
<211> LENGTH: 2639
```

```
<212> TYPE: PRT
<213> ORGANISM: Homo sapiens
<220> FEATURE:
<223> OTHER INFORMATION: Human filamin A isoform 1

<400> SEQUENCE: 12
```

| | | | | | | | | | | | | | | |
|---|---|---|---|---|---|---|---|---|---|---|---|---|---|---|
| Met | Ser | Ser | Ser | His | Ser | Arg | Ala | Gly | Gln | Ser | Ala | Ala | Gly | Ala | Ala |
| 1 | | | | 5 | | | | | 10 | | | | | 15 | |
| Pro | Gly | Gly | Gly | Val | Asp | Thr | Arg | Asp | Ala | Glu | Met | Pro | Ala | Thr | Glu |
| | | | 20 | | | | | 25 | | | | | 30 | | |
| Lys | Asp | Leu | Ala | Glu | Asp | Ala | Pro | Trp | Lys | Lys | Ile | Gln | Gln | Asn | Thr |
| | | | 35 | | | | | 40 | | | | | 45 | | |
| Phe | Thr | Arg | Trp | Cys | Asn | Glu | His | Leu | Lys | Cys | Val | Ser | Lys | Arg | Ile |
| | 50 | | | | | 55 | | | | | 60 | | | | |
| Ala | Asn | Leu | Gln | Thr | Asp | Leu | Ser | Asp | Gly | Leu | Arg | Leu | Ile | Ala | Leu |
| 65 | | | | | 70 | | | | | 75 | | | | | 80 |
| Leu | Glu | Val | Leu | Ser | Gln | Lys | Lys | Met | His | Arg | Lys | His | Asn | Gln | Arg |
| | | | | 85 | | | | | 90 | | | | | 95 | |
| Pro | Thr | Phe | Arg | Gln | Met | Gln | Leu | Glu | Asn | Val | Ser | Val | Ala | Leu | Glu |
| | | | 100 | | | | | 105 | | | | | 110 | | |
| Phe | Leu | Asp | Arg | Glu | Ser | Ile | Lys | Leu | Val | Ser | Ile | Asp | Ser | Lys | Ala |
| | | | 115 | | | | | 120 | | | | | 125 | | |
| Ile | Val | Asp | Gly | Asn | Leu | Lys | Leu | Ile | Leu | Gly | Leu | Ile | Trp | Thr | Leu |
| | 130 | | | | | 135 | | | | | 140 | | | | |
| Ile | Leu | His | Tyr | Ser | Ile | Ser | Met | Pro | Met | Trp | Asp | Glu | Glu | Glu | Asp |
| 145 | | | | | 150 | | | | | 155 | | | | | 160 |
| Glu | Glu | Ala | Lys | Lys | Gln | Thr | Pro | Lys | Gln | Arg | Leu | Leu | Gly | Trp | Ile |
| | | | | 165 | | | | | 170 | | | | | 175 | |
| Gln | Asn | Lys | Leu | Pro | Gln | Leu | Pro | Ile | Thr | Asn | Phe | Ser | Arg | Asp | Trp |
| | | | 180 | | | | | 185 | | | | | 190 | | |
| Gln | Ser | Gly | Arg | Ala | Leu | Gly | Ala | Leu | Val | Asp | Ser | Cys | Ala | Pro | Gly |
| | | | 195 | | | | | 200 | | | | | 205 | | |
| Leu | Cys | Pro | Asp | Trp | Asp | Ser | Trp | Asp | Ala | Ser | Lys | Pro | Val | Thr | Asn |
| | 210 | | | | | 215 | | | | | 220 | | | | |
| Ala | Arg | Glu | Ala | Met | Gln | Gln | Ala | Asp | Asp | Trp | Leu | Gly | Ile | Pro | Gln |
| 225 | | | | | 230 | | | | | 235 | | | | | 240 |
| Val | Ile | Thr | Pro | Glu | Glu | Ile | Val | Asp | Pro | Asn | Val | Asp | Glu | His | Ser |
| | | | | 245 | | | | | 250 | | | | | 255 | |
| Val | Met | Thr | Tyr | Leu | Ser | Gln | Phe | Pro | Lys | Ala | Lys | Leu | Lys | Pro | Gly |
| | | | 260 | | | | | 265 | | | | | 270 | | |
| Ala | Pro | Leu | Arg | Pro | Lys | Leu | Asn | Pro | Lys | Lys | Ala | Arg | Ala | Tyr | Gly |
| | | | 275 | | | | | 280 | | | | | 285 | | |
| Pro | Gly | Ile | Glu | Pro | Thr | Gly | Asn | Met | Val | Lys | Lys | Arg | Ala | Glu | Phe |
| | 290 | | | | | 295 | | | | | 300 | | | | |
| Thr | Val | Glu | Thr | Arg | Ser | Ala | Gly | Gln | Gly | Glu | Val | Leu | Val | Tyr | Val |
| 305 | | | | | 310 | | | | | 315 | | | | | 320 |
| Glu | Asp | Pro | Ala | Gly | His | Gln | Glu | Glu | Ala | Lys | Val | Thr | Ala | Asn | Asn |
| | | | | 325 | | | | | 330 | | | | | 335 | |
| Asp | Lys | Asn | Arg | Thr | Phe | Ser | Val | Trp | Tyr | Val | Pro | Glu | Val | Thr | Gly |
| | | | 340 | | | | | 345 | | | | | 350 | | |
| Thr | His | Lys | Val | Thr | Val | Leu | Phe | Ala | Gly | Gln | His | Ile | Ala | Lys | Ser |
| | | | 355 | | | | | 360 | | | | | 365 | | |
| Pro | Phe | Glu | Val | Tyr | Val | Asp | Lys | Ser | Gln | Gly | Asp | Ala | Ser | Lys | Val |
| | 370 | | | | | 375 | | | | | 380 | | | | |

```
Thr Ala Gln Gly Pro Gly Leu Glu Pro Ser Gly Asn Ile Ala Asn Lys
385                 390                 395                 400

Thr Thr Tyr Phe Glu Ile Phe Thr Ala Gly Ala Gly Thr Gly Glu Val
            405                 410                 415

Glu Val Val Ile Gln Asp Pro Met Gly Gln Lys Gly Thr Val Glu Pro
                420                 425                 430

Gln Leu Glu Ala Arg Gly Asp Ser Thr Tyr Arg Cys Ser Tyr Gln Pro
        435                 440                 445

Thr Met Glu Gly Val His Thr Val His Val Thr Phe Ala Gly Val Pro
    450                 455                 460

Ile Pro Arg Ser Pro Tyr Thr Val Thr Val Gly Gln Ala Cys Asn Pro
465                 470                 475                 480

Ser Ala Cys Arg Ala Val Gly Arg Gly Leu Gln Pro Lys Gly Val Arg
            485                 490                 495

Val Lys Glu Thr Ala Asp Phe Lys Val Tyr Thr Lys Gly Ala Gly Ser
                500                 505                 510

Gly Glu Leu Lys Val Thr Val Lys Gly Pro Lys Gly Glu Glu Arg Val
        515                 520                 525

Lys Gln Lys Asp Leu Gly Asp Gly Val Tyr Gly Phe Glu Tyr Tyr Pro
530                 535                 540

Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
            565                 570                 575

Gln Lys Val Arg Ala Trp Gly Pro Gly Leu Glu Gly Gly Val Val Gly
                580                 585                 590

Lys Ser Ala Asp Phe Val Val Glu Ala Ile Gly Asp Asp Val Gly Thr
        595                 600                 605

Leu Gly Phe Ser Val Glu Gly Pro Ser Gln Ala Lys Ile Glu Cys Asp
610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
            645                 650                 655

Ser Pro Phe Met Ala Asp Ile Arg Asp Ala Pro Gln Asp Phe His Pro
                660                 665                 670

Asp Arg Val Lys Ala Arg Gly Pro Gly Leu Glu Lys Thr Gly Val Ala
        675                 680                 685

Val Asn Lys Pro Ala Glu Phe Thr Val Asp Ala Lys His Gly Gly Lys
690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
            725                 730                 735

Pro Arg Lys Pro Val Lys His Thr Ala Met Val Ser Trp Gly Gly Val
                740                 745                 750

Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
```

```
                805                 810                 815
Pro Ala Glu Ala Asp Ile Asp Phe Asp Ile Arg Asn Asp Asn Asp
                820                 825                 830

Thr Phe Thr Val Lys Tyr Thr Pro Arg Gly Ala Gly Ser Tyr Thr Ile
                835                 840                 845

Met Val Leu Phe Ala Asp Gln Ala Thr Pro Thr Ser Pro Ile Arg Val
        850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
                900                 905                 910

Gly Leu Thr Lys Gly Asp Ala Val Arg Asp Val Asp Ile Ile Asp His
                915                 920                 925

His Asp Asn Thr Tyr Thr Val Lys Tyr Thr Pro Val Gln Gln Gly Pro
        930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
                980                 985                 990

Val Lys Ser Lys Gly Ala Gly Gly Gln Gly Lys Val Ala Ser Lys Ile
                995                1000                1005

Val Gly Pro Ser Gly Ala Ala Val Pro Cys Lys Val Glu Pro Gly Leu
        1010                1015                1020

Gly Ala Asp Asn Ser Val Val Arg Phe Leu Pro Arg Glu Glu Gly Pro
1025                1030                1035                1040

Tyr Glu Val Glu Val Thr Tyr Asp Gly Val Pro Val Pro Gly Ser Pro
                1045                1050                1055

Phe Pro Leu Glu Ala Val Ala Pro Thr Lys Pro Ser Lys Val Lys Ala
                1060                1065                1070

Phe Gly Pro Gly Leu Gln Gly Gly Ser Ala Gly Ser Pro Ala Arg Phe
                1075                1080                1085

Thr Ile Asp Thr Lys Gly Ala Gly Thr Gly Gly Leu Gly Leu Thr Val
        1090                1095                1100

Glu Gly Pro Cys Glu Ala Gln Leu Glu Cys Leu Asp Asn Gly Asp Gly
1105                1110                1115                1120

Thr Cys Ser Val Ser Tyr Val Pro Thr Glu Pro Gly Asp Tyr Asn Ile
                1125                1130                1135

Asn Ile Leu Phe Ala Asp Thr His Ile Pro Gly Ser Pro Phe Lys Ala
                1140                1145                1150

His Val Val Pro Cys Phe Asp Ala Ser Lys Val Lys Cys Ser Gly Pro
                1155                1160                1165

Gly Leu Glu Arg Ala Thr Ala Gly Glu Val Gly Gln Phe Gln Val Asp
        1170                1175                1180

Cys Ser Ser Ala Gly Ser Ala Glu Leu Thr Ile Glu Ile Cys Ser Glu
1185                1190                1195                1200

Ala Gly Leu Pro Ala Glu Val Tyr Ile Gln Asp His Gly Asp Gly Thr
                1205                1210                1215

His Thr Ile Thr Tyr Ile Pro Leu Cys Pro Gly Ala Tyr Thr Val Thr
        1220                1225                1230
```

-continued

```
Ile Lys Tyr Gly Gly Gln Pro Val Pro Asn Phe Pro Ser Lys Leu Gln
        1235                1240                1245
Val Glu Pro Ala Val Asp Thr Ser Gly Val Gln Cys Tyr Gly Pro Gly
    1250                1255                1260
Ile Glu Gly Gln Gly Val Phe Arg Glu Ala Thr Thr Glu Phe Ser Val
1265                1270                1275                1280
Asp Ala Arg Ala Leu Thr Gln Thr Gly Gly Pro His Val Lys Ala Arg
                1285                1290                1295
Val Ala Asn Pro Ser Gly Asn Leu Thr Glu Thr Tyr Val Gln Asp Arg
            1300                1305                1310
Gly Asp Gly Met Tyr Lys Val Glu Tyr Thr Pro Tyr Glu Glu Gly Leu
        1315                1320                1325
His Ser Val Asp Val Thr Tyr Asp Gly Ser Pro Val Pro Ser Ser Pro
    1330                1335                1340
Phe Gln Val Pro Val Thr Glu Gly Cys Asp Pro Ser Arg Val Arg Val
1345                1350                1355                1360
His Gly Pro Gly Ile Gln Ser Gly Thr Thr Asn Lys Pro Asn Lys Phe
                1365                1370                1375
Thr Val Glu Thr Arg Gly Ala Gly Thr Gly Gly Leu Gly Leu Ala Val
            1380                1385                1390
Glu Gly Pro Ser Glu Ala Lys Met Ser Cys Met Asp Asn Lys Asp Gly
        1395                1400                1405
Ser Cys Ser Val Glu Tyr Ile Pro Tyr Glu Ala Gly Thr Tyr Ser Leu
    1410                1415                1420
Asn Val Thr Tyr Gly Gly His Gln Val Pro Gly Ser Pro Phe Lys Val
1425                1430                1435                1440
Pro Val His Asp Val Thr Asp Ala Ser Lys Val Lys Cys Ser Gly Pro
                1445                1450                1455
Gly Leu Ser Pro Gly Met Val Arg Ala Asn Leu Pro Gln Ser Phe Gln
            1460                1465                1470
Val Asp Thr Ser Lys Ala Gly Val Ala Pro Leu Gln Val Lys Val Gln
        1475                1480                1485
Gly Pro Lys Gly Leu Val Glu Pro Val Asp Val Val Asp Asn Ala Asp
    1490                1495                1500
Gly Thr Gln Thr Val Asn Tyr Val Pro Ser Arg Glu Gly Pro Tyr Ser
1505                1510                1515                1520
Ile Ser Val Leu Tyr Gly Asp Glu Glu Val Pro Arg Ser Pro Phe Lys
                1525                1530                1535
Val Lys Val Leu Pro Thr His Asp Ala Ser Lys Val Lys Ala Ser Gly
            1540                1545                1550
Pro Gly Leu Asn Thr Thr Gly Val Pro Ala Ser Leu Pro Val Glu Phe
        1555                1560                1565
Thr Ile Asp Ala Lys Asp Ala Gly Glu Gly Leu Leu Ala Val Gln Ile
    1570                1575                1580
Thr Asp Pro Glu Gly Lys Pro Lys Lys Thr His Ile Gln Asp Asn His
1585                1590                1595                1600
Asp Gly Thr Tyr Thr Val Ala Tyr Val Pro Asp Val Thr Gly Arg Tyr
                1605                1610                1615
Thr Ile Leu Ile Lys Tyr Gly Gly Asp Glu Ile Pro Phe Ser Pro Tyr
            1620                1625                1630
Arg Val Arg Ala Val Pro Thr Gly Asp Ala Ser Lys Cys Thr Val Thr
        1635                1640                1645
```

-continued

Gly Ala Gly Ile Gly Pro Thr Ile Gln Ile Gly Glu Glu Thr Val Ile
1650                1655                1660

Thr Val Asp Thr Lys Ala Ala Gly Lys Gly Lys Val Thr Cys Thr Val
1665                1670                1675                1680

Cys Thr Pro Asp Gly Ser Glu Val Asp Val Asp Val Val Glu Asn Glu
            1685                1690                1695

Asp Gly Thr Phe Asp Ile Phe Tyr Thr Ala Pro Gln Pro Gly Lys Tyr
        1700                1705                1710

Val Ile Cys Val Arg Phe Gly Glu His Val Pro Asn Ser Pro Phe
    1715                1720                1725

Gln Val Thr Ala Leu Ala Gly Asp Gln Pro Ser Val Gln Pro Pro Leu
1730                1735                1740

Arg Ser Gln Gln Leu Ala Pro Gln Tyr Thr Tyr Ala Gln Gly Gly Gln
1745                1750                1755                1760

Gln Thr Trp Ala Pro Glu Arg Pro Leu Val Gly Val Asn Gly Leu Asp
        1765                1770                1775

Val Thr Ser Leu Arg Pro Phe Asp Leu Val Ile Pro Phe Thr Ile Lys
            1780                1785                1790

Lys Gly Glu Ile Thr Gly Glu Val Arg Met Pro Ser Gly Lys Val Ala
    1795                1800                1805

Gln Pro Thr Ile Thr Asp Asn Lys Asp Gly Thr Val Thr Val Arg Tyr
1810                1815                1820

Ala Pro Ser Glu Ala Gly Leu His Glu Met Asp Ile Arg Tyr Asp Asn
1825                1830                1835                1840

Met His Ile Pro Gly Ser Pro Leu Gln Phe Tyr Val Asp Tyr Val Asn
            1845                1850                1855

Cys Gly His Val Thr Ala Tyr Gly Pro Gly Leu Thr His Gly Val Val
            1860                1865                1870

Asn Lys Pro Ala Thr Phe Thr Val Asn Thr Lys Asp Ala Gly Glu Gly
        1875                1880                1885

Gly Leu Ser Leu Ala Ile Glu Gly Pro Ser Lys Ala Glu Ile Ser Cys
    1890                1895                1900

Thr Asp Asn Gln Asp Gly Thr Cys Ser Val Ser Tyr Leu Pro Val Leu
1905                1910                1915                1920

Pro Gly Asp Tyr Ser Ile Leu Val Lys Tyr Asn Glu Gln His Val Pro
            1925                1930                1935

Gly Ser Pro Phe Thr Ala Arg Val Thr Gly Asp Asp Ser Met Arg Met
        1940                1945                1950

Ser His Leu Lys Val Gly Ser Ala Ala Asp Ile Pro Ile Asn Ile Ser
        1955                1960                1965

Glu Thr Asp Leu Ser Leu Leu Thr Ala Thr Val Val Pro Pro Ser Gly
    1970                1975                1980

Arg Glu Glu Pro Cys Leu Leu Lys Arg Leu Arg Asn Gly His Val Gly
1985                1990                1995                2000

Ile Ser Phe Val Pro Lys Glu Thr Gly Glu His Leu Val His Val Lys
            2005                2010                2015

Lys Asn Gly Gln His Val Ala Ser Ser Pro Ile Pro Val Val Ile Ser
            2020                2025                2030

Gln Ser Glu Ile Gly Asp Ala Ser Arg Val Arg Val Ser Gly Gln Gly
        2035                2040                2045

Leu His Glu Gly His Thr Phe Glu Pro Ala Glu Phe Ile Ile Asp Thr
    2050                2055                2060

Arg Asp Ala Gly Tyr Gly Gly Leu Ser Leu Ser Ile Glu Gly Pro Ser

```
                2065                2070                2075                2080
Lys Val Asp Ile Asn Thr Glu Asp Leu Glu Asp Gly Thr Cys Arg Val
                2085                2090                2095

Thr Tyr Cys Pro Thr Glu Pro Gly Asn Tyr Ile Ile Asn Ile Lys Phe
                2100                2105                2110

Ala Asp Gln His Val Pro Gly Ser Pro Phe Ser Val Lys Val Thr Gly
                2115                2120                2125

Glu Gly Arg Val Lys Glu Ser Ile Thr Arg Arg Arg Ala Pro Ser
                2130                2135                2140

Val Ala Asn Val Gly Ser His Cys Asp Leu Ser Leu Lys Ile Pro Glu
2145                2150                2155                2160

Ile Ser Ile Gln Asp Met Thr Ala Gln Val Thr Ser Pro Ser Gly Lys
                2165                2170                2175

Thr His Glu Ala Glu Ile Val Glu Gly Glu Asn His Thr Tyr Cys Ile
                2180                2185                2190

Arg Phe Val Pro Ala Glu Met Gly Thr His Thr Val Ser Val Lys Tyr
                2195                2200                2205

Lys Gly Gln His Val Pro Gly Ser Pro Phe Gln Phe Thr Val Gly Pro
                2210                2215                2220

Leu Gly Glu Gly Gly Ala His Lys Val Arg Ala Gly Gly Pro Gly Leu
2225                2230                2235                2240

Glu Arg Ala Glu Ala Gly Val Pro Ala Glu Phe Ser Ile Trp Thr Arg
                2245                2250                2255

Glu Ala Gly Ala Gly Gly Leu Ala Ile Ala Val Glu Gly Pro Ser Lys
                2260                2265                2270

Ala Glu Ile Ser Phe Glu Asp Arg Lys Asp Gly Ser Cys Gly Val Ala
                2275                2280                2285

Tyr Val Val Gln Glu Pro Gly Asp Tyr Glu Val Ser Val Lys Phe Asn
                2290                2295                2300

Glu Glu His Ile Pro Asp Ser Pro Phe Val Pro Val Ala Ser Pro
2305                2310                2315                2320

Ser Gly Asp Ala Arg Arg Leu Thr Val Ser Ser Leu Gln Glu Ser Gly
                2325                2330                2335

Leu Lys Val Asn Gln Pro Ala Ser Phe Ala Val Ser Leu Asn Gly Ala
                2340                2345                2350

Lys Gly Ala Ile Asp Ala Lys Val His Ser Pro Ser Gly Ala Leu Glu
                2355                2360                2365

Glu Cys Tyr Val Thr Glu Ile Asp Gln Asp Lys Tyr Ala Val Arg Phe
                2370                2375                2380

Ile Pro Arg Glu Asn Gly Val Tyr Leu Ile Asp Val Lys Phe Asn Gly
2385                2390                2395                2400

Thr His Ile Pro Gly Ser Pro Phe Lys Ile Arg Val Gly Glu Pro Gly
                2405                2410                2415

His Gly Gly Asp Pro Gly Leu Val Ser Ala Tyr Gly Ala Gly Leu Glu
                2420                2425                2430

Gly Gly Val Thr Gly Asn Pro Ala Glu Phe Val Val Asn Thr Ser Asn
                2435                2440                2445

Ala Gly Ala Gly Ala Leu Ser Val Thr Ile Asp Gly Pro Ser Lys Val
                2450                2455                2460

Lys Met Asp Cys Gln Glu Cys Pro Glu Gly Tyr Arg Val Thr Tyr Thr
2465                2470                2475                2480

Pro Met Ala Pro Gly Ser Tyr Leu Ile Ser Ile Lys Tyr Gly Gly Pro
                2485                2490                2495
```

```
Tyr His Ile Gly Gly Ser Pro Phe Lys Ala Lys Val Thr Gly Pro Arg
        2500                2505                2510

Leu Val Ser Asn His Ser Leu His Glu Thr Ser Ser Val Phe Val Asp
        2515                2520                2525

Ser Leu Thr Lys Ala Thr Cys Ala Pro Gln His Gly Ala Pro Gly Pro
        2530                2535                2540

Gly Pro Ala Asp Ala Ser Lys Val Val Ala Lys Gly Leu Gly Leu Ser
2545                2550                2555                2560

Lys Ala Tyr Val Gly Gln Lys Ser Ser Phe Thr Val Asp Cys Ser Lys
                2565                2570                2575

Ala Gly Asn Asn Met Leu Leu Val Gly Val His Gly Pro Arg Thr Pro
        2580                2585                2590

Cys Glu Glu Ile Leu Val Lys His Val Gly Ser Arg Leu Tyr Ser Val
        2595                2600                2605

Ser Tyr Leu Leu Lys Asp Lys Gly Glu Tyr Thr Leu Val Val Lys Trp
        2610                2615                2620

Gly Asp Glu His Ile Pro Gly Ser Pro Tyr Arg Val Val Val Pro
2625                2630                2635

<210> SEQ ID NO 13
<211> LENGTH: 7944
<212> TYPE: DNA
<213> ORGANISM: Homo sapiens
<220> FEATURE:
<221> NAME/KEY: CDS
<222> LOCATION: (1)...(7944)
<223> OTHER INFORMATION: Coding sequence for human filamin A isoform 2

<400> SEQUENCE: 13 atg agt agc tcc cac tct cgg gcg ggc cag agc gca gca ggc gcg gct     48
Met Ser Ser Ser His Ser Arg Ala Gly Gln Ser Ala Ala Gly Ala Ala
 1               5                  10                  15 ccg ggc ggc ggc gtc gac acg cgg gac gcc gag atg ccg gcc acc gag     96
Pro Gly Gly Gly Val Asp Thr Arg Asp Ala Glu Met Pro Ala Thr Glu
                20                  25                  30 aag gac ctg gcg gag gac gcg ccg tgg aag aag atc cag cag aac act    144
Lys Asp Leu Ala Glu Asp Ala Pro Trp Lys Lys Ile Gln Gln Asn Thr
            35                  40                  45 ttc acg cgc tgg tgc aac gag cac ctg aag tgc gtg agc aag cgc atc    192
Phe Thr Arg Trp Cys Asn Glu His Leu Lys Cys Val Ser Lys Arg Ile
        50                  55                  60 gcc aac ctg cag acg gac ctg agc gac ggg ctg cgg ctt atc gcg ctg    240
Ala Asn Leu Gln Thr Asp Leu Ser Asp Gly Leu Arg Leu Ile Ala Leu
 65                  70                  75                  80 ttg gag gtg ctc agc cag aag aag atg cac cgc aag cac aac cag cgg    288
Leu Glu Val Leu Ser Gln Lys Lys Met His Arg Lys His Asn Gln Arg
                85                  90                  95 ccc act ttc cgc caa atg cag ctt gag aac gtg tcg gtg gcg ctc gag    336
Pro Thr Phe Arg Gln Met Gln Leu Glu Asn Val Ser Val Ala Leu Glu
               100                 105                 110 ttc ctg gac cgc gag agc atc aaa ctg gtg tcc atc gac agc aag gcc    384
Phe Leu Asp Arg Glu Ser Ile Lys Leu Val Ser Ile Asp Ser Lys Ala
            115                 120                 125 atc gtg gac ggg aac ctg aag ctg atc ctg ggc ctc atc tgg acc ctg    432
Ile Val Asp Gly Asn Leu Lys Leu Ile Leu Gly Leu Ile Trp Thr Leu
        130                 135                 140 atc ctg cac tac tcc atc tcc atg ccc atg tgg gac gag gag gag gat    480
Ile Leu His Tyr Ser Ile Ser Met Pro Met Trp Asp Glu Glu Glu Asp
145                 150                 155                 160
```

```
gag gag gcc aag aag cag acc ccc aag cag agg ctc ctg ggc tgg atc      528
Glu Glu Ala Lys Lys Gln Thr Pro Lys Gln Arg Leu Leu Gly Trp Ile
            165                 170                 175 cag aac aag ctg ccg cag ctg ccc atc acc aac ttc agc cgg gac tgg      576
Gln Asn Lys Leu Pro Gln Leu Pro Ile Thr Asn Phe Ser Arg Asp Trp
        180                 185                 190 cag agc ggc cgg gcc ctg ggc gcc ctg gtg gac agc tgt gcc ccg ggc      624
Gln Ser Gly Arg Ala Leu Gly Ala Leu Val Asp Ser Cys Ala Pro Gly
    195                 200                 205 ctg tgt cct gac tgg gac tct tgg gac gcc agc aag ccc gtt acc aat      672
Leu Cys Pro Asp Trp Asp Ser Trp Asp Ala Ser Lys Pro Val Thr Asn
210                 215                 220 gcg cga gag gcc atg cag cag gcg gat gac tgg ctg ggc atc ccc cag      720
Ala Arg Glu Ala Met Gln Gln Ala Asp Asp Trp Leu Gly Ile Pro Gln
225                 230                 235                 240 gtg atc acc ccc gag gag att gtg gac ccc aac gtg gac gag cac tct      768
Val Ile Thr Pro Glu Glu Ile Val Asp Pro Asn Val Asp Glu His Ser
            245                 250                 255 gtc atg acc tac ctg tcc cag ttc ccc aag gcc aag ctg aag cca ggg      816
Val Met Thr Tyr Leu Ser Gln Phe Pro Lys Ala Lys Leu Lys Pro Gly
        260                 265                 270 gct ccc ttg cgg ccc aaa ctg aac ccg aag aaa gcc cgt gcc tac ggg      864
Ala Pro Leu Arg Pro Lys Leu Asn Pro Lys Lys Ala Arg Ala Tyr Gly
    275                 280                 285 cca ggc atc gag ccc aca ggc aac atg gtg aag aag cgg gca gag ttc      912
Pro Gly Ile Glu Pro Thr Gly Asn Met Val Lys Lys Arg Ala Glu Phe
290                 295                 300 act gtg gag acc aga agt gct ggc cag gga gag gtg ctg gtg tac gtg      960
Thr Val Glu Thr Arg Ser Ala Gly Gln Gly Glu Val Leu Val Tyr Val
305                 310                 315                 320 gag gac ccg gcc gga cac cag gag gag gca aaa gtg acc gcc aat aac     1008
Glu Asp Pro Ala Gly His Gln Glu Glu Ala Lys Val Thr Ala Asn Asn
            325                 330                 335 gac aag aac cgc acc ttc tcc gtc tgg tac gtc ccc gag gtg acg ggg     1056
Asp Lys Asn Arg Thr Phe Ser Val Trp Tyr Val Pro Glu Val Thr Gly
        340                 345                 350 act cat aag gtt act gtg ctc ttt gct ggc cag cac atc gcc aag agc     1104
Thr His Lys Val Thr Val Leu Phe Ala Gly Gln His Ile Ala Lys Ser
    355                 360                 365 ccc ttc gag gtg tac gtg gat aag tca cag ggt gac gcc agc aaa gtg     1152
Pro Phe Glu Val Tyr Val Asp Lys Ser Gln Gly Asp Ala Ser Lys Val
370                 375                 380 aca gcc caa ggt ccc ggc ctg gag ccc agt ggc aac atc gcc aac aag     1200
Thr Ala Gln Gly Pro Gly Leu Glu Pro Ser Gly Asn Ile Ala Asn Lys
385                 390                 395                 400 acc acc tac ttt gag atc ttt acg gca gga gct ggc acg ggc gag gtc     1248
Thr Thr Tyr Phe Glu Ile Phe Thr Ala Gly Ala Gly Thr Gly Glu Val
            405                 410                 415 gag gtt gtg atc cag gac ccc atg gga cag aag ggc acg gta gag cct     1296
Glu Val Val Ile Gln Asp Pro Met Gly Gln Lys Gly Thr Val Glu Pro
        420                 425                 430 cag ctg gag gcc cgg ggc gac agc aca tac cgc tgc agc tac cag ccc     1344
Gln Leu Glu Ala Arg Gly Asp Ser Thr Tyr Arg Cys Ser Tyr Gln Pro
    435                 440                 445 acc atg gag ggc gtc cac acc gtg cac gtc acg ttt gcc ggc gtg ccc     1392
Thr Met Glu Gly Val His Thr Val His Val Thr Phe Ala Gly Val Pro
450                 455                 460 atc cct cgc agc ccc tac act gtc act gtt ggc caa gcc tgt aac ccg     1440
Ile Pro Arg Ser Pro Tyr Thr Val Thr Val Gly Gln Ala Cys Asn Pro
```

-continued

```
              465                 470                 475                 480
         agt gcc tgc cgg gcg gtt ggc cgg ggc ctc cag ccc aag ggt gtg cgg      1488
         Ser Ala Cys Arg Ala Val Gly Arg Gly Leu Gln Pro Lys Gly Val Arg
                         485                 490                 495 gtg aag gag aca gct gac ttc aag gtg tac aca aag ggc gct ggc agt      1536
         Val Lys Glu Thr Ala Asp Phe Lys Val Tyr Thr Lys Gly Ala Gly Ser
                     500                 505                 510 ggg gag ctg aag gtc acc gtg aag ggc ccc aag gga gag gag cgc gtg      1584
         Gly Glu Leu Lys Val Thr Val Lys Gly Pro Lys Gly Glu Glu Arg Val
                 515                 520                 525 aag cag aag gac ctg ggg gat ggc gtg tat ggc ttc gag tat tac ccc      1632
         Lys Gln Lys Asp Leu Gly Asp Gly Val Tyr Gly Phe Glu Tyr Tyr Pro
             530                 535                 540 atg gtc cct gga acc tat atc gtc acc atc acg tgg ggt ggt cag aac      1680
         Met Val Pro Gly Thr Tyr Ile Val Thr Ile Thr Trp Gly Gly Gln Asn
         545                 550                 555                 560 atc ggg cgc agt ccc ttc gaa gtg aag gtg ggc acc gag tgt ggc aat      1728
         Ile Gly Arg Ser Pro Phe Glu Val Lys Val Gly Thr Glu Cys Gly Asn
                         565                 570                 575 cag aag gta cgg gcc tgg ggc cct ggg ctg gag ggc ggc gtc gtt ggc      1776
         Gln Lys Val Arg Ala Trp Gly Pro Gly Leu Glu Gly Gly Val Val Gly
                     580                 585                 590 aag tca gca gac ttt gtg gtg gag gct atc ggg gac gac gtg ggc acg      1824
         Lys Ser Ala Asp Phe Val Val Glu Ala Ile Gly Asp Asp Val Gly Thr
                 595                 600                 605 ctg ggc ttc tcg gtg gaa ggg cca tcg cag gct aag atc gaa tgt gac      1872
         Leu Gly Phe Ser Val Glu Gly Pro Ser Gln Ala Lys Ile Glu Cys Asp
             610                 615                 620 gac aag ggc gac ggc tcc tgt gat gtg cgc tac tgg ccg cag gag gct      1920
         Asp Lys Gly Asp Gly Ser Cys Asp Val Arg Tyr Trp Pro Gln Glu Ala
         625                 630                 635                 640 ggc gag tat gcc gtt cac gtg ctg tgc aac agc gaa gac atc cgc ctc      1968
         Gly Glu Tyr Ala Val His Val Leu Cys Asn Ser Glu Asp Ile Arg Leu
                         645                 650                 655 agc ccc ttc atg gct gac atc cgt gac gcg ccc cag gac ttc cac cca      2016
         Ser Pro Phe Met Ala Asp Ile Arg Asp Ala Pro Gln Asp Phe His Pro
                     660                 665                 670 gac agg gtg aag gca cgt ggg cct gga ttg gag aag aca ggt gtg gcc      2064
         Asp Arg Val Lys Ala Arg Gly Pro Gly Leu Glu Lys Thr Gly Val Ala
                 675                 680                 685 gtc aac aag cca gca gag ttc aca gtg gat gcc aag cac ggt ggc aag      2112
         Val Asn Lys Pro Ala Glu Phe Thr Val Asp Ala Lys His Gly Gly Lys
             690                 695                 700 gcc cca ctt cgg gtc caa gtc cag gac aat gaa ggc tgc cct gtg gag      2160
         Ala Pro Leu Arg Val Gln Val Gln Asp Asn Glu Gly Cys Pro Val Glu
         705                 710                 715                 720 gcg ttg gtc aag gac aac ggc aat ggc act tac agc tgc tcc tac gtg      2208
         Ala Leu Val Lys Asp Asn Gly Asn Gly Thr Tyr Ser Cys Ser Tyr Val
                         725                 730                 735 ccc agg aag ccg gtg aag cac aca gcc atg gtg tcc tgg gga ggc gtc      2256
         Pro Arg Lys Pro Val Lys His Thr Ala Met Val Ser Trp Gly Gly Val
                     740                 745                 750 agc atc ccc aac agc ccc ttc agg gtg aat gtg gga gct ggc agc cac      2304
         Ser Ile Pro Asn Ser Pro Phe Arg Val Asn Val Gly Ala Gly Ser His
                 755                 760                 765 ccc aac aag gtc aaa gta tac ggc ccc gga gta gcc aag aca ggg ctc      2352
         Pro Asn Lys Val Lys Val Tyr Gly Pro Gly Val Ala Lys Thr Gly Leu
             770                 775                 780 aag gcc cac gag ccc acc tac ttc act gtg gac tgc gcc gag gct ggc      2400
```

```
Lys Ala His Glu Pro Thr Tyr Phe Thr Val Asp Cys Ala Glu Ala Gly
785                 790                 795                 800 cag ggg gac gtc agc atc ggc atc aag tgt gcc cct gga gtg gta ggc    2448
Gln Gly Asp Val Ser Ile Gly Ile Lys Cys Ala Pro Gly Val Val Gly
                805                 810                 815 ccc gcc gaa gct gac atc gac ttc gac atc atc cgc aat gac aat gac    2496
Pro Ala Glu Ala Asp Ile Asp Phe Asp Ile Ile Arg Asn Asp Asn Asp
            820                 825                 830 acc ttc acg gtc aag tac acg ccc cgg ggg gct ggc agc tac acc att    2544
Thr Phe Thr Val Lys Tyr Thr Pro Arg Gly Ala Gly Ser Tyr Thr Ile
        835                 840                 845 atg gtc ctc ttt gct gac cag gcc acg ccc acc agc ccc atc cga gtc    2592
Met Val Leu Phe Ala Asp Gln Ala Thr Pro Thr Ser Pro Ile Arg Val
    850                 855                 860 aag gtg gag ccc tct cat gac gcc agt aag gtg aag gcc gag ggc cct    2640
Lys Val Glu Pro Ser His Asp Ala Ser Lys Val Lys Ala Glu Gly Pro
865                 870                 875                 880 ggc ctc agt cgc act ggt gtc gag ctt ggc aag ccc acc cac ttc aca    2688
Gly Leu Ser Arg Thr Gly Val Glu Leu Gly Lys Pro Thr His Phe Thr
                885                 890                 895 gta aat gcc aaa gct gct ggc aaa ggc aag ctg gac gtc cag ttc tca    2736
Val Asn Ala Lys Ala Ala Gly Lys Gly Lys Leu Asp Val Gln Phe Ser
            900                 905                 910 gga ctc acc aag ggg gat gca gtg cga gat gtg gac atc atc gac cac    2784
Gly Leu Thr Lys Gly Asp Ala Val Arg Asp Val Asp Ile Ile Asp His
        915                 920                 925 cat gac aac acc tac aca gtc aag tac acg cct gtc cag cag ggt cca    2832
His Asp Asn Thr Tyr Thr Val Lys Tyr Thr Pro Val Gln Gln Gly Pro
    930                 935                 940 gta ggc gtc aat gtc act tat gga ggg gat ccc atc cct aag agc cct    2880
Val Gly Val Asn Val Thr Tyr Gly Gly Asp Pro Ile Pro Lys Ser Pro
945                 950                 955                 960 ttc tca gtg gca gta tct cca agc ctg gac ctc agc aag atc aag gtg    2928
Phe Ser Val Ala Val Ser Pro Ser Leu Asp Leu Ser Lys Ile Lys Val
                965                 970                 975 tct ggc ctg gga gag aag gtg gac gtt ggc aaa gac cag gag ttc aca    2976
Ser Gly Leu Gly Glu Lys Val Asp Val Gly Lys Asp Gln Glu Phe Thr
            980                 985                 990 gtc aaa tca aag ggt gct ggt ggt caa ggc aaa gtg gca tcc aag att    3024
Val Lys Ser Lys Gly Ala Gly Gly Gln Gly Lys Val Ala Ser Lys Ile
        995                 1000                1005 gtg ggc ccc tcg ggt gca gcg gtg ccc tgc aag gtg gag cca ggc ctg    3072
Val Gly Pro Ser Gly Ala Ala Val Pro Cys Lys Val Glu Pro Gly Leu
    1010                1015                1020 ggg gct gac aac agt gtg gtg cgc ttc ctg ccc cgt gag gaa ggg ccc    3120
Gly Ala Asp Asn Ser Val Val Arg Phe Leu Pro Arg Glu Glu Gly Pro
1025                1030                1035                1040 tat gag gtg gag gtg acc tat gac ggc gtg ccc gtg cct ggc agc ccc    3168
Tyr Glu Val Glu Val Thr Tyr Asp Gly Val Pro Val Pro Gly Ser Pro
                1045                1050                1055 ttt cct ctg gaa gct gtg gcc ccc acc aag cct agc aag gtg aag gcg    3216
Phe Pro Leu Glu Ala Val Ala Pro Thr Lys Pro Ser Lys Val Lys Ala
            1060                1065                1070 ttt ggg ccg ggg ctg cag gga ggc agt gcg ggc tcc ccc gcc cgc ttc    3264
Phe Gly Pro Gly Leu Gln Gly Gly Ser Ala Gly Ser Pro Ala Arg Phe
        1075                1080                1085 acc atc gac acc aag ggc gcc ggc aca ggt ggc ctg ggc ctg acg gtg    3312
Thr Ile Asp Thr Lys Gly Ala Gly Thr Gly Gly Leu Gly Leu Thr Val
    1090                1095                1100
```

```
gag ggc ccc tgt gag gcg cag ctc gag tgc ttg gac aat ggg gat ggc    3360
Glu Gly Pro Cys Glu Ala Gln Leu Glu Cys Leu Asp Asn Gly Asp Gly
1105            1110                1115                1120 aca tgt tcc gtg tcc tac gtg ccc acc gag ccc ggg gac tac aac atc    3408
Thr Cys Ser Val Ser Tyr Val Pro Thr Glu Pro Gly Asp Tyr Asn Ile
        1125                1130                1135 aac atc ctc ttc gct gac acc cac atc cct ggc tcc cca ttc aag gcc    3456
Asn Ile Leu Phe Ala Asp Thr His Ile Pro Gly Ser Pro Phe Lys Ala
            1140                1145                1150 cac gtg gtt ccc tgc ttt gac gca tcc aaa gtc aag tgc tca ggc ccc    3504
His Val Val Pro Cys Phe Asp Ala Ser Lys Val Lys Cys Ser Gly Pro
                1155                1160                1165 ggg ctg gag cgg gcc acc gct ggg gag gtg ggc caa ttc caa gtg gac    3552
Gly Leu Glu Arg Ala Thr Ala Gly Glu Val Gly Gln Phe Gln Val Asp
    1170                1175                1180 tgc tcg agc gcg ggc agc gcg gag ctg acc att gag atc tgc tcg gag    3600
Cys Ser Ser Ala Gly Ser Ala Glu Leu Thr Ile Glu Ile Cys Ser Glu
1185                1190                1195                1200 gcg ggg ctt ccg gcc gag gtg tac atc cag gac cac ggt gat ggc acg    3648
Ala Gly Leu Pro Ala Glu Val Tyr Ile Gln Asp His Gly Asp Gly Thr
                1205                1210                1215 cac acc att acc tac att ccc ctc tgc ccc ggg gcc tac acc gtc acc    3696
His Thr Ile Thr Tyr Ile Pro Leu Cys Pro Gly Ala Tyr Thr Val Thr
            1220                1225                1230 atc aag tac ggc ggc cag ccc gtg ccc aac ttc ccc agc aag ctg cag    3744
Ile Lys Tyr Gly Gly Gln Pro Val Pro Asn Phe Pro Ser Lys Leu Gln
        1235                1240                1245 gtg gaa cct gcg gtg gac act tcc ggt gtc cag tgc tat ggg cct ggt    3792
Val Glu Pro Ala Val Asp Thr Ser Gly Val Gln Cys Tyr Gly Pro Gly
    1250                1255                1260 att gag ggc cag ggt gtc ttc cgt gag gcc acc act gag ttc agt gtg    3840
Ile Glu Gly Gln Gly Val Phe Arg Glu Ala Thr Thr Glu Phe Ser Val
1265                1270                1275                1280 gac gcc cgg gct ctg aca cag acc gga ggg ccg cac gtc aag gcc cgt    3888
Asp Ala Arg Ala Leu Thr Gln Thr Gly Gly Pro His Val Lys Ala Arg
                1285                1290                1295 gtg gcc aac ccc tca ggc aac ctg acg gag acc tac gtt cag gac cgt    3936
Val Ala Asn Pro Ser Gly Asn Leu Thr Glu Thr Tyr Val Gln Asp Arg
            1300                1305                1310 ggc gat ggc atg tac aaa gtg gag tac acg cct tac gag gag gga ctg    3984
Gly Asp Gly Met Tyr Lys Val Glu Tyr Thr Pro Tyr Glu Glu Gly Leu
        1315                1320                1325 cac tcc gtg gac gtg acc tat gac ggc agt ccc gtg ccc agc agc ccc    4032
His Ser Val Asp Val Thr Tyr Asp Gly Ser Pro Val Pro Ser Ser Pro
    1330                1335                1340 ttc cag gtg ccc gtg acc gag ggc tgc gac ccc tcc cgg gtg cgt gtc    4080
Phe Gln Val Pro Val Thr Glu Gly Cys Asp Pro Ser Arg Val Arg Val
1345                1350                1355                1360 cac ggg cca ggc atc caa agt ggc acc acc aac aag ccc aac aag ttc    4128
His Gly Pro Gly Ile Gln Ser Gly Thr Thr Asn Lys Pro Asn Lys Phe
                1365                1370                1375 act gtg gag acc agg gga gct ggc acg ggc ggc ctg ggc ctg gct gta    4176
Thr Val Glu Thr Arg Gly Ala Gly Thr Gly Gly Leu Gly Leu Ala Val
            1380                1385                1390 gag ggc ccc tcc gag gcc aag atg tcc tgc atg gat aac aag gac ggc    4224
Glu Gly Pro Ser Glu Ala Lys Met Ser Cys Met Asp Asn Lys Asp Gly
        1395                1400                1405 agc tgc tcg gtc gag tac atc cct tat gag gct ggc acc tac agc ctc    4272
Ser Cys Ser Val Glu Tyr Ile Pro Tyr Glu Ala Gly Thr Tyr Ser Leu
    1410                1415                1420
```

| | |
|---|---|
| aac gtc acc tat ggt ggc cat caa gtg cca ggc agt cct ttc aag gtc<br>Asn Val Thr Tyr Gly Gly His Gln Val Pro Gly Ser Pro Phe Lys Val<br>1425                  1430                  1435                  1440 | 4320 |
| cct gtg cat gat gtg aca gat gcg tcc aag gtc aag tgc tct ggg ccc<br>Pro Val His Asp Val Thr Asp Ala Ser Lys Val Lys Cys Ser Gly Pro<br>                1445                  1450                  1455 | 4368 |
| ggc ctg agc cca ggc atg gtt cgt gcc aac ctc cct cag tcc ttc cag<br>Gly Leu Ser Pro Gly Met Val Arg Ala Asn Leu Pro Gln Ser Phe Gln<br>1460                  1465                  1470 | 4416 |
| gtg gac aca agc aag gct ggt gtg gcc cca ttg cag gtc aaa gtg caa<br>Val Asp Thr Ser Lys Ala Gly Val Ala Pro Leu Gln Val Lys Val Gln<br>                1475                  1480                  1485 | 4464 |
| ggg ccc aaa ggc ctg gtg gag cca gtg gac gtg gta gac aac gct gat<br>Gly Pro Lys Gly Leu Val Glu Pro Val Asp Val Val Asp Asn Ala Asp<br>    1490                  1495                  1500 | 4512 |
| ggc acc cag acc gtc aat tat gtg ccc agc cga gaa ggg ccc tac agc<br>Gly Thr Gln Thr Val Asn Tyr Val Pro Ser Arg Glu Gly Pro Tyr Ser<br>1505                  1510                  1515                  1520 | 4560 |
| atc tca gta ctg tat gga gat gaa gag gta ccc cgg agc ccc ttc aag<br>Ile Ser Val Leu Tyr Gly Asp Glu Glu Val Pro Arg Ser Pro Phe Lys<br>                1525                  1530                  1535 | 4608 |
| gtc aag gtg ctg cct act cat gat gcc agc aag gtg aag gcc agt ggc<br>Val Lys Val Leu Pro Thr His Asp Ala Ser Lys Val Lys Ala Ser Gly<br>    1540                  1545                  1550 | 4656 |
| ccc ggg ctc aac acc act ggc gtg cct gcc agc ctg ccc gtg gag ttc<br>Pro Gly Leu Asn Thr Thr Gly Val Pro Ala Ser Leu Pro Val Glu Phe<br>1555                  1560                  1565 | 4704 |
| acc atc gat gca aag gac gcc ggg gag ggc ctg ctg gct gtc cag atc<br>Thr Ile Asp Ala Lys Asp Ala Gly Glu Gly Leu Leu Ala Val Gln Ile<br>                1570                  1575                  1580 | 4752 |
| acg gat ccc gaa ggc aag ccg aag aag aca cac atc caa gac aac cat<br>Thr Asp Pro Glu Gly Lys Pro Lys Lys Thr His Ile Gln Asp Asn His<br>1585                  1590                  1595                  1600 | 4800 |
| gac ggc acg tat aca gtg gcc tac gtg cca gac gtg aca ggt cgc tac<br>Asp Gly Thr Tyr Thr Val Ala Tyr Val Pro Asp Val Thr Gly Arg Tyr<br>                1605                  1610                  1615 | 4848 |
| acc atc ctc atc aag tac ggt ggt gac gag atc ccc ttc tcc ccg tac<br>Thr Ile Leu Ile Lys Tyr Gly Gly Asp Glu Ile Pro Phe Ser Pro Tyr<br>    1620                  1625                  1630 | 4896 |
| cgc gtg cgt gcc gtg ccc acc ggg gac gcc agc aag tgc act gtc aca<br>Arg Val Arg Ala Val Pro Thr Gly Asp Ala Ser Lys Cys Thr Val Thr<br>1635                  1640                  1645 | 4944 |
| gtg tca atc gga ggt cac ggg cta ggt gct ggc atc ggc ccc acc att<br>Val Ser Ile Gly Gly His Gly Leu Gly Ala Gly Ile Gly Pro Thr Ile<br>                1650                  1655                  1660 | 4992 |
| cag att ggg gag gag acg gtg atc act gtg gac act aag gcg gca ggc<br>Gln Ile Gly Glu Glu Thr Val Ile Thr Val Asp Thr Lys Ala Ala Gly<br>1665                  1670                  1675                  1680 | 5040 |
| aaa gga aaa gtg acg tgc acc gtg tgc acg cct gat ggc tca gag gtg<br>Lys Gly Lys Val Thr Cys Thr Val Cys Thr Pro Asp Gly Ser Glu Val<br>                1685                  1690                  1695 | 5088 |
| gat gtg gac gtg gtg gag aat gag gac ggc act ttc gac atc ttc tac<br>Asp Val Asp Val Val Glu Asn Glu Asp Gly Thr Phe Asp Ile Phe Tyr<br>    1700                  1705                  1710 | 5136 |
| acg gcc ccc cag ccg ggc aaa tac gtc atc tgt gtg cgc ttt ggt ggc<br>Thr Ala Pro Gln Pro Gly Lys Tyr Val Ile Cys Val Arg Phe Gly Gly<br>1715                  1720                  1725 | 5184 |
| gag cac gtg ccc aac agc ccc ttc caa gtg acg gct ctg gct ggg gac<br>Glu His Val Pro Asn Ser Pro Phe Gln Val Thr Ala Leu Ala Gly Asp | 5232 |

|  |  |  |  |  |  |  |  |  |  |  |  |  |  |  |
|---|---|---|---|---|---|---|---|---|---|---|---|---|---|---|
| | | 1730 | | | | 1735 | | | | 1740 | | | | |
| cag | ccc | tcg | gtg | cag | ccc | cct | cta | cgg | tct | cag | cag | ctg | gcc | cca | cag | 5280
| Gln | Pro | Ser | Val | Gln | Pro | Pro | Leu | Arg | Ser | Gln | Gln | Leu | Ala | Pro | Gln |
| 1745 | | | | 1750 | | | | 1755 | | | | 1760 | | | |

| tac | acc | tac | gcc | cag | ggc | ggc | cag | cag | act | tgg | gcc | ccg | gag | agg | ccc | 5328
| Tyr | Thr | Tyr | Ala | Gln | Gly | Gly | Gln | Gln | Thr | Trp | Ala | Pro | Glu | Arg | Pro |
|  |  |  |  | 1765 |  |  |  |  | 1770 |  |  |  |  | 1775 |  |

| ctg | gtg | ggt | gtc | aat | ggg | ctg | gat | gtg | acc | agc | ctg | agg | ccc | ttt | gac | 5376
| Leu | Val | Gly | Val | Asn | Gly | Leu | Asp | Val | Thr | Ser | Leu | Arg | Pro | Phe | Asp |
|  |  |  |  | 1780 |  |  |  |  | 1785 |  |  |  |  | 1790 |  |

| ctt | gtc | atc | ccc | ttc | acc | atc | aag | aag | ggc | gag | atc | aca | ggg | gag | gtt | 5424
| Leu | Val | Ile | Pro | Phe | Thr | Ile | Lys | Lys | Gly | Glu | Ile | Thr | Gly | Glu | Val |
|  |  |  | 1795 |  |  |  |  | 1800 |  |  |  |  | 1805 |  |  |

| cgg | atg | ccc | tca | ggc | aag | gtg | gcg | cag | ccc | acc | atc | act | gac | aac | aaa | 5472
| Arg | Met | Pro | Ser | Gly | Lys | Val | Ala | Gln | Pro | Thr | Ile | Thr | Asp | Asn | Lys |
|  | 1810 |  |  |  |  | 1815 |  |  |  |  | 1820 |  |  |  |  |

| gac | ggc | acc | gtg | acc | gtg | cgg | tat | gca | ccc | agc | gag | gct | ggc | ctg | cac | 5520
| Asp | Gly | Thr | Val | Thr | Val | Arg | Tyr | Ala | Pro | Ser | Glu | Ala | Gly | Leu | His |
| 1825 |  |  |  | 1830 |  |  |  |  | 1835 |  |  |  |  | 1840 |  |

| gag | atg | gac | atc | cgc | tat | gac | aac | atg | cac | atc | cca | gga | agc | ccc | ttg | 5568
| Glu | Met | Asp | Ile | Arg | Tyr | Asp | Asn | Met | His | Ile | Pro | Gly | Ser | Pro | Leu |
|  |  |  |  | 1845 |  |  |  |  | 1850 |  |  |  |  | 1855 |  |

| cag | ttc | tat | gtg | gat | tac | gtc | aac | tgt | ggc | cat | gtc | act | gcc | tat | ggg | 5616
| Gln | Phe | Tyr | Val | Asp | Tyr | Val | Asn | Cys | Gly | His | Val | Thr | Ala | Tyr | Gly |
|  |  |  | 1860 |  |  |  |  | 1865 |  |  |  |  | 1870 |  |  |

| cct | ggc | ctc | acc | cat | gga | gta | gtg | aac | aag | cct | gcc | acc | ttc | acc | gtc | 5664
| Pro | Gly | Leu | Thr | His | Gly | Val | Val | Asn | Lys | Pro | Ala | Thr | Phe | Thr | Val |
|  |  |  | 1875 |  |  |  |  | 1880 |  |  |  |  | 1885 |  |  |

| aac | acc | aag | gat | gca | gga | gag | ggg | ggc | ctg | tct | ctg | gcc | att | gag | ggc | 5712
| Asn | Thr | Lys | Asp | Ala | Gly | Glu | Gly | Gly | Leu | Ser | Leu | Ala | Ile | Glu | Gly |
|  |  |  | 1890 |  |  |  |  | 1895 |  |  |  |  | 1900 |  |  |

| ccg | tcc | aaa | gca | gaa | atc | agc | tgc | act | gac | aac | cag | gat | ggg | aca | tgc | 5760
| Pro | Ser | Lys | Ala | Glu | Ile | Ser | Cys | Thr | Asp | Asn | Gln | Asp | Gly | Thr | Cys |
| 1905 |  |  |  |  | 1910 |  |  |  |  | 1915 |  |  |  |  | 1920 |

| agc | gtg | tcc | tac | ctg | cct | gtg | ctg | ccg | ggg | gac | tac | agc | att | cta | gtc | 5808
| Ser | Val | Ser | Tyr | Leu | Pro | Val | Leu | Pro | Gly | Asp | Tyr | Ser | Ile | Leu | Val |
|  |  |  |  | 1925 |  |  |  |  | 1930 |  |  |  |  | 1935 |  |

| aag | tac | aat | gaa | cag | cac | gtc | cca | ggc | agc | ccc | ttc | act | gct | cgg | gtc | 5856
| Lys | Tyr | Asn | Glu | Gln | His | Val | Pro | Gly | Ser | Pro | Phe | Thr | Ala | Arg | Val |
|  |  |  | 1940 |  |  |  |  | 1945 |  |  |  |  | 1950 |  |  |

| aca | ggt | gac | gac | tcc | atg | cgt | atg | tcc | cac | cta | aag | gtc | ggc | tct | gct | 5904
| Thr | Gly | Asp | Asp | Ser | Met | Arg | Met | Ser | His | Leu | Lys | Val | Gly | Ser | Ala |
|  |  |  | 1955 |  |  |  |  | 1960 |  |  |  |  | 1965 |  |  |

| gcc | gac | atc | ccc | atc | aac | atc | tca | gag | acg | gat | ctc | agc | ctg | ctg | acg | 5952
| Ala | Asp | Ile | Pro | Ile | Asn | Ile | Ser | Glu | Thr | Asp | Leu | Ser | Leu | Leu | Thr |
|  | 1970 |  |  |  |  | 1975 |  |  |  |  | 1980 |  |  |  |  |

| gcc | act | gtg | gtc | ccg | ccc | tcg | ggc | cgg | gag | gag | ccc | tgt | ttg | ctg | aag | 6000
| Ala | Thr | Val | Val | Pro | Pro | Ser | Gly | Arg | Glu | Glu | Pro | Cys | Leu | Leu | Lys |
| 1985 |  |  |  | 1990 |  |  |  |  | 1995 |  |  |  |  | 2000 |  |

| cgg | ctg | cgt | aat | ggc | cac | gtg | ggg | att | tca | ttc | gtg | ccc | aag | gag | acg | 6048
| Arg | Leu | Arg | Asn | Gly | His | Val | Gly | Ile | Ser | Phe | Val | Pro | Lys | Glu | Thr |
|  |  |  | 2005 |  |  |  |  | 2010 |  |  |  |  | 2015 |  |  |

| ggg | gag | cac | ctg | gtg | cat | gtg | aag | aaa | aat | ggc | cag | cac | gtg | gcc | agc | 6096
| Gly | Glu | His | Leu | Val | His | Val | Lys | Lys | Asn | Gly | Gln | His | Val | Ala | Ser |
|  |  |  | 2020 |  |  |  |  | 2025 |  |  |  |  | 2030 |  |  |

| agc | ccc | atc | ccg | gtg | gtg | atc | agc | cag | tcg | gaa | att | ggg | gat | gcc | agt | 6144
| Ser | Pro | Ile | Pro | Val | Val | Ile | Ser | Gln | Ser | Glu | Ile | Gly | Asp | Ala | Ser |
|  |  |  | 2035 |  |  |  |  | 2040 |  |  |  |  | 2045 |  |  |

| cgt | gtt | cgg | gtc | tct | ggt | cag | ggc | ctt | cac | gaa | ggc | cac | acc | ttt | gag | 6192

```
        Arg Val Arg Val Ser Gly Gln Gly Leu His Glu Gly His Thr Phe Glu
            2050                2055                2060 cct gca gag ttt atc att gat acc cgc gat gca ggc tat ggt ggg ctc         6240
Pro Ala Glu Phe Ile Ile Asp Thr Arg Asp Ala Gly Tyr Gly Gly Leu
2065                2070                2075                2080 agc ctg tcc att gag ggc ccc agc aag gtg gac atc aac aca gag gac         6288
Ser Leu Ser Ile Glu Gly Pro Ser Lys Val Asp Ile Asn Thr Glu Asp
                2085                2090                2095 ctg gag gac ggg acg tgc agg gtc acc tac tgc ccc aca gag cca ggc         6336
Leu Glu Asp Gly Thr Cys Arg Val Thr Tyr Cys Pro Thr Glu Pro Gly
    2100                2105                2110 aac tac atc atc aac atc aag ttt gcc gac cag cac gtg cct ggc agc         6384
Asn Tyr Ile Ile Asn Ile Lys Phe Ala Asp Gln His Val Pro Gly Ser
        2115                2120                2125 ccc ttc tct gtg aag gtg aca ggc gag ggc cgg gtg aaa gag agc atc         6432
Pro Phe Ser Val Lys Val Thr Gly Glu Gly Arg Val Lys Glu Ser Ile
2130                2135                2140 acc cgc agg cgt cgg gct cct tca gtg gcc aac gtt ggt agt cat tgt         6480
Thr Arg Arg Arg Arg Ala Pro Ser Val Ala Asn Val Gly Ser His Cys
2145                2150                2155                2160 gac ctc agc ctg aaa atc cct gaa att agc atc cag gat atg aca gcc         6528
Asp Leu Ser Leu Lys Ile Pro Glu Ile Ser Ile Gln Asp Met Thr Ala
                2165                2170                2175 cag gtg acc agc cca tcg ggc aag acc cat gag gcc gag atc gtg gaa         6576
Gln Val Thr Ser Pro Ser Gly Lys Thr His Glu Ala Glu Ile Val Glu
                2180                2185                2190 ggg gag aac cac acc tac tgc atc cgc ttt gtt ccc gct gag atg ggc         6624
Gly Glu Asn His Thr Tyr Cys Ile Arg Phe Val Pro Ala Glu Met Gly
    2195                2200                2205 aca cac aca gtc agc gtg aag tac aag ggc cag cac gtg cct ggg agc         6672
Thr His Thr Val Ser Val Lys Tyr Lys Gly Gln His Val Pro Gly Ser
2210                2215                2220 ccc ttc cag ttc acc gtg ggg ccc cta ggg gaa ggg gga gcc cac aag         6720
Pro Phe Gln Phe Thr Val Gly Pro Leu Gly Glu Gly Gly Ala His Lys
2225                2230                2235                2240 gtc cga gct ggg ggc cct ggc ctg gag aga gct gaa gct gga gtg cca         6768
Val Arg Ala Gly Gly Pro Gly Leu Glu Arg Ala Glu Ala Gly Val Pro
                2245                2250                2255 gcc gaa ttc agt atc tgg acc cgg gaa gct ggt gct gga ggc ctg gcc         6816
Ala Glu Phe Ser Ile Trp Thr Arg Glu Ala Gly Ala Gly Gly Leu Ala
            2260                2265                2270 att gct gtc gag ggc ccc agc aag gct gag atc tct ttt gag gac cgc         6864
Ile Ala Val Glu Gly Pro Ser Lys Ala Glu Ile Ser Phe Glu Asp Arg
        2275                2280                2285 aag gac ggc tcc tgt ggt gtg gct tat gtg gtc cag gag cca ggt gac         6912
Lys Asp Gly Ser Cys Gly Val Ala Tyr Val Val Gln Glu Pro Gly Asp
2290                2295                2300 tac gaa gtc tca gtc aag ttc aac gag gaa cac att ccc gac agc ccc         6960
Tyr Glu Val Ser Val Lys Phe Asn Glu Glu His Ile Pro Asp Ser Pro
2305                2310                2315                2320 ttc gtg gtg cct gtg gct tct ccg tct ggc gac gcc cgc cgc ctc act         7008
Phe Val Val Pro Val Ala Ser Pro Ser Gly Asp Ala Arg Arg Leu Thr
                2325                2330                2335 gtt tct agc ctt cag gag tca ggg cta aag gtc aac cag cca gcc tct         7056
Val Ser Ser Leu Gln Glu Ser Gly Leu Lys Val Asn Gln Pro Ala Ser
                2340                2345                2350 ttt gca gtc agc ctg aac ggg gcc aag ggg gcg atc gat gcc aag gtg         7104
Phe Ala Val Ser Leu Asn Gly Ala Lys Gly Ala Ile Asp Ala Lys Val
            2355                2360                2365
```

```
cac agc ccc tca gga gcc ctg gag gag tgc tat gtc aca gaa att gac    7152
His Ser Pro Ser Gly Ala Leu Glu Glu Cys Tyr Val Thr Glu Ile Asp
        2370                2375                2380 caa gat aag tat gct gtg cgc ttc atc cct cgg gag aat ggc gtt tac    7200
Gln Asp Lys Tyr Ala Val Arg Phe Ile Pro Arg Glu Asn Gly Val Tyr
2385                2390                2395                2400 ctg att gac gtc aag ttc aac ggc acc cac atc cct gga agc ccc ttc    7248
Leu Ile Asp Val Lys Phe Asn Gly Thr His Ile Pro Gly Ser Pro Phe
            2405                2410                2415 aag atc cga gtt ggg gag cct ggg cat gga ggg gac cca ggc ttg gtg    7296
Lys Ile Arg Val Gly Glu Pro Gly His Gly Gly Asp Pro Gly Leu Val
        2420                2425                2430 tct gct tac gga gca ggt ctg gaa ggc ggt gtc aca ggg aac cca gct    7344
Ser Ala Tyr Gly Ala Gly Leu Glu Gly Gly Val Thr Gly Asn Pro Ala
    2435                2440                2445 gag ttc gtc gtg aac acg agc aat gcg gga gct ggt gcc ctg tcg gtg    7392
Glu Phe Val Val Asn Thr Ser Asn Ala Gly Ala Gly Ala Leu Ser Val
2450                2455                2460 acc att gac ggc ccc tcc aag gtg aag atg gat tgc cag gag tgc cct    7440
Thr Ile Asp Gly Pro Ser Lys Val Lys Met Asp Cys Gln Glu Cys Pro
2465                2470                2475                2480 gag ggc tac cgc gtc acc tat acc ccc atg gca cct ggc agc tac ctc    7488
Glu Gly Tyr Arg Val Thr Tyr Thr Pro Met Ala Pro Gly Ser Tyr Leu
            2485                2490                2495 atc tcc atc aag tac ggc ggc ccc tac cac att ggg ggc agc ccc ttc    7536
Ile Ser Ile Lys Tyr Gly Gly Pro Tyr His Ile Gly Gly Ser Pro Phe
        2500                2505                2510 aag gcc aaa gtc aca ggc ccc cgt ctc gtc agc aac cac agc ctc cac    7584
Lys Ala Lys Val Thr Gly Pro Arg Leu Val Ser Asn His Ser Leu His
    2515                2520                2525 gag aca tca tca gtg ttt gta gac tct ctg acc aag gcc acc tgt gcc    7632
Glu Thr Ser Ser Val Phe Val Asp Ser Leu Thr Lys Ala Thr Cys Ala
2530                2535                2540 ccc cag cat ggg gcc ccg ggt cct ggg cct gct gac gcc agc aag gtg    7680
Pro Gln His Gly Ala Pro Gly Pro Gly Pro Ala Asp Ala Ser Lys Val
2545                2550                2555                2560 gtg gcc aag ggc ctg ggg ctg agc aag gcc tac gta ggc cag aag agc    7728
Val Ala Lys Gly Leu Gly Leu Ser Lys Ala Tyr Val Gly Gln Lys Ser
            2565                2570                2575 agc ttc aca gta gac tgc agc aaa gca ggc aac aac atg ctg ctg gtg    7776
Ser Phe Thr Val Asp Cys Ser Lys Ala Gly Asn Asn Met Leu Leu Val
        2580                2585                2590 ggg gtt cat ggc cca agg acc ccc tgc gag gag atc ctg gtg aag cac    7824
Gly Val His Gly Pro Arg Thr Pro Cys Glu Glu Ile Leu Val Lys His
    2595                2600                2605 gtg ggc agc cgg ctc tac agc gtg tcc tac ctg ctc aag gac aag ggg    7872
Val Gly Ser Arg Leu Tyr Ser Val Ser Tyr Leu Leu Lys Asp Lys Gly
2610                2615                2620 gag tac aca ctg gtg gtc aaa tgg ggg gac gag cac atc cca ggc agc    7920
Glu Tyr Thr Leu Val Val Lys Trp Gly Asp Glu His Ile Pro Gly Ser
2625                2630                2635                2640 ccc tac cgc gtt gtg gtg ccc tga                                     7944
Pro Tyr Arg Val Val Val Pro
            2645

<210> SEQ ID NO 14
<211> LENGTH: 2647
<212> TYPE: PRT
<213> ORGANISM: Homo sapiens
<220> FEATURE:
<223> OTHER INFORMATION: Human filamin A isoform 2
```

<400> SEQUENCE: 14

```
Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300

Thr Val Glu Thr Arg Ser Ala Gly Gln Gly Glu Val Leu Val Tyr Val
305                 310                 315                 320

Glu Asp Pro Ala Gly His Gln Glu Glu Ala Lys Val Thr Ala Asn Asn
                325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
        355                 360                 365

Pro Phe Glu Val Tyr Val Asp Lys Ser Gln Gly Asp Ala Ser Lys Val
    370                 375                 380

Thr Ala Gln Gly Pro Gly Leu Glu Pro Ser Gly Asn Ile Ala Asn Lys
385                 390                 395                 400

Thr Thr Tyr Phe Glu Ile Phe Thr Ala Gly Ala Gly Thr Gly Glu Val
```

```
                    405                 410                 415
Glu Val Val Ile Gln Asp Pro Met Gly Gln Lys Gly Thr Val Glu Pro
                420                 425                 430

Gln Leu Glu Ala Arg Gly Asp Ser Thr Tyr Arg Cys Ser Tyr Gln Pro
                435                 440                 445

Thr Met Glu Gly Val His Thr Val His Val Thr Phe Ala Gly Val Pro
            450                 455                 460

Ile Pro Arg Ser Pro Tyr Thr Val Thr Val Gly Gln Ala Cys Asn Pro
465                 470                 475                 480

Ser Ala Cys Arg Ala Val Gly Arg Gly Leu Gln Pro Lys Gly Val Arg
                485                 490                 495

Val Lys Glu Thr Ala Asp Phe Lys Val Tyr Thr Lys Gly Ala Gly Ser
            500                 505                 510

Gly Glu Leu Lys Val Thr Val Lys Gly Pro Lys Gly Glu Glu Arg Val
            515                 520                 525

Lys Gln Lys Asp Leu Gly Asp Gly Val Tyr Gly Phe Glu Tyr Tyr Pro
            530                 535                 540

Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
                565                 570                 575

Gln Lys Val Arg Ala Trp Gly Pro Gly Leu Glu Gly Gly Val Val Gly
            580                 585                 590

Lys Ser Ala Asp Phe Val Val Glu Ala Ile Gly Asp Asp Val Gly Thr
            595                 600                 605

Leu Gly Phe Ser Val Glu Gly Pro Ser Gln Ala Lys Ile Glu Cys Asp
            610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
                645                 650                 655

Ser Pro Phe Met Ala Asp Ile Arg Asp Ala Pro Gln Asp Phe His Pro
                660                 665                 670

Asp Arg Val Lys Ala Arg Gly Pro Gly Leu Glu Lys Thr Gly Val Ala
            675                 680                 685

Val Asn Lys Pro Ala Glu Phe Thr Val Asp Ala Lys His Gly Gly Lys
            690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
                725                 730                 735

Pro Arg Lys Pro Val Lys His Thr Ala Met Val Ser Trp Gly Gly Val
            740                 745                 750

Ser Ile Pro Asn Ser Pro Phe Arg Val Asn Val Gly Ala Gly Ser His
            755                 760                 765

Pro Asn Lys Val Lys Val Tyr Gly Pro Gly Val Ala Lys Thr Gly Leu
            770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                805                 810                 815

Pro Ala Glu Ala Asp Ile Asp Phe Asp Ile Ile Arg Asn Asp Asn Asp
            820                 825                 830
```

```
Thr Phe Thr Val Lys Tyr Thr Pro Arg Gly Ala Gly Ser Tyr Thr Ile
        835                 840                 845

Met Val Leu Phe Ala Asp Gln Ala Thr Pro Thr Ser Pro Ile Arg Val
        850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
                900                 905                 910

Gly Leu Thr Lys Gly Asp Ala Val Arg Asp Val Asp Ile Ile Asp His
                915                 920                 925

His Asp Asn Thr Tyr Thr Val Lys Tyr Thr Pro Val Gln Gln Gly Pro
        930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
                980                 985                 990

Val Lys Ser Lys Gly Ala Gly Gly Gln Gly Lys Val Ala Ser Lys Ile
                995                 1000                1005

Val Gly Pro Ser Gly Ala Ala Val Pro Cys Lys Val Glu Pro Gly Leu
        1010                1015                1020

Gly Ala Asp Asn Ser Val Val Arg Phe Leu Pro Arg Glu Glu Gly Pro
1025                1030                1035                1040

Tyr Glu Val Glu Val Thr Tyr Asp Gly Val Pro Val Pro Gly Ser Pro
                1045                1050                1055

Phe Pro Leu Glu Ala Val Ala Pro Thr Lys Pro Ser Lys Val Lys Ala
                1060                1065                1070

Phe Gly Pro Gly Leu Gln Gly Gly Ser Ala Gly Ser Pro Ala Arg Phe
                1075                1080                1085

Thr Ile Asp Thr Lys Gly Ala Gly Thr Gly Gly Leu Gly Leu Thr Val
        1090                1095                1100

Glu Gly Pro Cys Glu Ala Gln Leu Glu Cys Leu Asp Asn Gly Asp Gly
1105                1110                1115                1120

Thr Cys Ser Val Ser Tyr Val Pro Thr Glu Pro Gly Asp Tyr Asn Ile
                1125                1130                1135

Asn Ile Leu Phe Ala Asp Thr His Ile Pro Gly Ser Pro Phe Lys Ala
                1140                1145                1150

His Val Val Pro Cys Phe Asp Ala Ser Lys Val Lys Cys Ser Gly Pro
                1155                1160                1165

Gly Leu Glu Arg Ala Thr Ala Gly Glu Val Gly Gln Phe Gln Val Asp
        1170                1175                1180

Cys Ser Ser Ala Gly Ser Ala Glu Leu Thr Ile Glu Ile Cys Ser Glu
1185                1190                1195                1200

Ala Gly Leu Pro Ala Glu Val Tyr Ile Gln Asp His Gly Asp Gly Thr
                1205                1210                1215

His Thr Ile Thr Tyr Ile Pro Leu Cys Pro Gly Ala Tyr Thr Val Thr
                1220                1225                1230

Ile Lys Tyr Gly Gly Gln Pro Val Pro Asn Phe Pro Ser Lys Leu Gln
                1235                1240                1245
```

```
Val Glu Pro Ala Val Asp Thr Ser Gly Val Gln Cys Tyr Gly Pro Gly
    1250                1255                1260

Ile Glu Gly Gln Gly Val Phe Arg Glu Ala Thr Thr Glu Phe Ser Val
1265                1270                1275                1280

Asp Ala Arg Ala Leu Thr Gln Thr Gly Gly Pro His Val Lys Ala Arg
                1285                1290                1295

Val Ala Asn Pro Ser Gly Asn Leu Thr Glu Thr Tyr Val Gln Asp Arg
            1300                1305                1310

Gly Asp Gly Met Tyr Lys Val Glu Tyr Thr Pro Tyr Glu Glu Gly Leu
        1315                1320                1325

His Ser Val Asp Val Thr Tyr Asp Gly Ser Pro Val Pro Ser Ser Pro
    1330                1335                1340

Phe Gln Val Pro Val Thr Glu Gly Cys Asp Pro Ser Arg Val Arg Val
1345                1350                1355                1360

His Gly Pro Gly Ile Gln Ser Gly Thr Thr Asn Lys Pro Asn Lys Phe
                1365                1370                1375

Thr Val Glu Thr Arg Gly Ala Gly Thr Gly Gly Leu Gly Leu Ala Val
            1380                1385                1390

Glu Gly Pro Ser Glu Ala Lys Met Ser Cys Met Asp Asn Lys Asp Gly
        1395                1400                1405

Ser Cys Ser Val Glu Tyr Ile Pro Tyr Glu Ala Gly Thr Tyr Ser Leu
    1410                1415                1420

Asn Val Thr Tyr Gly Gly His Gln Val Pro Gly Ser Pro Phe Lys Val
1425                1430                1435                1440

Pro Val His Asp Val Thr Asp Ala Ser Lys Val Lys Cys Ser Gly Pro
                1445                1450                1455

Gly Leu Ser Pro Gly Met Val Arg Ala Asn Leu Pro Gln Ser Phe Gln
            1460                1465                1470

Val Asp Thr Ser Lys Ala Gly Val Ala Pro Leu Gln Val Lys Val Gln
        1475                1480                1485

Gly Pro Lys Gly Leu Val Glu Pro Val Asp Val Val Asp Asn Ala Asp
    1490                1495                1500

Gly Thr Gln Thr Val Asn Tyr Val Pro Ser Arg Glu Gly Pro Tyr Ser
1505                1510                1515                1520

Ile Ser Val Leu Tyr Gly Asp Glu Glu Val Pro Arg Ser Pro Phe Lys
                1525                1530                1535

Val Lys Val Leu Pro Thr His Asp Ala Ser Lys Val Lys Ala Ser Gly
            1540                1545                1550

Pro Gly Leu Asn Thr Thr Gly Val Pro Ala Ser Leu Pro Val Glu Phe
        1555                1560                1565

Thr Ile Asp Ala Lys Asp Ala Gly Glu Gly Leu Leu Ala Val Gln Ile
    1570                1575                1580

Thr Asp Pro Glu Gly Lys Pro Lys Lys Thr His Ile Gln Asp Asn His
1585                1590                1595                1600

Asp Gly Thr Tyr Thr Val Ala Tyr Val Pro Asp Val Thr Gly Arg Tyr
                1605                1610                1615

Thr Ile Leu Ile Lys Tyr Gly Gly Asp Glu Ile Pro Phe Ser Pro Tyr
            1620                1625                1630

Arg Val Arg Ala Val Pro Thr Gly Asp Ala Ser Lys Cys Thr Val Thr
        1635                1640                1645

Val Ser Ile Gly Gly His Gly Leu Gly Ala Gly Ile Gly Pro Thr Ile
    1650                1655                1660

Gln Ile Gly Glu Glu Thr Val Ile Thr Val Asp Thr Lys Ala Ala Gly
```

```
                1665                1670                1675                1680
Lys Gly Lys Val Thr Cys Thr Cys Thr Pro Asp Gly Ser Glu Val
                    1685                1690                1695

Asp Val Asp Val Val Glu Asn Glu Asp Gly Thr Phe Asp Ile Phe Tyr
                1700                1705                1710

Thr Ala Pro Gln Pro Gly Lys Tyr Val Ile Cys Val Arg Phe Gly Gly
            1715                1720                1725

Glu His Val Pro Asn Ser Pro Phe Gln Val Thr Ala Leu Ala Gly Asp
        1730                1735                1740

Gln Pro Ser Val Gln Pro Pro Leu Arg Ser Gln Gln Leu Ala Pro Gln
1745                1750                1755                1760

Tyr Thr Tyr Ala Gln Gly Gly Gln Gln Thr Trp Ala Pro Glu Arg Pro
                1765                1770                1775

Leu Val Gly Val Asn Gly Leu Asp Val Thr Ser Leu Arg Pro Phe Asp
                    1780                1785                1790

Leu Val Ile Pro Phe Thr Ile Lys Lys Gly Glu Ile Thr Gly Glu Val
                1795                1800                1805

Arg Met Pro Ser Gly Lys Val Ala Gln Pro Thr Ile Thr Asp Asn Lys
            1810                1815                1820

Asp Gly Thr Val Thr Val Arg Tyr Ala Pro Ser Glu Ala Gly Leu His
1825                1830                1835                1840

Glu Met Asp Ile Arg Tyr Asp Asn Met His Ile Pro Gly Ser Pro Leu
                1845                1850                1855

Gln Phe Tyr Val Asp Tyr Val Asn Cys Gly His Val Thr Ala Tyr Gly
                    1860                1865                1870

Pro Gly Leu Thr His Gly Val Val Asn Lys Pro Ala Thr Phe Thr Val
                1875                1880                1885

Asn Thr Lys Asp Ala Gly Glu Gly Gly Leu Ser Leu Ala Ile Glu Gly
            1890                1895                1900

Pro Ser Lys Ala Glu Ile Ser Cys Thr Asp Asn Gln Asp Gly Thr Cys
1905                1910                1915                1920

Ser Val Ser Tyr Leu Pro Val Leu Pro Gly Asp Tyr Ser Ile Leu Val
                1925                1930                1935

Lys Tyr Asn Glu Gln His Val Pro Gly Ser Pro Phe Thr Ala Arg Val
                    1940                1945                1950

Thr Gly Asp Asp Ser Met Arg Met Ser His Leu Lys Val Gly Ser Ala
                1955                1960                1965

Ala Asp Ile Pro Ile Asn Ile Ser Glu Thr Asp Leu Ser Leu Leu Thr
            1970                1975                1980

Ala Thr Val Val Pro Pro Ser Gly Arg Glu Glu Pro Cys Leu Leu Lys
1985                1990                1995                2000

Arg Leu Arg Asn Gly His Val Gly Ile Ser Phe Val Pro Lys Glu Thr
                2005                2010                2015

Gly Glu His Leu Val His Val Lys Lys Asn Gly Gln His Val Ala Ser
                    2020                2025                2030

Ser Pro Ile Pro Val Val Ile Ser Gln Ser Glu Ile Gly Asp Ala Ser
                2035                2040                2045

Arg Val Arg Val Ser Gly Gln Gly Leu His Glu Gly His Thr Phe Glu
            2050                2055                2060

Pro Ala Glu Phe Ile Ile Asp Thr Arg Asp Ala Gly Tyr Gly Gly Leu
2065                2070                2075                2080

Ser Leu Ser Ile Glu Gly Pro Ser Lys Val Asp Ile Asn Thr Glu Asp
                2085                2090                2095
```

-continued

Leu Glu Asp Gly Thr Cys Arg Val Thr Tyr Cys Pro Thr Glu Pro Gly
            2100                2105                2110

Asn Tyr Ile Ile Asn Ile Lys Phe Ala Asp Gln His Val Pro Gly Ser
            2115                2120                2125

Pro Phe Ser Val Lys Val Thr Gly Glu Gly Arg Val Lys Glu Ser Ile
            2130                2135                2140

Thr Arg Arg Arg Arg Ala Pro Ser Val Ala Asn Val Gly Ser His Cys
2145                2150                2155                2160

Asp Leu Ser Leu Lys Ile Pro Glu Ile Ser Ile Gln Asp Met Thr Ala
            2165                2170                2175

Gln Val Thr Ser Pro Ser Gly Lys Thr His Glu Ala Glu Ile Val Glu
            2180                2185                2190

Gly Glu Asn His Thr Tyr Cys Ile Arg Phe Val Pro Ala Glu Met Gly
            2195                2200                2205

Thr His Thr Val Ser Val Lys Tyr Lys Gly Gln His Val Pro Gly Ser
            2210                2215                2220

Pro Phe Gln Phe Thr Val Gly Pro Leu Gly Glu Gly Gly Ala His Lys
2225                2230                2235                2240

Val Arg Ala Gly Gly Pro Gly Leu Glu Arg Ala Glu Ala Gly Val Pro
            2245                2250                2255

Ala Glu Phe Ser Ile Trp Thr Arg Glu Ala Gly Ala Gly Gly Leu Ala
            2260                2265                2270

Ile Ala Val Glu Gly Pro Ser Lys Ala Glu Ile Ser Phe Glu Asp Arg
            2275                2280                2285

Lys Asp Gly Ser Cys Gly Val Ala Tyr Val Val Gln Glu Pro Gly Asp
            2290                2295                2300

Tyr Glu Val Ser Val Lys Phe Asn Glu Glu His Ile Pro Asp Ser Pro
2305                2310                2315                2320

Phe Val Val Pro Val Ala Ser Pro Ser Gly Asp Ala Arg Arg Leu Thr
            2325                2330                2335

Val Ser Ser Leu Gln Glu Ser Gly Leu Lys Val Asn Gln Pro Ala Ser
            2340                2345                2350

Phe Ala Val Ser Leu Asn Gly Ala Lys Gly Ala Ile Asp Ala Lys Val
            2355                2360                2365

His Ser Pro Ser Gly Ala Leu Glu Glu Cys Tyr Val Thr Glu Ile Asp
            2370                2375                2380

Gln Asp Lys Tyr Ala Val Arg Phe Ile Pro Arg Glu Asn Gly Val Tyr
2385                2390                2395                2400

Leu Ile Asp Val Lys Phe Asn Gly Thr His Ile Pro Gly Ser Pro Phe
            2405                2410                2415

Lys Ile Arg Val Gly Glu Pro Gly His Gly Gly Asp Pro Gly Leu Val
            2420                2425                2430

Ser Ala Tyr Gly Ala Gly Leu Glu Gly Gly Val Thr Gly Asn Pro Ala
            2435                2440                2445

Glu Phe Val Val Asn Thr Ser Asn Ala Gly Ala Gly Ala Leu Ser Val
            2450                2455                2460

Thr Ile Asp Gly Pro Ser Lys Val Lys Met Asp Cys Gln Glu Cys Pro
2465                2470                2475                2480

Glu Gly Tyr Arg Val Thr Tyr Thr Pro Met Ala Pro Gly Ser Tyr Leu
            2485                2490                2495

Ile Ser Ile Lys Tyr Gly Gly Pro Tyr His Ile Gly Gly Ser Pro Phe
            2500                2505                2510

-continued

```
Lys Ala Lys Val Thr Gly Pro Arg Leu Val Ser Asn His Ser Leu His
        2515            2520            2525

Glu Thr Ser Ser Val Phe Val Asp Ser Leu Thr Lys Ala Thr Cys Ala
    2530            2535            2540

Pro Gln His Gly Ala Pro Gly Pro Gly Pro Ala Asp Ala Ser Lys Val
2545            2550            2555            2560

Val Ala Lys Gly Leu Gly Leu Ser Lys Ala Tyr Val Gly Gln Lys Ser
            2565            2570            2575

Ser Phe Thr Val Asp Cys Ser Lys Ala Gly Asn Asn Met Leu Leu Val
            2580            2585            2590

Gly Val His Gly Pro Arg Thr Pro Cys Glu Glu Ile Leu Val Lys His
        2595            2600            2605

Val Gly Ser Arg Leu Tyr Ser Val Ser Tyr Leu Leu Lys Asp Lys Gly
    2610            2615            2620

Glu Tyr Thr Leu Val Val Lys Trp Gly Asp Glu His Ile Pro Gly Ser
2625            2630            2635            2640

Pro Tyr Arg Val Val Val Pro
                2645
```

METHODS AND COMPOSITIONS FOR TYPING MOLECULAR SUBGROUPS OF MEDULLOBLASTOMA

CROSS-REFERENCE TO RELATED APPLICATIONS

This application is a filing under 35 U.S.C. 371 of International Application No. PCT/US2011/054197, filed Sep. 30, 2011, which claims priority to U.S. Application No. 61/388,874, filed Oct. 1, 2010, the contents of which are herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named 430050seqlist.txt, created on Feb. 20, 2013, and having a size of 171 KB and is file concurrently with the specification. The sequence listing contained in this ASCII formatted document is part of the specification and is herein incorporated by reference in its entirety.

FIELD OF THE INVENTION

The present invention relates generally to the field of diagnostic pathology of brain tumors, more particularly to typing of molecular subgroups of medulloblastomas.

REFERENCE TO SEQUENCE LISTING SUBMITTED ELECTRONICALLY

The official copy of the sequence listing is submitted electronically via EFS-Web as an ASCII formatted sequence listing with a file named 410091 SEQLIST.txt, created on Sep. 26, 2011, and having a size of 175,428 bytes and is filed concurrently with the specification. The sequence listing contained in this ASCII formatted document is part of the specification and is herein incorporated by reference in its entirety.

BACKGROUND OF THE INVENTION

Medulloblastoma, the most common type of primitive neuroectodermal tumor (PNET), is a malignant embryonal tumor of the nervous system, occurring mainly in children and accounting for 25% of all pediatric brain tumors. Most medulloblastoma patients are diagnosed between five and ten years of age (Louis et al. (2007) *Acta Neuropathol.* 114(2): 97-109), and these tumors occur more often in males than in females. Few medulloblastomas occur under the age of one. These tumors arise in the cerebellum, a region of the brain that continues to develop after birth, during the first two years of human life.

Typically a childhood tumor, medulloblastoma does occur at a very low frequency in adults. Of all medulloblastomas diagnosed in the United States less than ten percent (5%) are found in adults, usually between the ages of 20-44 years. The incidence in adults sharply decreases in frequency after age 45, with very few older adults having this tumor.

A preliminary diagnosis of medulloblastoma is based on clinical symptoms and signs, supplemented by radiological investigations (neuroimaging).

Current treatment regimens for medulloblastoma depend on the age of the patient and the size and/or position of the tumor. In most cases, surgery is performed to remove as much of the tumor as possible with minimal neurological damage. In a minority of patients, the tumor has grown into the brain stem making total removal impossible. Surgery is then followed by radiation therapy to the brain and spinal cord to minimize spreading through the CSF and possible regrowth. Chemotherapy is also given to further deter the spread or regrowth of tumor cells.

The success of current treatments depends, inter alia, upon the accurate staging and subtyping of medulloblastomas. Generally, staging is dependent upon the extent of resection, evidence of tumor spread as determined by radiography, and cerebrospinal fluid (CSF) cytology and is graded according to the Chang system (M0-M4). Patients are categorized as low-risk if they undergo gross total tissue resection, with no radiographic evidence of spread, and show no malignant cells on CSF cytology.

Further classification of medulloblastoma depends upon detailed pathologic examination. Histologically, medulloblastomas are divided into five categories according to the WHO classification of tumors of the nervous system based on their morphology, the classic tumor and four variants: desmoplastic/nodular (D/N), medulloblastoma with extensive nodularity (MBEN), large cell medulloblastoma and anaplastic medulloblastoma. The last of these two are sometimes combined into a large cell/anaplastic (LC/A) category, because of their shared aggressive behavior (Kleihues et al. (2002) *J. Neuropath. Exp. Neurol.* 61(3):215-225).

Although significant strides have been made in diagnosing and treating these tumors, medulloblastomas remain one of the most challenging pediatric tumors, and improved survival rates have come at a significant cost with significant long-term cognitive and/or neuroendocrine adverse effects among survivors. Presently, identification of pathobiologic/molecular correlates of heterogeneous behavior that could facilitate therapeutic stratification and the application of novel therapies for children with brain tumors, including medulloblastoma, remains a major challenge in the field.

Specifically, cells within medulloblastomas that survive radiation treatment can repopulate the tumor, for example, via activation of the phosphatidylinositol-3 (PI3) kinase pathway. Thus, effective and optimal techniques to identify, type/characterize, and then target these cells to eliminate the tumor in its entirety while sparing the rest of the brain are still needed. In order for the appropriate therapy to be effectively applied, it is necessary that the type of medulloblastoma present in patients be determined as soon as possible. Therefore, the development of novel ways to type medulloblastomas that may benefit from a distinct therapeutic protocol and, thus improve outcome of patients with these specific medulloblastomas, are also urgently needed.

SUMMARY OF THE INVENTION

In the past year researchers in the field of medulloblastoma have defined four molecular subgroups of the tumor. (See Northcott P A, Korshunov A, Witt H, et al: Medulloblastoma comprises four distinct molecular variants. *J Clin Oncol* 29:1408-14, 2011; Ellison D W: Childhood medulloblastoma: novel approaches to the classification of a heterogeneous disease. *Acta Neuropathol* 120:305-16, 2010; and Ellison D W, Dalton J, Kocak M, et al: Medulloblastoma: clinicopathological correlates of SHH, WNT, and non-SHH/WNT molecular subgroups. *Acta Neuropathol* 121:381-96, 2011.) Two of these medulloblastoma subgroups are characterized by aberrant upregulation of either the WNT or Sonic Hedgehog (SHH) cell signaling pathway. The other two (non-SHH/WNT) subgroups are not obviously characterized by dysfunction of a cell signaling pathways, although one is associated with overexpression of the MYC gene. These four molecular subgroups of medulloblastoma are associated with different clinical and histopathological characteristics; e.g., WNT pathway tumors present at a slightly older age among children, are nearly always classic tumors, and have a good outcome with current therapies.

Inventors have tailored therapeutic approaches to medulloblastoma based on a combination of clinical, pathological, and molecular assessments, including the separation of WNT, SHH, and non-SHH/WNT tumors. Northcott P A, Korshunov A, Witt H, et al: Medulloblastoma comprises four distinct molecular variants. *J Clin Oncol* 29:1408-14, 2011; Ellison D W: Childhood medulloblastoma: novel approaches to the classification of a heterogeneous disease. *Acta Neuropathol* 120:305-16, 2010; Ellison D W, Dalton J, Kocak M, et al: Medulloblastoma: clinicopathological correlates of SHH, WNT, and non-SHH/WNT molecular subgroups. *Acta Neuropathol* 121:381-96, 2011

Immunohistochemical methods and compositions for the typing of molecular subgroups of medulloblastomas are provided. The methods comprise determining a protein expression profile for a sample obtained from a medulloblastoma by determining presence or absence of expression of at least two biomarker proteins selected from the group consisting of β-catenin, YAP1, GAB1, and filamin A, and typing the medulloblastoma as a WNT pathway tumor, a SHH pathway tumor, or a non-WNT/non-SHH tumor based on this protein expression profile. In some embodiments, expression of at least one of these four biomarker proteins are detected, preferably at least two of these four biomarker proteins is detected, and more preferably where one of the two biomarker proteins is either β-catenin or GAB1. In other embodiments, expression of three of these four biomarker proteins is detected. In yet other embodiments, expression of all four biomarker proteins is detected.

The present invention also provides immunohistochemical methods and compositions for typing a medulloblastoma as a SHH pathway tumor or a non-SHH tumor based on the detection of expression of GAB1 alone within a tumor sample, for typing a medulloblastoma as a non-WNT/non-SHH tumor based on the detection of negative expression of filamin A or YAP1 within a tumor sample, and for typing a medulloblastoma as a WNT pathway tumor based on detection of positive nuclear expression of β-catenin within a tumor sample.

In some embodiments, these immunohistochemical methods comprise evaluating a medulloblastoma tissue sample by first contacting a tissue sample obtained from a medulloblastoma with at least two antibodies, where each of these antibodies specifically binds to a distinct biomarker protein selected from the group consisting of β-catenin, YAP1, GAB1, and filamin A, determining a protein expression profile for the sample based on the detection of binding of these antibodies to their respective biomarker proteins, and typing the medulloblastoma based on this protein expression profile. In some embodiments, the methods utilize a combination of two antibodies, three antibodies, or four antibodies, each of which specifically binds to a distinct biomarker protein selected from the group consisting of β-catenin, YAP1, GAB1, and filamin A.

Kits for typing a medulloblastoma according to these three molecular subgroups are provided. The kits comprise at least two antibodies, wherein each of said antibodies specifically binds to a distinct biomarker protein selected from the group consisting of β-catenin, YAP1, GAB1, and filamin A. In some embodiments, the kits comprise two antibodies, three antibodies, or four antibodies, each of which specifically binds to a distinct biomarker protein selected from the group consisting of β-catenin, YAP1, GAB1, and filamin A. The kits can optionally comprise one or more of instructions for use, reagents for detecting antibody binding to one or more of said biomarker proteins, and one or more positive control samples.

The medulloblastoma typing methods and kits of the invention permit the rapid and accurate identification of medulloblastomas belonging to these three molecular subgroups. In so doing, the present invention also provides for the identification of subjects with a medulloblastoma that would benefit from known therapies, as well as the selection of subjects for enrollment into clinical trials designed to assess efficacy of new therapies that target the WNT or SHH signaling pathways, or target treatment of medulloblastomas that are not regulated by either of these cell signaling pathways. Accordingly, the present invention encompasses methods and compositions useful for typing medulloblastomas and identifying appropriate and effective therapies for subjects afflicted with this disease.

DESCRIPTION OF THE FIGURES

FIG. 1 shows a table representing the validation set for the immunohistochemical (IHC) panel to distinguish WNT pathway, SHH pathway, and non-WNT/non-SHH medulloblastomas. Antibodies to four proteins are used: β-catenin, filamin A, GAB1, and YAP1.

DETAILED DESCRIPTION OF THE INVENTION

Overview

The present invention is directed to immunohistochemical methods and kits for typing medulloblastomas, more particularly for typing these tumors as being associated with one of the following molecular subgroups: (1) medulloblastomas that are associated with activation of the WNT signaling pathway, hereinafter referred to as "WNT pathway tumors"; (2) medulloblastomas that are associated with activation of the sonic hedgehog (SHH) signaling pathway, hereinafter referred to as "SHH pathway tumors"; and (3) medulloblastomas that are not associated with dysregulation of either the WNT signaling pathway or SHH signaling pathway, hereinafter referred to as "non-WNT/non-SHH tumors."

The immunohistochemical methods and kits of the present invention utilize the biomarker proteins, GAB1, filamin A, or a unique combination of at least two biomarker proteins selected from the group consisting of β-catenin, YAP1, GAB1, and filamin A in order to type medulloblastomas into one of these three molecular subgroups. In this manner, a sample obtained from a medulloblastoma is analyzed to determine a protein expression profile, where analysis comprises detecting expression of at least two of these biomarker proteins. The resulting protein expression profile is predictive of the molecular subgroup to which the medulloblastoma belongs. In some embodiments, expression is detected with the use of at least two antibodies, each of which specifically binds to one of these four biomarker proteins.

The medulloblastoma typing methods and kits of the invention advantageously use surrogate biomarkers of these cell signaling pathways that can readily be detected in fixed tissue samples, including formalin-fixed paraffin wax-embedded (FFPE) tissue samples. The medulloblastoma typing methods and kits provided herein find use in identifying subjects with medulloblastomas that would benefit from standard treatment protocols, 'low-risk' tumor protocols, or which need more aggressive therapeutic intervention for a 'high-risk' tumor. Thus, the present invention also provides means for selecting subjects for clinically proven treatment regimens for medulloblastomas, and for enrolling subjects into clinical trials aimed at testing new treatment regimens for medulloblastomas.

By "medulloblastoma" is intended a malignant primary embryonal tumor that originates in the cerebellum, the part of the brain that controls walking, balance, and fine motor coordination. It is the most common type of embryonal tumor, the latter of which arise from "embryonal" or immature cells at an early stage of their development. These rapidly growing tumors may spread through the cerebrospinal fluid, metastasizing to different locations in the brain and spine. The clinical manifestations and diagnosis of a medulloblastoma are well known to those of skill in the art. Medulloblastomas are known to be molecularly distinct from other histologically similar embryonal tumors such as supratentorial primitive neuroectodermal tumors, central neuroblastomas, ependymoblastomas, medulloepithelioma, and atypical teratoid/rhabdoid tumors.

Recent studies aimed at classifying medulloblastomas on the basis of their gene expression profiles have identified several distinct molecular subgroups, one of which is characterized by activation of the WNT cell signaling pathway (WNT pathway tumors), another of which is characterized by activation of the SHH cell signaling pathway (SHH pathway tumors), along with a third molecular subgroup of tumors, which are not obviously associated with abnormalities of any specific cell signaling pathway (non-WNT/non-SHH tumors) (see Thompson et al. (2006) *J. Clin. Oncol.* 24(12):1924-1930; Northcott P A, Korshunov A, Witt H, et al: Medulloblastoma comprises four distinct molecular variants. *J Clin Oncol* 29:1408-14, 201; and Ellison D W: Childhood medulloblastoma: novel approaches to the classification of a heterogeneous disease. *Acta Neuropathol* 120:305-16, 2010).

The non-WNT/non-SHH tumors cluster into two, three, or four further subgroups. These non-WNT/non-SHH tumor subgroups are also more closely related to each other on principal components analysis than they are to WNT pathway tumors or SHH pathway tumors. For purposes of the present invention, those medulloblastomas not regulated by the WNT signaling pathway or the SHH signaling pathway are treated as one molecular subgroup, i.e., non-WNT/non-SHH tumors. The present invention provides methods and compositions for typing medulloblastomas according to these three molecular subgroups. Notably, the typing methods of the present invention can be utilized to type medulloblastomas that cannot be distinguished from other medulloblastomas on the basis of basic clinical or histopathological information (for example, age at diagnosis, sex, and histologic subtype).

In this manner, the present invention provides methods and kits for typing of medulloblastomas that are regulated by activation of the WNT signaling pathway. Such medulloblastomas are referred to herein as "WNT pathway tumors." Activation of the WNT signaling pathway defines a distinct molecular subgroup of medulloblastomas that harbor a characteristic genomic profile, frequently involving monosomy of chromosome 6 and activating mutations in CTNNB1, and which are generally independent of tumors containing common characteristic medulloblastoma defects, such as chromosome 17 aberrations (Thompson et al. (2006) *J. Clin. Oncol.* 24(12):1924-1930). Upregulation of CDH1, APC, DKK1, DKK2, DKK4, WNT inhibitory factor 1 (WIF), LEF1, CCDN1, and GAD1 may also be present in medulloblastomas that are regulated by the WNT signaling pathway (see, for example, Nikuševa-Martić et al. (2007) *Pathology—Research and Practice* 203:779-787; Thompson et al. (2006) *J. Clin. Oncol.* 24(12):1924-1930; and Rogers et al. (2009) *Brit. J. Cancer.* 100:1292-1302).

In other embodiments, the present invention provides methods and kits for typing of medulloblastomas that are characterized by activation of the SHH signaling pathway. Such medulloblastomas are referred to herein as "SHH pathway tumors." The SHH signaling pathway, which stimulates proliferation of cerebellar granule cells during cerebellar development, has been implicated in the pathogenesis and etiology of medulloblastoma, particularly those of the desmoplastic/nodular (D/N) histologic subtype. PTCH1 loss-of-function mutations contribute to approximately 10-20% of sporadic medulloblastoma cases, and mutations in SMO and SUFU also occur, though these are rare. Upregulation of GLI1 and GLI2 (Teglund et al. (2010) *Biochim. Biophys. Acta*. 1505:181-208) and ATOH1, PTCH2, and SFRP1 have also been shown (Thompson et al. (2006) *J. Clin. Oncol.* 24(12):1924-1930).

The medulloblastoma typing methods and kits described herein can be utilized to type tumors as belonging to the third molecular subgroup referred to herein as "non-WNT/non-SHH tumors." As noted above, this molecular subgroup of medulloblastomas is not obviously associated with abnormalities in either the WNT or SHH signaling pathways.

The methods and kits of the present invention encompass the typing of medulloblastomas as WNT pathway tumors, SHH pathway tumors, or non-WNT/non-SHH tumors that may also be classified based on histology, including general architectural and cytological features such as nodule formation, differentiation along neuronal (neurocytic/ganglionic) and astroctyic lines, and large cell or anaplastic phenotypes. Thus, the methods of the present invention are applicable to medulloblastomas of the classic, desmoplastic/nodular (D/N), large cell (LC), or anaplastic (A) histologic subtypes, as well as medulloblastomas with extensive nodularity (MBENs), medulloblastomas with neuroblastic or neuronal differentiation, and medulloblastomas with glial differentiation. Medulloblastomas of the classic histologic subtype consist of sheets of densely packed, small round cells with a high nuclear:cytoplasmic ratio, as seen with microscopic examination. Medulloblastomas of the desmoplastic/nodular histologic subtype are characterized by scattered islands of neurocytic cells. Internodular desmoplasia is required for the diagnosis of D/N medulloblastomas, including the paucinodular D/N variant, and MBEN. Anaplastic medulloblastomas show marked cytological pleomorphism across most of their area, in association with high mitotic and apoptotic counts. A large-cell medulloblastoma is defined by its groups of uniform large round cells with a single nucleolus, in most cases admixed with groups of anaplastic cells. Medulloblastomas with neuroblastic or neuronal differentiation refer to tumors in which the tumor cells appear similar to abnormal nerve cells; and medulloblastomas with glial differentiation refer to tumors having cells that appear similar to the supportive glial brain cells. MBENs mainly occur in young children and are clearly associated with a more favorable outcome, whereas patients with LC/A medulloblastomas generally have a poor outcome. The D/N histologic subtype has a more favorable outcome than that of classic medulloblastomas among infants. The typing methods of the present invention advantageously can be used to determine whether a medulloblastoma would best be treated by standard, 'low-risk', or 'high-risk' protocols (i.e., surgery, radiation, chemotherapy, and combinations thereof) or by therapeutics that target the WNT or SHH signaling pathway, irrespective of the histologic subtype of a medulloblastoma.

Furthermore, the medulloblastoma typing methods and kits of the invention are applicable to tumors defined according to the "TNM" classification scheme, a standardized system for medulloblastoma cancer staging that was developed by the American Joint Committee on Cancer (AJCC) and/or according to the Chang classification system of grading medulloblastoma. (See Laurent J P, Chang C H, Cohen M E. A classification system for primitive neuroectodermal tumors (medulloblastoma) of the posterior fossa. *Cancer.* 1985 Oct. 1; 56(7 Suppl):1807-9). According to TNM classification scheme, a subject diagnosed with a medulloblastoma is assessed for primary tumor size (T), regional lymph node status (N), and the presence/absence of distant metastasis (M) and then classified into stages 0-IV based on this combination of factors. In this system, primary tumor size is categorized on a scale of 0-4 (T0=no evidence of primary tumor; T1=<3 cm; T2=>3 cm; T3=>3 cm in diameter with definite spread into the brain stem; T4=>3 cm in diameter with extension up past the aqueduct of Sylvius and/or down past the foramen magnum). Lymph node status is classified as N0-N3 (N0=regional lymph nodes are free of metastasis; N1-N3=degree of metastasis to lymph nodes and distant sites). Metastasis is categorized (by TNM and Chang classification systems) as M0=no evidence of metastasis; M1=tumor cells found in cerebrospinal fluid (by lumbar puncture and cytology study); M2=tumor beyond primary site but still intracranial; M3=tumor deposits ("seeds") in spine area that are easily seen on MRI; M4=tumor spread to areas outside the CNS (outside both brain and spine).

The medulloblastomas to be typed in accordance with the methods and compositions of the invention can be associated with one or more genetic abnormalities. Thus, for example, 33-50% of all pediatric medulloblastomas contain chromosome 17 copy number abnormalities, in particular i17q, an isochromosome on the long arm of chromosome 17. Genetic abnormalities found on chromosomes 1, 6, 7, 8, 9, 10q, 11, and 16 may also be involved. Thus, in some embodiments of the present invention, the medulloblastoma to be typed is associated with genetic abnormalities on one or more of chromosomes 1, 6, 7, 8, 9, 10q, 11, 16, and 17, as well as amplification of the MYC or MYCN genes.

Methods for Typing Medulloblastomas

The present invention thus provides immunohistochemical methods for typing medulloblastomas according to one of the three molecular subgroups previously identified by gene expression profiling (see, for example, Thompson et al. (2006) *J. Clin. Oncol.* 24(12):1924-1930; and Ellison D W, Dalton J, Kocak M, et al: Medulloblastoma: clinicopathological correlates of SHH, WNT, and non-SHH/WNT molecular subgroups. *Acta Neuropathol* 121:381-96, 2011, herein incorporated by reference in their entirety), i.e., WNT pathway tumors, SHH pathway tumors, and non-WNT/non-SHH tumors. ( ). These immunohistochemical methods reliably predict whether a medulloblastoma is associated with genomic abnormalities resulting in activation of the WNT signaling pathway, genomic abnormalities resulting in activation of the SHH signaling pathway, or genomic abnormalities that are not associated with either of these two cell signaling pathways.

In accordance with some embodiments of the present invention, the immunohistochemical methods for typing of a medulloblastoma as a WNT pathway tumor, a SHH pathway tumor, or a non-WNT/non-SHH tumor comprise determining a protein expression profile for a sample obtained from a medulloblastoma by detecting expression of at least two biomarker proteins selected from the group consisting of β-catenin, YAP1, GAB1, and filamin A.

By "detecting expression" is intended determining the quantity or presence of a biomarker protein. Thus, "detecting expression" encompasses instances where a biomarker protein is determined not to be expressed, not to be detectably expressed, expressed at a low level, expressed at a normal level, or overexpressed. "Detecting expression" also encompasses detecting expression in the nucleus or cytoplasm. Detection of expression of these biomarker proteins within a sample obtained from a medulloblastoma can be achieved using any protein detection means known to those of skill in the art of immunohistochemistry, including those detection methods described herein below. Detecting expression of at least two of these four biomarker proteins within a medulloblastoma sample yields a unique protein expression profile that is predictive of the molecular subgroup to which the analyzed medulloblastoma belongs. In this manner, the medulloblastoma typing methods of the invention distinguish between WNT pathway tumors, SHH pathway tumors, and non-WNT/non-SHH tumors without having to resort to more complex and costly gene expression profiling. Furthermore, these particular biomarker proteins provide two advantages for immunohistochemical typing of medulloblastomas into these molecular subgroups. First, expression of these particular biomarker proteins is essentially either "on" or "off" within the cells or identified subcellular compartments of the medulloblastoma sample such that their expression can readily be scored as either "positive" or "negative" by anyone of skill in the field with the following qualifications.

With respect to filamin A, positive expression observed in WNT pathway tumor samples is generally weaker than positive expression observed in SHH pathway tumor samples. With respect to β-catenin, WNT pathway tumors generally show nearly all cells with nucleopositive (i.e., positive nuclear expression) immunoreactivity for β-catenin. However, about one-third of WNT pathway tumors show patchy nucleopositive immunoreactivity for β-catenin, but at least 10% of tumor cells are nucleopositive in these samples. There are also very rare non-WNT pathway medulloblastomas with scattered nucleopositive immunoreactivity for β-catenin amounting to less than 1% of tumor cells, which can easily be distinguished from WNT pathway tumor samples. Second, all of these biomarker proteins are readily detectable by immunological techniques even in formalin-fixed paraffin-wax embedded tissue samples.

β-catenin is a critical downstream effector of the WNT/Wg signaling pathway. This protein is encoded by the CTNNB1 gene (see, for example, Kraus et al. (1994) *Genomics* 23(1): 272-274; see also, GenBank Accession Nos. NP_001091680 (SEQ ID NO:2, setting forth the 781-aa protein sequence) and NM_001098210 (coding sequence is nucleotides 269-2614; see SEQ ID NO:1, setting forth this coding sequence). It is expressed as both cytoplasmic and nuclear forms. Cytoplasmic β-catenin is inactive and is regulated by a multimeric protein complex consisting of APC, GSK-3β, and AXIN. In its inactive state, β-catenin is phosphorylated by GSK-3β, rendering it degradable by the ubiqitin-proteasome pathway. During activation of the WNT/Wg signaling pathway, the multimeric complex is destabilized, leading to the upregulation of β-catenin, promoting its translocation to the nucleus. In the nucleus, β-catenin acts as a co-activator of Tcf/Lef transcription factors, which regulate genes involved in cell-cycle progression, apoptosis, and differentiation. Positive nuclear β-catenin expression is therefore a biomarker for activation of the WNT/Wg signaling pathway. β-catenin has been shown to be expressed in the nucleus of medulloblastoma cells, and its positive nuclear expression has further been shown to be a prognostic marker in medulloblastoma (Ellison et al. (2005) *J. Clin. Oncol.* 23(31):7951-7957).

YAP1, or Yes-associated protein 1, is a 65 kDa protein encoded by the YAP1 gene (see, for example, Sudol et al.

(1995) *J. Biol. Chem.* 270(24):14733-14741; see also GenBank Accession Nos. NP_001123617 (SEQ ID NO:4, setting forth the isoform 1 variant having a 504-aa protein sequence) and NM_001130145 (coding sequence shown in nucleotides 389-1903; see SEQ ID NO:3, setting forth this coding sequence); and GenBank Accession Nos. NP_006097 (SEQ ID NO:6, setting forth the isoform 2 variant having a 450-aa protein sequence) and NM_006106 (coding sequence is nucleotides 389-1741; see SEQ ID NO:5, setting forth this coding sequence)). YAP1 can act both as a co-activator and a co-repressor and is the critical downstream regulatory target in the Hippo signaling pathway that plays a pivotal role in organ size control and tumor suppression by restricting proliferation and promoting apoptosis. The core of this pathway is composed of a kinase cascade wherein MST1/MST2, in complex with its regulatory protein SAV1, phosphorylates and activates LATS1/2 in complex with its regulatory protein MOB1, which in turn phosphorylates and inactivates YAP1 oncoprotein. YAP1 plays a key role in controlling cell proliferation in response to cell contact. Phosphorylation by LATS1/2 inhibits its translocation into the nucleus to regulate cellular genes important for cell proliferation, cell death, and cell migration. Up-regulation of YAP1 has been shown in a subset of human medulloblastomas, in particular, those medulloblastomas regulated by the SHH and WNT pathways. YAP1 is also upregulated in cerebellar granule neuron precursors (CGNPs), which are proposed cells of origin for subtypes of medulloblastomas, possibly through the activation of TEAD1 (Fernandez-L et al. (2009) *Genes & Development* 23:2739-2741).

GAB1, or GRB2-associated-binding protein 1, is a member of the IRS1-like multisubstrate docking protein family, and is encoded by the GAB1 gene (see, for example, Holgado-Madruga et al. (1996) *Nature* 379:560-564; see also GenBank Accession Nos. NP_997006 (SEQ ID NO:8, setting forth the "isoform a" variant having a 724-aa protein sequence) and NM_207123 (coding sequence shown in nucleotides 360-2534; see SEQ ID NO:7, setting forth this coding sequence); and GenBank Accession Nos. NP_002030 (SEQ ID NO:10, setting forth the "isoform b" variant having a 694-aa protein sequence) and NM_002039 (coding sequence shown in nucleotides 360-2444; see SEQ ID NO:9, setting forth this coding sequence)). GAB1 is an important mediator of branching tubulogenesis and plays a central role in cellular growth response, transformation, and apoptosis. Two transcript variants of this gene are known and encode different isoforms. GAB1 is a docking protein that recruits PI3 kinase and other effector proteins in response to the activation of many receptor tyrosine kinases (RTKs). The primary mechanism of EGF-induced stimulation of the PI3 kinase/Akt anti-apoptotic pathway occurs via the docking protein GAB1. The protein GRB2 plays a central role in signaling by RTKs, where its SH2 domain binds to the receptor and its two SH3 domains link to effectors. One target effector is SOS, where GRB2 links RTKs with the Ras signaling pathway. The SH3 domains can also couple to other signaling proteins, including Vav, c-Abl and dynamin. GAB1 is expressed in medulloblastomas and shares amino-acid homology and several structural features with IRS-1, which is a substrate of the EGF and insulin receptors, and can act as a docking protein for several SH2-containing proteins known to be expressed in medulloblastomas. Expression of GAB1 enhances cell growth and transformation (see, for example, Holgrado-Madruga et al. (1996) *Nature* 379:560-564).

Filamins are a family of high molecular mass cytoskeletal proteins that organize filamentous actin in networks and stress fibers and are responsible for anchoring various transmembrane proteins to the actin cytoskeleton and providing a scaffold for a wide range of cytoplasmic signaling proteins. Filamin A is a 280-kDa protein that is encoded by the FLNA gene (see, for example, Gorlin et al. (1993) *Genomics* 17(2): 496-498; see also, GenBank Accession Nos. NP_001447 (SEQ ID NO:12, setting forth the "isoform 1" variant having a 2639-aa protein sequence) and NM_001456 (coding sequence shown in nucleotides 250-8169; see SEQ ID NO:11, setting forth this coding sequence); and GenBank Accession Nos. NP_001104026 (SEQ ID NO:14, setting forth the "isoform 2" 2647-aa protein sequence) and NM_001110556 (coding sequence shown in nucleotides 250-8193; see SEQ ID NO:13, setting forth this coding sequence)). Remodeling of the cytoskeleton is central to the modulation of cell shape and migration. Filamin A is a widely expressed protein that regulates reorganization of the actin cytoskeleton by interacting with integrins, transmembrane receptor complexes, and second messengers. Upregulation or overexpression of filamin A has been observed in various types of cancer. The direct association of filamin A with medulloblastomas has not been previously reported.

Thus, in accordance with these immunohistochemical methods of the present invention, typing of a medulloblastoma as a WNT pathway tumor, a SHH pathway tumor, or a non-WNT/non-SHH tumor comprises determining a protein expression profile for tumor cells in a sample obtained from a medulloblastoma by detecting expression of at least two biomarker proteins selected from the group consisting of β-catenin, YAP1, GAB1, and filamin A.

The unique protein expression profiles displayed by medulloblastomas falling within these three molecular subgroups are summarized in Table 1 below.

TABLE 1

Immunohistochemical protein expression profiles among tumor cells predictive of WNT pathway medulloblastomas (WNT), SHH pathway medulloblastomas (SHH), and non-WNT/non-SHH medulloblastomas (Other).

| Molecular | β-catenin | | | | |
|---|---|---|---|---|---|
| Subgroup | N | C | YAP1 | GAB1 | Filamin A |
| WNT | + | + | + | − | + |
| SHH | − | + | + | + | + |
| Other | − | + | − | − | − |

For YAP1, GAB1, and filamin A, "+" = positive expression, scored by detection in at least 50% of cells in field of view and "−" = negative expression, scored by detection in less than 50% of cells in field of view.
For β-catenin expression, "N" denotes nuclear expression, where "+" = positive expression, scored by detection in at least 10% of the nuclei in field of view and "−" = negative expression, scored by detection in less than 10% of the nuclei in field of view; "C" denotes cytoplasmic expression.

As evidenced by Table 1, in those embodiments of the invention where the protein expression profile is based on the detection of expression of two biomarker proteins, one of the biomarker proteins is either β-catenin or GAB1, as detection of expression of either of these biomarker profiles in combination with detection of expression of one of the other three biomarker proteins yields a protein expression profile that distinguishes between WNT pathway tumors, SHH pathway tumors, and non-WNT/non-SHH tumors.

Also, as can be seen from Table 1, β-catenin expression is generally positive in the cytoplasm of cells of medulloblastomas, regardless of these three molecular subgroups. In contrast, positive expression of β-catenin within the nuclei of cells of a medulloblastoma is predictive of a WNT pathway tumor.

Where the protein expression profile of a medulloblastoma sample is determined by detecting expression of β-catenin and at least one of YAP1, GAB1, or filamin A, a protein expression profile characterized by positive nuclear expression of β-catenin is predictive of a WNT pathway medulloblastoma. If, however, the protein expression profile of a medulloblastoma sample is characterized by negative nuclear expression of β-catenin, detecting expression of any one of YAP1, GAB1, filamin A, or a combination thereof within the medulloblastoma sample allows for the determination of a unique protein expression profile that distinguishes between SHH pathway tumors and non-WNT/non-SHH tumors. In this manner, medulloblastomas regulated by activation of the SHH signaling pathway exhibit a protein expression profile that is characterized not only by negative nuclear expression of β-catenin, but also positive expression of any one or more of YAP1, GAB1, or filamin A. In contrast, medulloblastomas that have no association with the WNT or SHH signaling pathways exhibit a protein expression profile among tumor cells that is characterized by negative nuclear expression of β-catenin and negative expression of YAP1, GAB1, and filamin A.

Alternatively, where the protein expression profile of a medulloblastoma sample is determined by detecting expression of GAB1 and expression of at least one of β-catenin, YAP1, or filamin A, a protein expression profile characterized by positive expression of GAB1 is predictive of a SHH pathway medulloblastoma. If, however, the protein expression profile of a medulloblastoma sample is characterized by negative expression of GAB1, detecting positive nuclear expression of β-catenin is predictive of a WNT pathway medulloblastoma. Where the protein expression profile is characterized by negative expression of GAB1 and negative nuclear expression of β-catenin, the medulloblastoma is typed as a non-WNT/non-SHH tumor.

In like manner, where the protein expression profile of a medulloblastoma sample is determined by detecting expression of YAP1 and at least one of β-catenin, GAB1, or filamin A, a protein expression profile characterized by negative expression of YAP1 is predictive of a non-WNT/non-SHH pathway tumor. If, however, the protein expression profile is characterized by positive YAP1 expression, typing of the analyzed medulloblastoma as a SHH pathway or WNT pathway tumor is readily achieved by the detection of expression of β-catenin or GAB1. In such embodiments, a protein expression profile characterized by positive YAP1 expression and positive GAB1 expression and/or negative nuclear β-catenin expression is predictive of a SHH pathway medulloblastoma. In like manner, a protein expression profile characterized by positive YAP1 expression and negative GAB1 expression and/or positive nuclear β-catenin expression is predictive of a WNT pathway medulloblastoma.

In yet other embodiments, where the protein expression profile of a medulloblastoma sample is determined by detecting expression of filamin A and at least one of β-catenin, GAB1, or YAP1, a protein expression profile characterized by negative expression of filamin A is predictive of a non-WNT/non-SHH tumor. If, however, the protein expression profile is characterized by positive filamin A expression, typing of the analyzed medulloblastoma as a SHH pathway or WNT pathway tumor is readily achieved by the detection of expression of GAB-1 or β-catenin (nuclear). In such embodiments, a protein expression profile characterized by positive filamin A expression and positive GAB1 expression and/or negative nuclear β-catenin expression is predictive of a SHH pathway medulloblastoma. In like manner, a protein expression profile characterized by positive filamin A expression and negative GAB1 expression and/or positive nuclear β-catenin expression is predictive of a WNT pathway medulloblastoma.

Thus, in some embodiments, the medulloblastoma typing methods of the present invention comprise determining a protein expression profile among tumor cells for a sample obtained from a medulloblastoma of interest by detecting expression of two of these four biomarker proteins, wherein one of the biomarker proteins is β-catenin, and the second biomarker protein is either YAP1, GAB1, or filamin A. In other embodiments, the medulloblastoma typing methods of the invention comprise determining a protein expression profile for a sample obtained from a medulloblastoma of interest by detecting expression of two of these four biomarker proteins, wherein one of the biomarker proteins is GAB1, and the second biomarker protein is either β-catenin, YAP1, or filamin A. In yet other embodiments, the medulloblastoma typing methods of the present invention comprise determining a protein expression profile for a sample obtained from a medulloblastoma of interest by detecting expression of two of these four biomarker proteins, wherein one of the biomarker proteins is YAP1, and the second biomarker protein is either β-catenin or GAB1. In still other embodiments, the medulloblastoma typing methods of the present invention comprise determining a protein expression profile for a sample obtained from a medulloblastoma of interest by detecting expression of two of these four biomarker proteins, wherein one of the biomarker proteins is filamin A, and the second biomarker protein is either β-catenin or GAB1. In some preferred embodiments, the medulloblastoma typing methods of the present invention comprise determining a protein expression profile for a sample obtained from a medulloblastoma of interest by detecting expression of β-catenin and YAP1.

In some embodiments, the medulloblastoma typing methods of the present invention comprise determining a protein expression profile for a sample obtained from a medulloblastoma of interest by detecting expression of three of these four biomarker proteins, wherein one of the biomarker proteins is β-catenin, and the other two biomarker proteins are selected from YAP1, GAB1, and filamin A. In other embodiments, the medulloblastoma typing methods of the present invention comprise determining a protein expression profile for a sample obtained from a medulloblastoma of interest by detecting expression of three of these four biomarker proteins, wherein one of the biomarker proteins is GAB1, and the other two biomarker proteins are selected from β-catenin YAP1, and filamin A. In yet other embodiments, the medulloblastoma typing methods of the present invention comprise determining a protein expression profile for a sample obtained from a medulloblastoma of interest by detecting expression of three of these four biomarker proteins, wherein one of the biomarker proteins is YAP1, and the other two biomarker proteins are selected from β-catenin, GAB1, and filamin A. In still other embodiments, the medulloblastoma typing methods of the present invention comprise determining a protein expression profile for a sample obtained from a medulloblastoma of interest by detecting expression of three of these four biomarker proteins, wherein one of the biomarker proteins is filamin A, and the other two biomarker proteins are selected from β-catenin, GAB1, and YAP1. In some preferred embodiments, the medulloblastoma typing methods of the present invention comprise determining a protein expression profile for a sample obtained from a medulloblastoma of interest by detecting expression of β-catenin, GAB1, and YAP1.

In yet other embodiments, the medulloblastoma typing methods of the present invention comprise determining a protein expression profile among tumor cells for a sample obtained from a medulloblastoma of interest by detecting expression of β-catenin, GAB1, YAP1, and filamin A.

The present invention is in part based upon the discovery that GAB1 and filamin A are differentially expressed in these three molecular subgroups of medulloblastomas. In this manner, GAB1 shows positive expression in the cytoplasm of cells of medulloblastomas of the SHH pathway tumor subgroup, yet is not expressed within cells of medulloblastomas of the WNT pathway subgroup or the non-WNT/non-SHH tumor subgroup. Filamin A shows positive expression in the cytoplasm of cells of medulloblastomas of the WNT pathway and SHH pathway tumor subgroups, yet is not expressed within cells of medulloblastomas of the non-WNT/non-SHH tumor subgroup. Accordingly, the present invention also provides methods of typing medulloblastomas based on positive or negative expression of either of these biomarker proteins.

In this manner, in some embodiments, the present invention provides an immunohistochemical method for typing a medulloblastoma as a SHH pathway tumor or a non-SHH tumor. By "non-SHH tumor" is intended the tumor is not a SHH pathway tumor, and thus falls within one of the other two molecular subgroups described herein, i.e., is either a WNT pathway tumor or a non-WNT/non-SHH tumor. This method comprises determining a protein expression profile for a sample obtained from the medulloblastoma by detecting expression of GAB1 and typing the medulloblastoma as a SHH pathway tumor or a non-SHH tumor based on this protein expression profile. In this manner, where the protein expression profile is characterized by positive expression of GAB1, the medulloblastoma is typed as a SHH pathway tumor. In contrast, where the protein expression profile is characterized by negative expression of GAB1, the medulloblastoma is typed as a non-SHH tumor. In the latter case, detection of expression of an additional biomarker protein disclosed herein (for example β-catenin, YAP1, or filamin A) facilitates typing of the medulloblastoma tumor as either a WNT pathway tumor or a non-WNT/non-SHH tumor.

In other embodiments, the present invention provides an immunohistochemical method for typing a medulloblastoma as a non-WNT/non-SHH tumor. This method comprises determining a protein expression profile for a sample obtained from the medulloblastoma by detecting expression of filamin A and typing the medulloblastoma as a non-WNT/non-SHH tumor pathway tumor or a non-SHH pathway tumor based on this protein expression profile. In this manner, where the protein expression profile is characterized by negative expression of filamin A, the medulloblastoma is typed as a non-WNT/non-SHH tumor. In contrast, where the protein expression profile is characterized by positive expression of filamin A, the medulloblastoma is typed as falling outside the non-WNT/non-SHH tumor subgroup. In the latter case, detection of expression of an additional biomarker protein disclosed herein (for example β-catenin or GAB1) facilitates typing of the medulloblastoma tumor as either a WNT pathway tumor or a SHH pathway tumor.

In both of these embodiments, detection of expression of GAB1 or filamin A can be achieved using any protein detection method known to those of skill in the art. In some embodiments, expression is detected using an antibody that specifically binds GAB1 or an antibody that specifically binds filamin A, in the manner described herein below.

Expression of these biomarker proteins can be detected by any protein detection method known to those of skill in the art. In some embodiments, the medulloblastoma typing methods of the invention rely on the use of a unique combination of at least two, three, or four antibodies, each of which specifically binds to a distinct biomarker protein selected from the group consisting of β-catenin, YAP1, GAB1, and filamin A, to determine a protein expression profile within a medulloblastoma tissue sample. By "distinct" biomarker protein is intended the antibody binds specifically to that biomarker protein, and not to any of the other biomarker proteins to be detected. Thus, for example, β-catenin is a distinct biomarker protein for an antibody that specifically binds β-catenin. In like manner, YAP1 is a distinct biomarker protein for an antibody that specifically binds YAP1. Similarly, GAB1 is a distinct biomarker protein for an antibody that specifically binds GAB1. Likewise, filamin A is a distinct biomarker protein for an antibody that specifically binds filamin A. The distinct biomarker protein to which an antibody selectively binds is referred to herein as the respective "binding partner" for that antibody. Thus, for example, β-catenin is the binding partner for an antibody that specifically binds β-catenin. In like manner, YAP1 is the binding partner for an antibody that specifically binds YAP1. Similarly, GAB1 is the binding partner for an antibody that specifically binds GAB1. Likewise, filamin A is the binding partner for an antibody that specifically binds filamin A. Antibodies that specifically bind to these respective biomarker proteins are well known to those of skill in the art and include commercially available antibodies, as well as antibodies that can be prepared using standard procedures well known to those of skill in the art, and further described elsewhere herein.

In some embodiments, the medulloblastoma typing methods of the invention comprise contacting a tissue sample obtained from a medulloblastoma with a combination of at least two antibodies, each of which specifically binds to one of these four distinct biomarker proteins, determining a protein expression profile for the tissue sample based on detection of binding of at least two of these antibodies to their respective biomarker proteins, and typing the medulloblastoma as a WNT pathway tumor, a SHH pathway tumor, or a non-WNT/non-SHH tumor based on this protein expression profile. Detection of binding of a particular antibody to its distinct biomarker protein (i.e., its binding partner) is indicative of positive expression of that biomarker protein. In like manner, the lack of detection of binding of a particular antibody to its distinct biomarker protein is indicative of negative expression of that biomarker protein. Any antibody binding detection methods known to those of skill in the art can be utilized, including those described elsewhere herein.

In certain embodiments, the medulloblastoma typing methods of the invention comprise contacting a tissue sample obtained from a medulloblastoma with two antibodies selected from the group consisting of an antibody that specifically binds β-catenin, an antibody that specifically binds YAP1, an antibody that specifically binds GAB1, and an antibody that specifically binds filamin A; determining a protein expression profile for this tissue sample based on detection of binding of these two antibodies to their respective binding partners; and typing the medulloblastoma as a WNT pathway tumor, a SHH pathway tumor, or a non-WNT/non-SHH tumor based on the resulting protein expression profile, as outlined herein above and in Table 1. In specific embodiments, the tissue sample is contacted with an antibody that specifically binds β-catenin (i.e., a β-catenin antibody), and an antibody that specifically binds either GAB1 (i.e., a GAB1 antibody), YAP1 (i.e., a YAP1 antibody), or filamin A (i.e., a filamin A antibody). In some preferred embodiments, the tissue sample is contacted with an antibody that specifically binds β-catenin and an antibody that specifically binds YAP1.

In such embodiments, positive detection of binding of the β-catenin antibody to its binding partner within the nuclei of cells of the tissue sample indicates positive nuclear expression of β-catenin, and thus yields a protein expression profile that is predictive of a WNT pathway medulloblastoma. Alternatively, where nuclear expression of β-catenin is found to be negative (i.e., binding of the β-catenin antibody to its binding partner is not detected), positive detection of binding of the GAB1, YAP1, or filamin A antibody to its respective binding partner (i.e., GAB1, YAP1, or filamin A) within tumor cells of the tissue sample indicates positive expression of GAB1, YAP1, or filamin A, thus yielding a protein expression profile that is predictive of a SHH pathway medulloblastoma. In contrast, negative detection of binding of the β-catenin antibody to its binding partner in nuclei of the tumor cells of the tissue sample in combination with negative detection of binding of the GAB1, YAP1, or filamin A antibody to its respective binding partner indicates negative nuclear expression of β-catenin and negative expression of the other biomarker protein (i.e., YAP1, GAB1, or filamin A), thus yielding a protein expression profile that is predictive of a non-WNT/non-SHH medulloblastoma.

In other specific embodiments, the tissue sample obtained from the medulloblastoma is contacted with an antibody that specifically binds GAB1 (i.e., a GAB1 antibody), and an antibody that specifically binds either β-catenin (i.e., a β-catenin antibody), YAP1 (i.e., a YAP1 antibody), or filamin A (i.e., a filamin A antibody). In such embodiments, positive detection of binding of the GAB1 antibody to its binding partner in tumor cells of the tissue sample indicates positive expression of GAB1, thus yielding a protein expression profile that is predictive of a SHH pathway medulloblastoma. Alternatively, where expression of GAB1 is found to be negative (i.e., binding of the GAB1 antibody to GAB1 is not detected), positive detection of binding of the β-catenin antibody to its binding partner within the nuclei of tumor cells of the tissue sample indicates positive nuclear expression of β-catenin, and thus yields a protein expression profile that is predictive of a WNT pathway medulloblastoma. In yet other embodiments, negative detection of binding of the GAB1 antibody to its binding partner in tumor cells of the tissue sample and negative detection of binding of the β-catenin antibody to its binding partner within the nuclei of the cells of the tissue sample, or negative detection of binding of the filamin A antibody to its binding partner in cells of the tissue sample, is indicative of negative expression of GAB1 in combination with negative nuclear expression of β-catenin expression or negative expression of filamin A, thus yielding a protein expression profile that is predictive of a non-WNT/non-SHH medulloblastoma.

In yet other specific embodiments, the tissue sample of the medulloblastoma is contacted with an antibody that specifically binds YAP1 (i.e., a YAP1 antibody), and an antibody that specifically binds either β-catenin (i.e., a β-catenin antibody) or an antibody that specifically binds GAB1 (i.e., a GAB1 antibody). In such embodiments, negative detection of binding of the YAP1 antibody to its binding partner in cells of the tissue sample is indicative of negative expression of YAP1, thus yielding a protein expression profile that is predictive of a non-WNT/non-SHH medulloblastoma. Alternatively, where YAP1 expression is found to be positive (i.e., binding of the YAP1 antibody to YAP1 is detected in cells of the tissue sample), positive detection of binding of the GAB1 antibody to its binding partner is indicative of positive GAB1 expression, thus yielding a protein expression profile that is predictive of a SHH pathway medulloblastoma. In yet other embodiments, where YAP1 expression is found to be positive, negative detection of binding of β-catenin antibody to its binding partner within the nuclei of cells of the sample tissue is indicative of negative nuclear β-catenin expression, thus yielding a protein expression profile that is also predictive of a SHH pathway medulloblastoma. In still other embodiments, where YAP1 expression is found to be positive, positive detection of binding of β-catenin antibody to its binding partner within the nuclei of cells of the sample tissue is indicative of positive nuclear β-catenin expression, thus yielding a protein expression profile that is predictive of a WNT pathway medulloblastoma.

In still other specific embodiments, the tissue sample is contacted with an antibody that specifically binds filamin A (i.e., a filamin A antibody), and an antibody that specifically binds β-catenin (i.e., a β-catenin antibody) or an antibody that specifically binds GAB1 (i.e., a GAB1 antibody). In such embodiments, negative detection of binding of the filamin A antibody to its binding partner in cells of the tissue sample is indicative of negative filamin A expression, thus yielding a protein expression profile that is predictive of a non-WNT/non-SHH medulloblastoma. Alternatively, where filamin A expression is found to be positive (i.e., binding of the filamin A antibody to filamin A is detected), positive detection of binding of the GAB1 antibody to its binding partner in cells of the tissue sample is indicative of positive expression of GAB1, thus yielding a protein expression profile that is predictive of a SHH pathway medulloblastoma. In yet other embodiments, where filamin A expression is found to be positive, negative detection of binding of the β-catenin antibody to its binding partner in nuclei of cells of the tissue sample is indicative of negative nuclear expression of β-catenin, thus yielding a protein expression profile that is also predictive of a SHH pathway medulloblastoma. In still other embodiments, where filamin A expression is found to be positive, positive detection of binding of the β-catenin antibody to its binding partner in nuclei of cells of the tissue sample is indicative of positive nuclear expression of β-catenin, thus yielding a protein expression profile that is predictive of a WNT pathway medulloblastoma.

In other embodiments, the tissue sample is contacted with three antibodies selected from the group consisting of an antibody that specifically binds β-catenin, an antibody that specifically binds YAP1, an antibody that specifically binds GAB1, and an antibody that specifically binds filamin A; a protein expression profile for this tissue sample is determined based on detection of binding of these three antibodies to their respective binding partners; and the medulloblastoma is typed as a WNT pathway tumor, a SHH pathway tumor, or a non-WNT/non-SHH tumor based on the resulting protein expression profile, as outlined herein above and in Table 1. In specific embodiments, the tissue sample is contacted with an antibody that specifically binds 0-catenin, and two antibodies selected from the group consisting of an antibody that specifically binds YAP1, an antibody that specifically binds GAB1, and an antibody that specifically binds filamin A. In other specific embodiments, the tissue sample is contacted with an antibody that specifically binds GAB1, and two antibodies selected from the group consisting of an antibody that specifically binds β-catenin, an antibody that specifically binds YAP1, and an antibody that specifically binds filamin A. In yet other specific embodiments, the tissue sample is contacted with an antibody that specifically binds YAP1, and two antibodies selected from the group consisting of an antibody that specifically binds β-catenin, an antibody that specifically binds GAB1, and an antibody that specifically binds filamin A. In still other specific embodiments, the tissue sample is contacted with an antibody that specifically binds filamin A, and two antibodies selected from the group consisting of an antibody that specifically binds β-catenin, an antibody that specifically binds GAB1, and an antibody that specifically binds YAP1. In some preferred embodiments, the tissue sample is contacted with an antibody that specifically binds β-catenin, an antibody that specifically binds YAP1, and an antibody that specifically binds GAB1.

In yet other embodiments, the tissue sample is contacted with four antibodies selected from the group consisting of an antibody that specifically binds β-catenin, an antibody that specifically binds YAP1, an antibody that specifically binds GAB1, and an antibody that specifically binds filamin A; a protein expression profile for this tissue sample is determined based on detection of binding of these four antibodies to their respective binding partners; and the medulloblastoma is typed as a WNT pathway tumor, a SHH pathway tumor, or a non-WNT/non-SHH tumor based on the resulting protein expression profile, as outlined herein above and in Table 1.

Thus, the immunohistochemical typing methods of the invention require the detection of expression of GAB1, filamin A, or at least two biomarker proteins selected from the group consisting of β-catenin, GAB1, YAP1, and filamin A, in a sample obtained from a medulloblastoma. It is recognized that detection of more than one biomarker protein in a body sample may be used to more accurately type the medulloblastoma to one of these three molecular subgroups. Therefore, in some embodiments, two or more biomarker proteins are used, more preferably, two or more complementary biomarker proteins. By "complementary" is intended that detection of the combination of biomarker proteins in a medulloblastoma sample results in the accurate determination of molecular subgroup in a greater percentage of cases than would be identified if only one of the biomarker proteins was used. Thus, in some cases, a more accurate determination of the molecular subgroup of medulloblastoma can be made by using at least two biomarker proteins. Accordingly, where at least two biomarker proteins are used, at least two antibodies directed to distinct biomarker proteins will be used to practice the immunohistochemical methods disclosed herein. These antibodies may be contacted with the medulloblastoma sample simultaneously or successively.

When a combination of two or more biomarker proteins is used, the biomarkers will typically be substantially statistically independent of one another. By "statistically independent" biomarker proteins is intended that the molecular subgroups identified thereby are independent such that one biomarker protein does not provide substantially repetitive information with regard to the complementary biomarker protein. This may ensure, for instance, that a second biomarker protein is not used in conjunction with a first biomarker protein when the two are not substantially statistically independent. The dependence of the two biomarker proteins may indicate that they are duplicative and that the addition of a second biomarker adds no additional value to the predictive power of a given pair of biomarker proteins. In order to optimize the predictive power of a given panel of biomarker proteins it is also desirable to reduce the amount of signal "noise" by minimizing the use of biomarker proteins that provide duplicative predictive information when compared to another biomarker protein in the panel. Where independent predictive biomarker proteins are used to practice the present methods, the predictive value is increased by detecting the expression of two, three, or four of these biomarker proteins. In such cases, any combination of independent biomarkers can be used.

One of skill in the art will also recognize that a panel of biomarker proteins can be used to type a medulloblastoma as a WNT pathway tumor, a SHH pathway tumor, or a non-WNT/non-SHH tumor in accordance with the methods of the invention. In some embodiments, a panel comprising at least two biomarker proteins selected from the group consisting of β-catenin, filamin A, GAB1, and YAP1, is utilized. One particular panel of biomarker proteins may comprise, for example, all or a subset of said proteins. In certain aspects of the invention, a panel comprises at least two statistically independent biomarker proteins. In particular embodiments, the immunohistochemical methods for typing medulloblastoma comprise collecting a tissue sample from a medulloblastoma, contacting the sample with at least two antibodies, each specific for a different biomarker protein selected from the group consisting of β-catenin, filamin A, GAB1, and YAP1, detecting antibody binding, and determining if the biomarker proteins are expressed. That is, samples are incubated with the antibodies for a time sufficient to permit the formation of antibody-biomarker protein complexes, and antibody binding is detected, for example, by a labeled secondary antibody.

Biomarker Proteins

It is recognized that the β-catenin, YAP1, GAB1, and filamin A biomarker proteins to be detected within the medulloblastoma sample may be the full-length polypeptides, or may be detectable fragments or naturally occurring variants thereof. By "fragment" is intended a portion of the amino acid sequence and hence protein encoded thereby. A fragment of a biomarker polypeptide will generally consist of at least 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs known in the art. The protein and corresponding coding sequence for each of these markers is known in the art, and are further identified in the Sequence Listing provided concurrently herewith.

As used herein, "sequence identity" or "identity" in the context of two polypeptide sequences makes reference to the residues in the two sequences that are the same when aligned for maximum correspondence over a specified comparison window. When percentage of sequence identity is used in reference to proteins it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical amino acid residue matches and an identical percent sequence identity when compared to the corresponding alignment generated by GAP Version 10.

Tumor Samples

The methods and kits of the present invention find use in typing medulloblastomas from any subject in need thereof. The subject may be a patient undergoing treatment for a recurring incidence of medulloblastoma, or a patient initially diagnosed with a medulloblastoma, and may be a patient for whom eligibility for enrollment into a clinical trial is to be determined. Tumor samples may be obtained from a subject by removing a tissue sample (i.e., biopsy). Methods for collecting biopsy samples from medulloblastomas are well known in the art. In some embodiments, a sample is obtained, for example, from resected tissue. Where a medulloblastoma tissue sample must be stored prior to assaying for the presence or absence of two or more of the β-catenin, GAB1, YAP1, and filamin A biomarker proteins, the sample may be frozen for later preparation or immediately placed in a fixative solution. Tissue samples of the invention may be processed into serial sections using a microtome instrument or a cryostat. Techniques for producing thin sections of a sample by means of a microtome or cryostat are well known in the art (U.S. Patent Application Publication No. 20100118133; Wang et al. (2008) *Biotech. Histochem.* 83(3):179-189, and Vollmer et al. (1989) *J. Steroid Biochem.* 33:41-47). Tumor tissue samples may be transferred to a glass slide for viewing under magnification. Fixative and staining solutions may be applied to the tissues for preserving the specimen and for facilitating examination. In preferred embodiments, the sample is a formalin-fixed, paraffin wax-embedded (FFPE) medulloblastoma tissue sample.

Immunohistochemical Detection of Biomarker Proteins

In accordance with the immunohistochemical methods of the invention, a protein expression profile is determined for a sample obtained from a medulloblastoma by detecting expression of GAB1, detecting expression of filamin A, or detecting expression of at least two biomarker proteins selected from the group consisting of β-catenin, YAP1, GAB1, and filamin A. The medulloblastoma is then typed as a WNT pathway tumor, a SHH pathway tumor, or a non-WNT/non-SHH tumor based on this protein expression profile, in the manner set forth above. As noted above, any means for detecting expression of a particular biomarker protein of interest is contemplated. In specific embodiments, expression of a biomarker protein in the medulloblastoma sample is detected by means of a binding protein capable of interacting specifically with that biomarker protein, or a naturally occurring variant or fragment thereof. Preferably, labeled antibodies, binding portions thereof, or other binding partners may be used. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

In particular embodiments, the immunohistochemical typing method comprises contacting a tissue sample obtained from the medulloblastoma with at least two antibodies selected from the group consisting of an antibody that specifically binds β-catenin, an antibody that specifically binds YAP1, an antibody that specifically binds GAB1, and an antibody that specifically binds filamin A; determining a protein expression profile for the tissue sample based on detection of binding of the at least two antibodies to their respective biomarker proteins; and typing the medulloblastoma as a WNT pathway tumor, a SHH pathway tumor, or a non-WNT/non-SHH tumor based on this protein expression profile. By "contacting" in the context of an antibody and a tissue sample is intended the medulloblastoma tissue sample is exposed to the antibody for a sufficient time to allow the formation of a complex between the antibody and its binding partner (i.e., its respective biomarker protein) if that binding partner is present within the cells of the tissue sample.

One of skill in the art will recognize that the immunohistochemical methods described herein below may be performed manually or in an automated fashion using, for example, the Autostainer Universal Staining System (DAKO). One protocol for antibody staining (i.e., immunohistochemistry) of medulloblastoma tissue samples is provided in Examples 2 and 4 below.

In one embodiment, the medulloblastoma tissue sample is collected following tissue resection, as is well known in the art. The sample may be freshly frozen for later preparation or immediately placed in a fixative solution. In this manner, the tissue sample may be fixed by treatment with a reagent such as formalin, paraformaldehyde, gluteraldehyde, methanol, or the like, and embedded in paraffin. Methods for preparing slides for immunohistochemical analysis from fresh-frozen and formalin-fixed paraffin-embedded tissue samples are well known in the art and can be used with the immunohistochemical typing methods of the present invention.

In some embodiments of the immunohistochemical methods of the invention, a medulloblastoma tissue sample may need to be modified in order to make one or more of the biomarker proteins (i.e., respective antigens), where present, accessible to antibody binding. For example, formalin fixation of tissue samples results in extensive cross-linking of proteins that can lead to the masking or destruction of antigen sites and, subsequently poor antibody staining. As used herein, "antigen retrieval" or "antigen unmasking" refers to methods for increasing antigen accessibility or recovering antigenicity in, for example, formalin-fixed, paraffin-embedded tissue samples. Any method for making antigens more accessible for antibody binding may be used in the practice of the invention, including those antigen retrieval methods known in the art. See, for example, Hanausek and Walaszek, eds. (1998) *Tumor Marker Protocols* (Humana Press, Inc., Totowa, N.J.); Meera et al. (1995) *Eur. J. Morphol.* 33(4): 337-358; and Shi et al., eds. (2000) *Antigen Retrieval Techniques: Immunohistochemistry and Molecular Morphology* (Eaton Publishing, Natick, Mass.), all of which are herein incorporated by reference in their entirety.

Antigen retrieval methods include but are not limited to treatment with proteolytic enzymes (e.g., trypsin, chymoptrypsin, pepsin, pronase, etc.) or antigen retrieval solutions. Antigen retrieval solutions of interest include, for example, citrate buffer or tris buffer. In some embodiments, antigen retrieval comprises applying the antigen retrieval solution to a formalin-fixed tissue sample and then heating the sample in an oven (e.g., 60° C.), steamer (e.g., 95° C.), or pressure cooker (e.g., 120° C.) at specified temperatures for defined time periods. In other aspects of the invention, antigen retrieval may be performed at room temperature. Incubation times will vary with the particular antigen retrieval solution selected and with the incubation temperature. For example, an antigen retrieval solution may be applied to a sample for as little as 5, 10, 20, or 30 minutes or up to overnight. The design of assays to determine the appropriate antigen retrieval solution and optimal incubation times and temperatures is standard and well within the routine capabilities of those of ordinary skill in the art.

Following antigen retrieval, the medulloblastoma tissue sample is blocked using an appropriate blocking agent, e.g., hydrogen peroxide. An antibody directed to a biomarker of interest is then incubated with the sample for a time sufficient to permit antigen-antibody binding.

As noted above, the immunohistochemical typing methods of the present invention detect expression of at least two biomarker proteins selected from the group consisting of β-catenin, GAB1, YAP1, and filamin A. Therefore, in particular embodiments, at least two antibodies, each of which is directed to a distinct biomarker protein, are used to type the medulloblastoma as a WNT pathway tumor, a SHH pathway tumor, or a non-WNT/non-SHH tumor. Each individual antibody may be contacted with a separate tissue section obtained from a single medulloblastoma sample, and the resulting data pooled. Alternatively, these antibodies may be contacted with a single tissue sample section sequentially as individual antibody reagents or simultaneously as an antibody cocktail.

Techniques for detecting antibody binding to a biomarker protein of interest are well known in the art. In this manner, antibody binding to a biomarker protein of interest may be detected through the use of chemical reagents that generate a detectable signal that corresponds to the level of antibody binding and, accordingly, to the level of biomarker protein expression. For example, antibody binding can be detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker protein of interest. Enzymes of particular interest include horseradish peroxidase (HRP) and alkaline phosphatase (AP). Commercial antibody detection systems, such as, for example the DAKO Envision™+ system and Biocare Medical's MACH 3™ system, may be used to practice the present invention.

Detection of antibody binding to a biomarker protein of interest can be facilitated by coupling the antibody to a detectable substance or "label." Examples of detectable substances or labels include various enzymes, prosthetic groups, fluorescent materials, luminescent materials, bioluminescent materials, and radioactive materials. Examples of suitable enzymes include horseradish peroxidase (HRP), alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, Texas Red, AlexaFluor conjugates, and aequorin; and examples of suitable radioactive material include $^{125}$I, $^{131}$I, $^{35}$S, or $^{3}$H. In some embodiments, antibody binding to a biomarker protein of interest is detected through the use of an HRP-labeled polymer that is conjugated to a secondary antibody.

In particular embodiments where the antibodies are contacted with the medulloblastoma tissue in a cocktail, the antibodies are chosen so they do not cross react with each other. For example, each antibody used may be produced in a different host, such that there are no cross reactivity interactions among the secondary antibodies being used.

Following the contacting of the tissue sample with the antibodies of interest, the mounted tissue sections are stained for antibody binding using, for example, the chromogen 3,3-diaminobenzidine (DAB), and then counterstained with hematoxylin and, optionally, a bluing agent such as ammonium hydroxide. In some aspects of the invention, slides are reviewed microscopically by a pathologist to assess cell staining (i.e., biomarker expression) and to determine the protein expression profile for GAB1, filamin A, or at least two biomarkers selected from the group consisting of β-catenin, GAB1, YAP1, and filamin A. Alternatively, the stained tissue sections may be reviewed via automated microscopy or by personnel with the assistance of computer software that facilitates the identification of positive staining cells.

The antibodies used to practice the invention are selected to have specificity for the biomarker proteins of interest. Methods for making antibodies and for selecting appropriate antibodies are known in the art. See, for example, Celis, ed. (2006) *Cell Biology & Laboratory Handbook*, 3rd edition (Elsevier Academic Press, Burlington, Mass.), which is herein incorporated in its entirety by reference. In some embodiments, commercial antibodies directed to specific biomarker proteins may be used to practice the invention. The antibodies of the invention may be selected on the basis of desirable staining of histological samples. That is, in preferred embodiments the antibodies are selected with the end sample type (e.g., formalin-fixed, paraffin-embedded medulloblastoma tissue samples) in mind and for binding specificity.

One of skill in the art will recognize that optimization of staining reagents and conditions, for example, antibody titer and detection chemistry parameters, is needed to maximize the signal to noise ratio for a particular antibody. Antibody concentrations that maximize specific binding to the biomarkers of the invention and minimize non-specific binding (or "background") will be determined. In particular embodiments, appropriate antibody titers are determined by initially testing various antibody dilutions on formalin-fixed, paraffin-embedded normal and medulloblastoma tissue samples. The design of assays to optimize antibody titer and detection conditions is standard and well within the routine capabilities of those of ordinary skill in the art. Some antibodies require additional optimization to reduce background staining and/or to increase specificity and sensitivity of staining.

Furthermore, one of skill in the art will recognize that the concentration of a particular antibody used to practice the methods of the invention will vary depending on such factors as time for binding, level of specificity of the antibody for the biomarker protein, and method of body sample preparation. Moreover, when multiple antibodies are used in a single sample, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio. Techniques for optimizing staining reagents and conditions for immunohistochemistry are well known in the art.

In order to score biomarker protein expression, the medulloblastoma tissue sample to be examined may be compared with tissue samples from corresponding regions (i.e., cerebellum) obtained from a healthy person, a non-medulloblastoma tissue sample, or another type of brain tumor sample, including those of neuroectodermal origin. That is, the "normal" level of expression is the level of expression of the biomarker protein in, for example, a cerebellar sample from a human subject or patient not afflicted with medulloblastoma. Such a sample can be present in standardized form. In some embodiments, determination of biomarker protein expression requires no comparison between the tumor sample and a corresponding tissue sample that originates from a healthy person. In this manner, detection of expression of at least two biomarker proteins, or at least three biomarker proteins selected from the group consisting of β-catenin, GAB1, YAP1, and filamin A, or detection of expression of all four of these biomarker proteins yields a protein expression profile that is indicative of a molecular group of medulloblastoma, i.e., a WNT pathway tumor, a SHH pathway tumor, or a non-WNT/non-SHH tumor, and may preclude the need for comparison to a corresponding tissue sample that originates from a healthy person. Control samples may also be positive controls or negative controls. By "positive controls" is intended samples and tissues known to show a positive expression profile for one or more of the biomarker proteins of the invention, such as tissue and microarray samples from other tissues and cancerous tissues including but not limited to medulloblastoma, colon, placenta, tonsil, and appendix, or an internal positive control such as intrinsic vascular elements.

Also encompassed in the immunohistochemical methods of the invention is a method for validating or verifying the accurate performance of the typing method, wherein the method comprises processing the biological sample, detecting the expression of the biomarkers of interest, and comparing the expression of the biomarker or biomarkers of interest in the sample to control samples. In some embodiments of the invention, the biological and control tissue samples are affixed to the same microscope slide, where both the tissue sample and respective control sample are subjected to the same condition of reagents, same time, and temperature. In other embodiments, the control sample is fixed, for example by formalin, paraformaldehyde, gluteraldehyde, methanol, or the like and embedded in paraffin, affixed onto the microscope slide with its corresponding biological sample, and subjected to the same conditions as the biological sample.

One of skill in the art will appreciate that any or all steps in the immunohistochemical typing methods of the invention could be implemented by personnel or, alternatively, performed in an automated fashion. Thus, the steps of medulloblastoma sample preparation, sample staining, and detection of biomarker expression may be automated. Moreover, in some embodiments, the immunohistochemical methods of the invention are used in conjunction with computerized imaging equipment and software to facilitate the identification of positive-staining cells by a pathologist.

Production of Antibodies for Use in the Medulloblastoma Typing Methods of the Invention The immunohistochemical methods of the invention contemplate the use of antibodies that specifically bind to β-catenin, GAB1, YAP1, or filamin A in order to detect expression of one or more of these biomarker proteins. By "specifically binds" is intended the antibody binds to an epitope of the particular biomarker protein of interest, and does not bind to another biomarker protein of interest. By "epitope" is intended the part of an antigenic molecule to which an antibody is produced and to which the antibody will bind.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Thus, the term "antibody" is used in the broadest sense and covers fully assembled antibodies, antibody fragments that can bind antigen (e.g., Fab', F'(ab)$_2$, Fv, single chain antibodies, diabodies), and recombinant peptides comprising the foregoing. As previously noted, any antibody intended for use in the methods and kits of the present invention may be labeled with a detectable substance to facilitate biomarker protein detection in the medulloblastoma sample.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize 35 readily. Pepsin treatment yields an F(ab')2 fragment that has two antigen-combining sites and is still capable of cross-linking antigen.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

As an alternative to the use of hybridomas, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody. A monoclonal antibody can also be identified and isolated by screening a recombinant combinatorial immunoglobulin library (e.g., an antibody phage display library) with a biomarker protein to thereby isolate immunoglobulin library members that bind the biomarker protein. Kits for generating and screening phage display libraries are commercially available (e.g., the Pharmacia *Recombinant Phage Antibody System*, Catalog No. 27-9400-01; and the Stratagene *SurfZAPθ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Polyclonal antibodies can be prepared by immunizing a suitable subject (e.g., rabbit, goat, mouse, or other mammal) with a biomarker protein immunogen. The antibody titer in the immunized subject can be monitored over time by standard techniques, such as with an enzyme linked immunosorbent assay (ELISA) using immobilized biomarker protein. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77-96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.* 54:387-402).

In another embodiment, antibodies for use in the methods of the invention can be obtained commercially from any source. Exemplary antibodies include, but are not limited to, β-catenin antibody (#610154 and others, available from BD Biosciences, USA, as well as catalog #760-4242, available from Ventana, USA); GAB1 antibody (#ab27439 and others, available from Abcam, USA); filamin A antibody (#10R-F113A and others, available from Fitzgerald, USA), and YAP1 antibody (#sc-101199 and others, available from Santa Cruz Biotechnology, USA).

Further Subtyping of Medulloblastoma Samples

The results of the immunohistochemical methods described above can be combined with assessment of clinical information, conventional diagnostic methods, and expression of other molecular markers (for example, but not limited to, Ki67, p27 etc.) known in the art to be involved in the etiology of medulloblastoma, should such combined information be deemed beneficial for determination of a treatment plan for the subject whose medulloblastoma has been analyzed and typed as a WNT pathway tumor, a SHH pathway tumor, or a non-WNT/non-SHH tumor in accordance with the immunohistochemical typing methods of the present invention.

Thus, the immunohistochemical methods of the present invention can be further combined with the standard histological preparations (hematoxylin & eosin) to assess general architectural and cytological features, including nodule formation, differentiation along neuronal (neurocytic/ganglionic) and astrocytic lines, and large cell or anaplastic phenotypes. In other embodiments of the invention, reticulin preparations are used to evaluate desmoplasia. Thus, for example, detection of internodular desmoplasia is required for histologic typing of D/N medulloblastoma, including the paucinodular D/N variant and MBEN.

In like manner, any biomarker whose expression is indicative of a particular molecular subgroup of medulloblastoma can be used in conjunction with the methods of the present invention. Such biomarkers include genes and proteins that are, for example, involved in cell proliferation, cell cycle control, or the generalized mechanisms of cancer motility and invasion. Biomarkers of potential interest can include, but are not limited to, for example, Ki67 and p27 (see for example de Haas et al. (2008) *Clin. Cancer Res.* 14(13):4154-4160; and Thompson et al. (2006) *J. Clin. Oncol.* 24(12):1924-1931; Kool et al. (2008) *PLoS.* 3(8):e3088; all of which are herein incorporated by reference in their entirety).

Expression of these additional biomarker proteins can be detected using any of the standard detection methods known in the art, and include detection at the protein or nucleic acid level. Such methods are well known in the art and include but are not limited to western blots, northern blots, ELISA, immunoprecipitation, immunofluorescence, flow cytometry, immunohistochemistry, nucleic acid hybridization techniques, for example, in situ hybridization (ISH), nucleic acid reverse transcription methods, nucleic acid amplification, and gene sequencing methods. Thus, for example, where detection is at the level of the protein, detection can utilize antibodies that are directed against these additional biomarker proteins. These antibodies can be used in various methods such as Western blot, ELISA, multiplexing technologies, immunoprecipitation, or immunohistochemistry techniques.

In some embodiments, it may be desirable to further determine the genetic abnormalities that contribute to the particular molecular subgroup into which the medulloblastoma has been typed. For example, DNA ISH can be used to determine the status of specific loci on chromosomes. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using autoradiography, fluorescence microscopy or immunohistochemistry, respectively. ISH can also use two or more probes, labeled with radioactivity or the other non-radioactive labels, to simultaneously detect two or more transcripts. For example, the genetic abnormalities may be detected using fluorescence in situ hybridization (FISH).

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, which in specific embodiments of the invention comprise a polynucleotide comprising regions of loci known to harbor chromosomal copy number abnormalities (CNAs) in medulloblastomas. Particular embodiments include, but are not restricted to, chromosome 6 (including SGK1), chromosome 17 (including HIC1), chromosome 9, PTCH1, MYC, and MYCN. Deoxyribonucleic acid probes can include those generated by PCR using specific primers to the regions listed above, olignucleotide probes synthesized in vitro, or DNA obtained from bacterial artificial chromosome or fosmid libraries. Probes include not only deoxyribonucleic or ribonucleic acids but also polyamides and other probe materials that can specifically detect the presence of the target DNA sequence. For nucleic acid probes, examples of detection reagents include, but are not limited to radiolabeled probes, enzymatic labeled probes (horse radish peroxidase, alkaline phosphatase), affinity labeled probes (biotin, avidin, or steptavidin), and fluorescent labeled probes (6-FAM, VIC, TAMRA, MGB). One skilled in the art will readily recognize that the nucleic acid probes described in the present invention can readily be incorporated into one of the established kit formats described herein below.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence and specifically detect and/or identify a polynucleotide comprising the region of interest with the genetic abnormality. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide. Probes can be used as primers, but are generally designed to bind to the target DNA or RNA and are not used in an amplification process.

Methods for preparing and using probes and primers are described, for example, in *Molecular Cloning: A Laboratory Manual,* 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 10 (Informax Inc., Bethesda Md.); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

In specific embodiments, probes for detecting a genetic abnormality in medulloblastomas are labeled with appropriate fluorescent or other markers and then used in hybridizations. Example 6 provided herein sets forth one protocol that can be used with the present invention, which effectively detects the genetic abnormalities, but one of skill in the art will recognize that many variations of these assay can be used equally well. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo et al. (1991) *Am. J. Hum. Genet.* 42:112-119; Klinger et al. (1992) *Am. J. Hum. Genet.* 51:55-65; and Ward et al. (1993) *Am. J. Hum. Genet.* 52:854-865). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

Thus, the methods disclosed herein can also be combined with other prognostic methods or analyses, including, but not limited to, tumor size, expression levels of Ki67, p53, $p27^{Kip1}$, synaptophysin, MYC, MYON, GFAP, CCNB1, LDHB, TrkC, AXIN1 family members, Akt, Pin1, Notch2, and/or NeuN, and molecular cytogenetic data identifying CNAs, for example, in chromosome 6 (including SGK1), chromosome 9 (including PTCH1 deletions) and chromosome 17 (including HIC1), and the like.

Assessing the Outcome of Medulloblastoma Patients

The accurate assessment of disease risk remains a major goal in children with medulloblastoma. Although no specific biochemical test exists for assessing the presence of medulloblastoma, histologically identical medulloblastomas are composed of distinct subgroups with different prognoses. For example, the expression of Erb2 is indicative of a poor outcome, while expression of TrkC or neurotrophin-3 receptor is indicative of a good outcome. Additionally, gene mutations impairing the WNT signaling transduction pathway have been found in approximately 15% of human sporadic medulloblastomas, and 25% of cases associated with a favorable disease outcome (Clifford et al. (2006) *Cell Cycle* 5(22): 2666-2670). Combined factors, among others, that contribute to a favorable outcome in medulloblastoma patients include age <3 years, complete resection of the tissue, WNT/Wg pathway activation, nuclear β-catenin expression, and monosomy of chromosome 6. Combined factors, among others, that contribute to poor or bad outcomes in medulloblastoma patients include age <3 years, residual disease >1.5 $cm^2$ after resection, metastasis, chromosome 17p loss, as well as expression of Erb B2 receptor, C-myc, and OTX (Mueller and Chang (2009) *Neurotherapeutics* 6(3):570-586).

The immunohistochemical typing methods of the present invention offer insight into the prognosis and potential stratification of medulloblastoma patients by rapidly categorizing their medulloblastomas as being WNT pathway tumors, SHH pathway tumors, or non-WNT/non-SHH tumors. In this manner, medulloblastomas typed as WNT pathway tumors are indicative of a good outcome following standard therapy or treatment with a WNT signaling pathway inhibitor, particularly when combined with other factors that contribute to a favorable outcome. As used herein, "indicative of a good outcome" refers to an increased likelihood that the patient will remain cancer free following treatment. In some embodiments, "indicative of a good outcome" refers to an increased likelihood that the patient will remain cancer free for at least five, more particularly at least ten years. In one embodiment, Patients having a medulloblastoma typed as a WNT pathway tumor in accordance with the immunohistochemical typing methods of the present invention advantageously can be treated using less aggressive therapeutic regimens.

Alternatively, medulloblastomas typed as SHH pathway tumors or non-WNT/non-SHH tumors have a worse outcome, relative to medulloblastomas of the WNT pathway tumor subgroup, particularly when combined with other clinical, pathologic, and molecular factors that contribute to an unfavorable outcome. By "indicative of a poor outcome" is intended an increased likelihood of relapse or recurrence of the underlying cancer or tumor, metastasis, or death following treatment. For example, "indicative of a poor outcome" may refer to an increased likelihood or relapse or recurrence of the underlying cancer or tumor, metastasis, or death within five years, more particularly ten years post-treatment. Patients having a medulloblastoma typed as a SHH pathway tumor in accordance with the immunohistochemical typing methods of the present invention advantageously can be treated with specific therapeutic regimens that inhibit the SHH signaling pathway (for example, SHH signaling pathway inhibitors). This is also true for WNT-pathway tumors and specific WNT-pathway antagonists. Patients having a medulloblastoma typed as a non-WNT/non-SHH tumor in accordance with the immunohistochemical typing methods of the present invention advantageously can be identified as needing standard treatment protocols (i.e., surgery, radiation, and chemotherapy) using more aggressive approaches based on clinical or pathological presentation (for example, histologic subtype or molecular cytogenetic data).

The immunohistochemical typing methods of the present invention thus provide new means for quickly identifying beneficial/optimal treatment regimens for medulloblastoma patients that allow more appropriate allocation to standard treatment regimens, the potential application of targeted therapies, and the possibility of reducing long-term adverse events. Accordingly, the invention can lead to an improvement in a patient's overall survival as well as their event-free survival. As used herein, the term "overall survival" refers to the chances of staying alive for a group of individuals suffering from medulloblastoma. It denotes the percentage of individuals in the group who are likely to be alive after a particular duration of time. At a basic level, the overall survival is representative of cure rates, rive year rates are reported for many cancers because those who survive five years are quite likely to be cured of their disease. In some slow growling and low grade malignancies where late relapses are common, the ten-year overall survival is more representative of cure rates. As used herein, the term "event-free survival" refers to the possibility of having a particular group of defined events, such as metastases, recurrence, or death, after a treatment that is designed to delay or prevent that group of events.

Determining Eligibility for Entry into Clinical Trials and Selecting Treatment Regimens In medulloblastoma patients, the standard front-line therapy includes adjuvant, platinum-based chemotherapy. However, cisplatin- and carboplatin-associated toxicity produces serious adverse effects. Therefore, there is a need in the art to find novel therapies for treating medulloblastoma patients. Many small molecule inhibitors of the SHH or WNT signaling pathway with the potential to treat a subset of medulloblastoma patients are being considered for, or are being tested in, clinical trials. These include, but are not limited to, the SHH signaling pathway inhibitors GDC-0449, LDE225, LEQ506, and those disclosed in U.S. Pat. No. 7,498,304 and International Patent Application Publication No. WO 2009/132023 A2, which describe SHH signaling pathway inhibitors. See also, for example, U.S. Patent Application Publication Nos. 20100203113 and 20100137394, describing WNT signaling pathway inhibitors. The methods of the present invention provide a means to identify patients with medulloblastomas within molecular subgroups that can benefit from experimental treatments with such signaling pathway inhibitors. In a further embodiment, the present invention identifies a patient that can benefit from a clinical trial for treating medulloblastomas with a WNT pathway or SHH pathway inhibitor.

The methods of the invention can therefore be used to assist in selecting appropriate courses of treatment and to identify patients that would benefit from more or less aggressive therapy, or new avenues of therapy. In particular embodiments, the immunohistochemical techniques of the present invention are used to identify a medulloblastoma as being regulated by the WNT or SHH signaling pathway, and thus a tumor that could favorably respond to existing therapeutic agents, or experimental therapeutic agents, that are inhibitors of the WNT or SHH signaling pathway, respectively. In this manner, the immunohistochemical typing methods of the invention provide a means to identify subjects with a medulloblastoma of the WNT pathway tumor subgroup or the SHH pathway tumor subgroup that renders the subject eligible for enrollment into appropriate clinical trials. In other embodiments, the immunohistochemical typing methods of the invention provide a means to identify subjects with a medulloblastoma of the non-WNT/non-SHH tumor subgroup, who would not be responsive to existing therapeutic agents, or experimental therapeutic agents, that are inhibitors the WNT or SHH signaling pathway. Rather, in the latter case, these patients would be identified as needing treatment regimens suitable for treatment of this molecular subgroup of medulloblastomas.

The immunohistochemical typing methods disclosed herein also find use in identifying a patient with a medulloblastoma that would benefit from a selected treatment. By "identifying a patient with a medulloblastoma that would benefit from a selected treatment" is intended assessing the likelihood that a patient will experience a positive or negative outcome with a particular treatment and potentially reducing the long-term adverse events by optimization of current therapies. Thus, the immunohistochemical typing methods of the inventions provide a means to identify possible treatments that could result in a positive or a negative outcome. As used herein, "result in a positive treatment outcome" refers to an increased likelihood that the patient will experience beneficial results from the selected treatment (e.g., complete or partial remission, reduced tumor size, increased survival, etc.). By "result in a negative treatment outcome" is intended an increased likelihood that the patient will not benefit from the selected treatment with respect to the progression of the medulloblastoma.

In certain embodiments of the present invention, typing a medulloblastoma as a WNT pathway tumor identifies a patient with a medulloblastoma that will have a positive outcome to standard therapy (i.e., surgery, radiation or chemotherapy) and/or to therapy with a WNT signaling pathway inhibitor. In other embodiments, typing a medulloblastoma as a SHH pathway tumor identifies a patient with a medulloblastoma that will have a positive outcome to therapy with a SHH signaling pathway inhibitor. In yet other embodiments, typing a medulloblastoma as a non-WNT/non-SHH tumor identifies a patient with a medulloblastoma that will have a negative treatment outcome with a WNT or SHH signaling pathway inhibitor, and for which standard therapy with a more aggressive treatment regimen based on clinical or pathological presentation is warranted to achieve a positive treatment outcome.

Kits

Kits for practicing the methods of the invention are further provided. By "kit" is intended any manufacture (e.g., a package or a container) comprising at least one reagent, e.g. an antibody, for specifically detecting the expression of a biomarker of the invention. The kit may be promoted, distributed, or sold as a unit for performing the methods of the present invention. Additionally, the kits may contain a package insert describing the kit and methods for its use.

In particular embodiments, kits for practicing the immunohistochemical methods of the invention are provided. Such kits are compatible with both manual and automated immunohistochemistry techniques for subtyping medulloblastoma (e.g., cell staining) as described herein. In some embodiments, these kits comprise at least two antibodies selected from the group consisting of an antibody that specifically binds β-catenin, an antibody that specifically binds YAP1, an antibody that specifically binds GAB1, and an antibody that specifically binds filamin A. In some of these embodiments, the kits comprise an antibody that specifically binds β-catenin and an antibody that specifically binds GAB1, YAP1, or filamin A. In other embodiments, these kits comprise three antibodies selected from the group consisting of an antibody that specifically binds β-catenin, an antibody that specifically binds YAP1, antibody that specifically binds GAB1, and an antibody that specifically binds filamin A. In some of these embodiments, the kits comprise an antibody that specifically binds β-catenin, an antibody that specifically binds GAB1, and an antibody that specifically binds YAP1. In yet other embodiments, these kits comprise an antibody that specifically binds β-catenin, an antibody that specifically binds YAP1, an antibody that specifically binds GAB1, and an antibody that specifically binds filamin A.

Each antibody may be provided in the kit as an individual reagent or, alternatively, as an antibody cocktail comprising two or more of the antibodies directed to these different biomarker proteins of interest. Furthermore, any or all of the kit reagents may be provided within containers that protect them from the external environment, such as in sealed containers or contains that protect the reagents from light. Positive and/or negative controls may be included in the kits to validate the activity and correct usage of reagents employed in accordance with the invention. Controls may include samples, such as tissue sections, cells fixed on glass slides, etc., known to be either positive or negative for the presence of the biomarker protein of interest. The design and use of controls is standard and well within the routine capabilities of those of ordinary skill in the art. Chemicals for the detection of antibody binding to the biomarker, a counterstain, and a bluing agent to facilitate identification of positive staining cells are optionally provided.

Alternatively, the immunochemistry kits of the present invention are used in conjunction with commercial antibody binding detection systems, such as, for example the DAKO Envision™+ system (for example, DAKO EnVision™+System, HRP) and Biocare Medical's MACH 3™ system (for example, MACH3 detection kits labeled with either HRP or alkaline phosphatase (AP). Any chemicals that detect antigen-antibody binding may be used in the practice of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, Texas Red, AlexaFluor conjugates, and aequorin; and examples of suitable radioactive material include $^{125}I$, $^{131}I$, $^{35}S$, or $^{3}H$.

In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. The kits of the present invention may also comprise a counterstain, such as, for example, hematoxylin or hematoxilyn and eosin. A bluing agent (e.g., ammonium hydroxide) may be further provided in the kit to facilitate detection of positive staining cells.

Exemplary Embodiments

One embodiment of the invention includes an immunohistochemical method for typing a medulloblastoma as a WNT pathway tumor, a sonic hedgehog (SHH) pathway tumor, or a non-WNT/non-SHH tumor, said method comprising determining a protein expression profile for a sample obtained from said medulloblastoma by detecting expression of at least two biomarker proteins selected from the group consisting of β-catenin, YAP1, GAB1, and filamin A, and typing said medulloblastoma as a WNT pathway tumor, a SHH pathway tumor, or a non-WNT/non-SHH tumor based on said protein expression profile.

In another embodiment, the immunohistochemical method further comprises a) contacting a tissue sample obtained from said medulloblastoma with at least two antibodies selected from the group consisting of an antibody that specifically binds β-catenin, an antibody that specifically binds YAP1, an antibody that specifically binds GAB1, and an antibody that specifically binds filamin A; b) determining a protein expression profile for said tissue sample based on detection of binding of said at least two antibodies to said biomarker proteins; and c) typing said medulloblastoma as a WNT pathway tumor, a SHH pathway tumor, or a non-WNT/non-SHH tumor based on said protein expression profile.

In yet another embodiment the immunohistochemical method includes at least one antibody that specifically binds β-catenin, wherein said protein expression profile is characterized by positive nuclear expression of β-catenin, wherein said medulloblastoma is typed as a WNT pathway tumor.

In yet another embodiment of the invention, the immunohistochemical method includes at least one antibody that specifically binds β-catenin, wherein said protein expression profile is characterized by negative nuclear expression of β-catenin. The method can further comprise, evaluation of a protein expression profile characterized by positive and/or negative expression of one or more additional biomarker proteins selected from the group consisting of filamin A, GAB1, and YAP1, wherein positive expression of one or more biomarker proteins in a medulloblastoma is typed as a SHH pathway tumor. Alternatively, wherein said protein expression profile is characterized by negative expression of one or more additional biomarker proteins selected from the group consisting of filamin A, GAB2, and YAP1, said medulloblastoma is typed as a non-WNT/non-SHH tumor.

In yet another embodiment of the invention, the immunohistochemical method includes at least one antibody that specifically binds GAB1, wherein a protein expression profile is characterized by positive expression of GAB1, and the medulloblastoma is typed as a SHH pathway tumor. Alternatively, where the protein expression profile is characterized by negative expression of GAB1, and said protein expression profile is characterized by positive nuclear expression of β-catenin, the medulloblastoma is typed as a WNT pathway tumor. In yet another embodiment, the protein expression profile is characterized by negative nuclear expression of β-catenin, the medulloblastoma is typed as a non-WNT/non-SHH pathway-regulated tumor.

In embodiments of the invention a sample is contacted with at least three antibodies, wherein said antibodies are selected from the group consisting of an antibody that specifically binds to β-catenin, an antibody that specifically binds to YAP1, an antibody that specifically binds to GAB1, or an antibody that specifically binds to filamin A.

In yet other embodiments, a sample is contacted with an antibody that specifically binds to β-catenin, an antibody that specifically binds to YAP1, an antibody that specifically binds to GAB1, and an antibody that specifically binds to filamin A. It is contemplated that in any of the aforementioned embodiments a sample can be contacted with said antibodies sequentially, or alternatively a sample can be contacted with said antibodies simultaneously One embodiment of the invention is an immunohistochemical method for typing a medulloblastoma as a SHH pathway tumor or a non-SHH tumor, the method comprising determining a protein expression profile for a sample obtained from a medulloblastoma by detecting expression of GAB1 and typing said medulloblastoma as a SHH pathway tumor or a non-SHH tumor based on said protein expression profile. In one embodiment, the protein expression profile is characterized by positive expression of GAB1, wherein said medulloblastoma is typed as a SHH pathway tumor. Alternatively, the protein expression profile is characterized by negative expression of GAB1, wherein said medulloblastoma is typed as a non-SHH tumor.

In another embodiment of the invention, an immunohistochemical method for typing a medulloblastoma as a non-WNT/non-SHH tumor is disclosed; the method comprising determining a protein expression profile for a sample obtained from said medulloblastoma by detecting expression of filamin A, and typing said medulloblastoma as a non-WNT/non-SHH tumor based on said protein expression profile. In one embodiment, the said protein expression profile is characterized by negative expression of filamin A, and said medulloblastoma is typed as a non-WNT/non-SHH tumor.

An embodiment of the invention also includes a method of identifying a subject with a medulloblastoma that would benefit from treatment with a WNT signaling pathway inhibitor or a sonic hedgehog (SHH) pathway signaling inhibitor, said method comprising typing said medulloblastoma as a WNT pathway tumor according to the aforementioned methods, or typing said medulloblastoma as a SHH pathway tumor according to the methods above thereby identifying said subject. The embodiment of the can further comprise treating said subject with said WNT signaling pathway inhibitor when said medulloblastoma is typed as a WNT pathway tumor or with a SHH signaling pathway inhibitor when said medulloblastoma is typed as a SHH pathway tumor.

In yet another embodiment a method for selecting a therapy for a subject with a medulloblastoma is disclosed; the method comprising typing a sample obtained from a medulloblastoma according to the method of any one of the aforementioned embodiments and selecting a therapy based on the typing.

In one embodiment a method for determining whether a subject is eligible for entry into a clinical trial for treating medulloblastomas regulated by the WNT signaling pathway is included, comprising typing a medulloblastoma in said subject according to the method of any one of embodiments discussed herein, where said subject is eligible if said medulloblastoma is typed as a WNT pathway tumor. Alternatively, a method for determining whether a subject is eligible for entry into a clinical trial for treating medulloblastomas regulated by the SHH signaling pathway is disclosed, comprising typing a medulloblastoma in said subject according to the method of any one of aforementioned embodiments discussed herein. Accordingly, the subject is eligible if said medulloblastoma is typed as a SHH pathway tumor.

Another embodiment of the invention is a method for determining whether a subject is eligible for entry into a clinical trial for treating medulloblastomas that are non-WNT/non-SHH tumors, comprising typing a medulloblastoma in said subject according to the method of any one of the aforementioned embodiments disclosed herein. Accordingly, the subject is eligible if said medulloblastoma is typed as a non-WNT/non-SHH tumor.

One embodiment of the invention comprises a kit for typing a medulloblastoma as a WNT pathway tumor, a sonic hedgehog (SHH) pathway tumor, or a non-WNT/non-SHH tumor, the kit comprising at least two antibodies selected from the group consisting of an antibody that specifically binds β-catenin, an antibody that specifically binds YAP1, an antibody that specifically binds GAB1, or an antibody that specifically binds filamin A. In a preferred embodiment, the kit can comprise at least three of said antibodies, for example, an antibody that specifically binds β-catenin, an antibody that specifically binds YAP1, an antibody that specifically binds GAB1, or an antibody that specifically binds filamin A. Optionally, the kit of any one of embodiments can further comprise reagents for the detection of antibody binding to said β-catenin, YAP1, GAB1, filamin A, or any combination thereof. The kit of any one of the embodiments can further comprise at least one positive control sample. It is also contemplated that the kit of any one of embodiments can further comprise instructions for use.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXPERIMENTAL

Example 1

Study Tumor Cohorts

The main study materials consisted of FFPE tissues from 235 medulloblastomas, representing primary surgical resections from children treated on the SIOP/UKCCSG CNS9102 (PNET3) and CNS9204 trials and from other infants (aged <3 years) and adults (aged >16 years) treated at Washington University, St. Louis, the Children's Hospital of Los Angeles, and Emory University, Atlanta. The cohort's demographics match those of other previously reported medulloblastoma patient populations. (See Ellison D W, Dalton J, Kocak M, et al: Medulloblastoma: clinicopathological correlates of SHH, WNT, and non-SHH/WNT molecular subgroups. *Acta Neuropathol* 121:381-96, 2011; herein incorporated by reference in its entirety).

A separate series of pediatric medulloblastomas (n=26) was used to validate the immunohistochemical assay, the total being limited by availability of FFPE tissue. Gene expression data (Affymetrix U133Av2) were available for the cohort (n=46) from which this validation set was derived.

Example 2

Histology and Immunohistochemistry

Standard histological preparations (hematoxylin & eosin) were used to assess general architectural and cytological features, including nodule formation, differentiation along neuronal (neurocytic/ganglionic) and astrocytic lines, and large cell or anaplastic phenotypes.

Reticulin preparations were used to evaluate desmoplasia. Internodular desmoplasia was required for a diagnosis of D/N medulloblastoma, including the paucinodular D/N variant, and MBEN. The paucinodular D/N medulloblastoma displays scattered small nodules amid widespread desmoplasia. Intranodular cells in this variant uncommonly demonstrate the differentiated neurocytic phenotype of the conventional D/N tumor, but do express neuronal proteins and show low Ki-67 immunolabeling. The MBEN is defined by its large irregularly shaped nodules, pronounced internodular neurocytic differentiation, and sparse internodular desmoplastic regions.

As defined by the WHO classification of CNS tumors and restated in criteria adopted for COG trials in North America, the anaplastic medulloblastoma shows marked cytological pleomorphism across most of its area, in association with high mitotic and apoptotic counts. The large cell medulloblastoma is defined by its groups of uniform large round cells with a single nucleolus, in most cases admixed with groups of anaplastic cells. Large cell and anaplastic tumors were combined in study datasets as LC/A tumors.

Immunohistochemistry was undertaken according to established protocols with antibodies to GFAP (DAKO #M0761; 1:250), synaptophysin (Leica Microsystems #NCL-L-Synap-299; 1:400), NEU-N (Chemicon #MAB377; 1:10,000), p27$^{Kip1}$ (DAKO #M7203; 1:50), and Ki-67 (DAKO #M7240; 1:200).

SHH pathway tumors, WNT pathway tumors, and non-SHH/non-WNT tumors were disclosed by immunohistochemistry using a combination of four antibodies: β-catenin (BD #610154; 1:800; antigen retrieval—citrate buffer 20 mins Bond), GAB1 (Abcam #ab27439; 1:50; antigen retrieval—citrate buffer 20 mins Bond), filamin A (Fitzgerald #10R-F113A; 1:100; antigen retrieval—TRIS buffer 30 mins Benchmark XT), and YAP1 (Santa Cruz #sc-101199; 1:50; antigen retrieval—citrate buffer 20 mins Bond). Positive control tissues for these antibodies were: β-catenin—tissue micro-array containing samples of normal colon and colonic carcinoma; GAB1—tonsil; filamin A—appendix; YAP1—placenta.

Example 3

Frequencies and Phenotypes Among Pathological Variants

Defining the Tumor Cohort

Classic medulloblastomas dominated the study cohort, accounting for 72% of all tumors. Most classic tumors (86%) appeared as sheets of uniform small cells with a high nuclear: cytoplasmic ratio and round hyperchromatic nuclei, while the remainder (14%) had a dominant spindle-cell morphology. Focal neuronal differentiation was evident in some classic tumors, manifesting either as nodules of uniform neurocytic cells without surrounding reticulin-positive desmoplasia (non-desmoplastic nodular 'biphasic' phenotype; 7%), or as dense clusters of tiny round cells (4%), or as foci of neuropil-like matrix with an irregular border, variable area, and scattered ganglion or neurocytic cells (ganglioneuroblastoma phenotype; n=1). In these tumors, foci of neuronal differentiation demonstrated: (i) the expected moderate to strong immunoreactivities for synaptophysin and NEU-N, (ii) up-regulation of p27, and (iii) a reduced growth fraction, as assessed by Ki-67 immunolabeling. Small foci of tumor cells with cytological features suggesting astrocytic differentiation were present in only three tumors. Among childhood medulloblastomas, immunoreactivity for GFAP was generally present in reactive astrocytes, rarely in tumor cells, but GFAP-positive tumor cells were readily found in adult cases, occurring in classic and D/N, but not LC/A, tumors.

Desmoplastic medulloblastomas, which contributed 17% of all tumors, were classified as conventional D/N medulloblastoma (67%), paucinodular D/N medulloblastoma (13%), and MBEN (20%). Intranodular cells showed the expected neuronal immunophenotype and low growth fraction described above for non-desmoplastic nodular tumors. Foci of internodular cells in a few D/N tumors showed marked cytological pleomorphism amounting to anaplasia, and this cytology was occasionally associated with invasion by such cells of peripheral areas within nodules.

Anaplastic and large cell tumors contributed 10% and 1%, respectively, of the total cohort. Several non-desmoplastic tumors among infants consisted of a monomorphic population of round cells with one or more prominent nucleoli and abundant mitotic activity. Their cytological features were distinct from the conventional classic medulloblastoma, bearing similarities to the large cell phenotype, but without cytomegaly. Tumors with this phenotype made up approximately one third of non-desmoplastic tumors from children less than 3 years old.

Example 4

Medulloblastomas with SHH or WNT Signaling Pathway Aberrations Immunohistochemical Assay Gene expression data separating medulloblastomas (n=46) into five molecular subgroups, including two characterized by aberrant SHH or WNT pathway activation, were used to choose potential surrogate markers of SHH pathway activation. A subset of these tumors (n=26), for which FFPE material was available, was then used to validate a novel assay that divided tumors into three molecular categories: WNT pathway tumors, SHH pathway tumors, and non-SHH/non-WNT tumors, using four antibodies. GAB1 and filamin A were chosen as potential SHH pathway tumor markers for use alongside β-catenin, an established marker of WNT pathway medulloblastomas, and YAP1, which is a marker of WNT and SHH pathway tumors. Results of the validation of this assay are shown in FIG. 1. The validation set represents the majority of the series used to originally produce gene expression subgroups (Thompson et al. (2006) *J. Clin. Oncol.* 24(12):1924-1931). This was the first study to identify molecular subgroups of medulloblastoma. Since then, consensus among researchers in the field proposes four main molecular subgroups: WHT, SHH, group 3 (Thompson group A), and group 4 (Thompson group C). The anti-GAB1 antibody identified only tumors with a SHH pathway profile or PTCH1 mutation, but the anti-filamin A antibody identified WNT and SHH pathway tumors, but not non-SHH/non-WNT tumors (FIG. 1).

Example 6

Medulloblastoma Molecular Subgroups

Histopathological Associations

SHH Pathway Medulloblastomas

Combined immunoreactivities for GAB1, filamin A, and YAP1, indicating a SHH pathway tumor profile, were found in 31% of medulloblastomas, including all desmoplastic tumors. Desmoplastic medulloblastomas constituted 54% of SHH pathway tumors, classic and LC/A tumors contributing 29% and 17% respectively. While non-desmoplastic tumors generally showed uniform immunoreactivities for GAB1, YAP1, and filamin A, in the three types of desmoplastic tumor they displayed stronger staining in internodular regions. One exceptional classic tumor with focal anaplasia showed regional variation for filamin A, YAP1, and GAB1 immunoreactivities, which tended to align with the anaplastic phenotype.

WNT Pathway Medulloblastomas

Widespread intermediate or strong cytoplasmic β-catenin immunoreactivity was a feature of most medulloblastomas; few showed only patchy weak cytoplasmic staining for this antigen. WNT pathway medulloblastomas were identified by nuclear, as well as cytoplasmic, β-catenin immunoreactivity. In many cases, nuclear and cytoplasmic β-catenin staining combined to blanket almost all tumor cells, but strong nuclear β-catenin immunoreactivity was also seen in cell clusters alongside weak or negligible nuclear positivity. WNT pathway tumors defined by nuclear β-catenin immunoreactivity also expressed filamin A. Typically, this was patchy, weak to moderate immunostaining and less intense than that seen in SHH pathway tumors. Nuclear immunoreactivity for YAP1 was also a feature of WNT pathway tumors. WNT pathway tumors contributed 14% of all medulloblastomas in this series.

Nearly all WNT pathway medulloblastomas were classic tumors. LC/A tumors were also included, but rare (6%), and desmoplastic medulloblastomas were not represented among WNT pathway tumors. Uniform β-catenin immunoreactivity across the cells of a classic medulloblastoma was the usual phenotype. However, one large cell medulloblastoma showed a biphasic pattern for nuclear β-catenin immunoreactivity. The large cell phenotype was mainly associated with moderately strong cytoplasmic β-catenin immunoreactivity, but lacked β-catenin nucleopositivity, while clusters of cells elsewhere showed a WNT pathway phenotype.

Non-SHH/WNT Medulloblastomas

Medulloblastomas falling outside the SHH and WNT pathway categories (55%) displayed cytoplasmic, but not nuclear immunoreactivity for β-catenin (i.e., negative expression within the nuclei). Tumor cells within these non-WNT/non-SHH tumors were immunonegative for GAB1, YAP1, and filamin A, but intrinsic vascular elements were positive, providing an internal control for the method. This subgroup of medulloblastomas was dominated by classic tumors (92%), including 100% of the non-desmoplastic nodular tumors and all of those that contained small clusters of densely packed neurocytic cells. LC/A tumors made up the remainder.

Example 7

Medulloblastoma Molecular Subgroups

Cytogenetic Associations

Molecular cytogenetic data were generated using iFISH and probes to loci known to harbor CNAs in medulloblastoma: chromosome 6 (including SGK1), chromosome 17 (including HIC1), PTCH1, MYC, and MYCN. Monosomy 6 was detected in 27 tumors (13%). Most of these were WNT pathway (92%) or classic (96%) tumors. WNT pathway tumors showed very few CNAs at other targeted loci. In contrast, nearly all (97%) PTCH1 deletions, manifesting as either monosomy 9, heterozygous deletion, or relative imbalance in the setting of hyperploidy, were present in SHH pathway medulloblastomas. The one exception was classified as a non-WNT/non-SHH tumor. Almost two thirds (64%) of PTCH1 deletions were found in desmoplastic tumors. A much higher proportion of medulloblastomas without chromosome 17 CNAs was evident among SHH and WNT pathway tumors versus non-WNT/non-SHH tumors: SHH 76%, WNT 71%, non-SHH/non-WNT 17%. Most cases (71%) of MYC or MYCN amplification also occurred in the non-SHH/non-WNT tumor subgroup.

Clinical Associations

The three molecular subgroups of medulloblastoma demonstrated distinct clinical associations. SHH pathway tumors dominated medulloblastomas from infants and adults, in part reflecting the association between these age groups and desmoplastic tumors. In contrast, WNT pathway tumors nearly all presented between the ages of 6 and 12 years. The ratio of male:female patients also varied among molecular subgroups, exceeding 2:1 in the non-WNT/non-SHH tumor subgroup.

Clinical data on metastatic disease and outcome were available for children aged 3-16 years and entered into the SIOP PNET3 trial. The frequency of metastatic disease at presentation was higher in the non-WNT/non-SHH tumor subgroup than in the other two. Survival analyses revealed that WNT pathway medulloblastomas had significantly better progression-free and overall survivals than SHH pathway or non-WNT/non-SHH tumors. No significant difference in outcome was shown for LC/A tumors belonging to the SHH-pathway or non-WNT/non-SHH categories of medulloblastoma, and the trend towards a better outcome for non-LC/A SHH pathway tumors relates to the presence of desmoplastic tumors in this category.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An immunohistochemical method for typing a medulloblastoma as a WNT pathway tumor, a sonic hedgehog (SHH) pathway tumor, or a non-WNT/non-SHH tumor, said method comprising determining a protein expression profile for a sample obtained from said medulloblastoma by detecting expression of at least two biomarker proteins, wherein the biomarker proteins comprise
   (a) GAB1 and YAP1;
   (b) GAB1 and β-catenin;
   (c) GAB1 and filamin A; or
   (d) filamin A and β-catenin;
   and typing said medulloblastoma as a WNT pathway tumor, a SHH pathway tumor, or a non-WNT/non-SHH tumor based on said protein expression profile.

2. The method of claim 1, comprising:
   a) contacting a tissue sample obtained from said medulloblastoma with at least two antibodies specific to biomarker proteins comprising
      (i) an antibody that specifically binds β-catenin and an antibody that specifically binds GAB1;
      (ii) an antibody that specifically binds β-catenin and an antibody that specifically binds filamin A;
      (iii) an antibody that specifically binds GAB1 and an antibody that specifically binds filamin A; or
      (iv) an antibody that specifically binds YAP1 and an antibody that specifically binds GAB1;
   b) determining a protein expression profile for said tissue sample based on detection of binding of said at least two antibodies to said biomarker proteins; and
   c) typing said medulloblastoma as a WNT pathway tumor, a SHH pathway tumor, or a non-WNT/non-SHH tumor based on said protein expression profile.

3. The method of claim 2, wherein said protein expression profile is characterized by positive nuclear expression of β-catenin, wherein said medulloblastoma is typed as a WNT pathway tumor.

4. A method of identifying a subject with a medulloblastoma that would benefit from treatment with a WNT signaling pathway inhibitor, said method comprising typing said medulloblastoma as a WNT pathway tumor according to the method of claim 3, thereby identifying said subject.

5. The method of claim 4, further comprising
   treating said subject with said WNT signaling pathway inhibitor when said medulloblastoma is typed as a WNT pathway tumor.

6. The method of claim 2, wherein said protein expression profile is characterized by negative nuclear expression of β-catenin.

7. The method of claim 6, wherein
   (a) said protein expression profile is characterized by positive expression of one or more additional biomarker proteins selected from the group consisting of filamin A, GAB1, and YAP1, wherein said medulloblastoma is typed as a SHH pathway tumor; or,
   (b) said protein expression profile is characterized by negative expression of one or more additional biomarker proteins selected from the group consisting of filamin A, GAB1, and YAP1, wherein said medulloblastoma is typed as a non-WNT/non-SHH tumor.

8. The method of claim 2, wherein said protein expression profile is characterized by positive expression of GAB1, wherein said medulloblastoma is typed as a SHH pathway tumor.

9. The method of claim 2, wherein said protein expression profile is characterized by negative expression of GAB1.

10. The method of claim 9, wherein
    (a) said protein expression profile is characterized by positive nuclear expression of β-catenin, wherein said medulloblastoma is typed as a WNT pathway tumor; or,
    (b) said protein expression profile is characterized by negative nuclear expression of β-catenin, wherein said medulloblastoma is typed as a non-WNT/non-SHH pathway-regulated tumor.

11. The method of claim 2, wherein said sample is contacted with at least three antibodies, wherein said antibodies are selected from the group consisting of an antibody that specifically binds to β-catenin, an antibody that specifically binds to YAP1, an antibody that specifically binds to GAB1, and an antibody that specifically binds to filamin A.

12. The method of claim 2, wherein said sample is contacted with an antibody that specifically binds to β-catenin, an antibody that specifically binds to YAP1, an antibody that specifically binds to GAB1, and an antibody that specifically binds to filamin A.

13. The method of claim 2, wherein said sample is contacted with said antibodies sequentially.

14. The method of claim 2, wherein said sample is contacted with said antibodies simultaneously.

15. A method for selecting a therapy for a subject with a medulloblastoma, said method comprising typing a sample obtained from said medulloblastoma according to the method of claim 1, and selecting a therapy based on said typing.

16. A method for determining whether a subject is eligible for entry into a clinical trial for treating medulloblastomas comprising:
  (a) determining whether a subject is eligible for entry into a clinical trial for treating medulloblastomas regulated by the WNT signaling pathway, comprising typing a medulloblastoma in said subject according to the method of claim 1, wherein said subject is eligible if said medulloblastoma is typed as a WNT pathway tumor;
  (b) determining whether a subject is eligible for entry into a clinical trial for treating medulloblastomas regulated by the SHH signaling pathway, comprising typing a medulloblastoma in said subject according to the method of claim 1, wherein said subject is eligible if said medulloblastoma is typed as a SHH pathway tumor; or,
  (c) determining whether a subject is eligible for entry into a clinical trial for treating medulloblastomas that are non-WNT/non-SHH tumors, comprising typing a medulloblastoma in said subject according to the method of claim 1, wherein said subject is eligible if said medulloblastoma is typed as a non-WNT/non-SHH tumor.

17. The immunohistochemical method of claim 1 wherein said biomarker proteins comprise GAB1, YAP1 and β-catenin.

18. An immunohistochemical method for typing a medulloblastoma as a SHH pathway tumor or a non-SHH tumor, said method comprising determining a protein expression profile for a sample obtained from said medulloblastoma by detecting expression of GAB1 and typing said medulloblastoma as a SHH pathway tumor or a non-SHH tumor based on said protein expression profile.

19. The method of claim 18, wherein said protein expression profile is characterized by positive expression of GAB1, wherein said medulloblastoma is typed as a SHH pathway tumor.

20. The method of claim 18, wherein said protein expression profile is characterized by negative expression of GAB1, wherein said medulloblastoma is typed as a non-SHH tumor.

21. An immunohistochemical method for typing a medulloblastoma as a non-WNT/non-SHH tumor, said method comprising determining a protein expression profile for a sample obtained from said medulloblastoma by detecting expression of filamin A, and typing said medulloblastoma as a non-WNT/non-SHH tumor based on said protein expression profile.

22. The method of claim 21, wherein said protein expression profile is characterized by negative expression of filamin A, wherein said medulloblastoma is typed as a non-WNT/non-SHH tumor.

23. A kit for typing a medulloblastoma as a WNT pathway tumor, a sonic hedgehog (SHH) pathway tumor, or a non-WNT/non-SHH tumor, said kit comprising at least two antibodies comprising
  (a) an antibody that specifically binds β-catenin and an antibody that specifically binds GAB1;
  (b) an antibody that specifically binds β-catenin and an antibody that specifically binds filamin A;
  (c) an antibody that specifically binds GAB1 and an antibody that specifically binds filamin A; and
  (d) an antibody that specifically binds YAP1 and an antibody that specifically binds GAB1.

24. The kit of claim 23, comprising at least three antibodies comprising an antibody that specifically binds GAB1, an antibody that specifically binds filamin A, an antibody that specifically binds YAP1 or an antibody that specifically binds β-catenin.

25. The kit of claim 23, comprising
  (a) an antibody that specifically binds β-catenin, an antibody that specifically binds YAP1, an antibody that specifically binds GAB1, and an antibody that specifically binds filamin A; or,
  (b) said kit further comprises reagents for the detection of antibody binding to said β-catenin, YAP1, GAB1, filamin A, or any combination thereof.

* * * * *